(12) United States Patent
Nakamura et al.

(10) Patent No.: US 7,919,611 B2
(45) Date of Patent: Apr. 5, 2011

(54) NUCLEOTIDE PRIMER SET AND NUCLEOTIDE PROBE FOR DETECTING GENOTYPE OF N-ACETYLTRANSFERASE-2 (NAT2)

(75) Inventors: Naoko Nakamura, Kawasaki (JP); Keiko Ito, Kawasaki (JP); Koji Hashimoto, Atsugi (JP); Nobuhiro Gemma, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 394 days.

(21) Appl. No.: 12/014,592

(22) Filed: Jan. 15, 2008

(65) Prior Publication Data

US 2010/0003671 A1 Jan. 7, 2010

(30) Foreign Application Priority Data

Mar. 28, 2007 (JP) ................................. 2007-084289

(51) Int. Cl.
*C07H 21/04* (2006.01)
*C12Q 1/68* (2006.01)
*C12P 19/34* (2006.01)

(52) U.S. Cl. ........................... 536/24.3; 435/6; 435/91.2

(58) Field of Classification Search ........................ None
See application file for complete search history.

(56) References Cited

U.S. PATENT DOCUMENTS

| 6,410,278 | B1 * | 6/2002 | Notomi et al. ................ 435/91.2 |
| 7,803,544 | B2 * | 9/2010 | Nakamura et al. ................. 435/6 |
| 2004/0241714 | A1 * | 12/2004 | Branch et al. ....................... 435/6 |
| 2007/0218464 | A1 * | 9/2007 | Nakamura et al. ................. 435/6 |
| 2009/0104621 | A1 * | 4/2009 | Nakamura et al. ................. 435/6 |

FOREIGN PATENT DOCUMENTS

| EP | 1 837 408 A1 | 9/2007 |
| JP | 3313358 | 5/2002 |
| JP | 2005-143492 | 6/2005 |
| JP | 2005-323563 | 11/2005 |
| JP | 2005-328707 | 12/2005 |
| JP | 2006-314205 | 11/2006 |
| JP | 2007-267636 | 10/2007 |
| WO | WO 01/73118 A2 | 10/2001 |
| WO | 02/24902 A1 | 3/2002 |
| WO | WO 02/061659 A2 | 8/2002 |
| WO | WO 2004/033722 A2 | 4/2004 |
| WO | WO 2004/069189 A2 | 8/2004 |
| WO | WO 2006075254 A2 * | 7/2006 |
| WO | WO 2008/010084 A2 | 1/2008 |

OTHER PUBLICATIONS

Machine translation of JP 2007267636. 21 pages. Obtained Jun. 5, 2010.*

Grant et al. Nucleotide sequence of an intronless gene for a human arylamine N-acetyltransferase related to polymorphic drug acetylation. Nucleic Acids Research (1989) 17(10): 3978.*
Nagamine et al. Isolation of single-stranded DNA from loop-mediated isothermal amplification products. Biochemical and Biophysical Research Communications (2002) 290(4): 1195-1198.*
Wang et al. Large-Scale Identification, Mapping, and Genotyping of Single-Nucleotide Polymorphisms in the Human Genome. Science (1998) 280: 1077-1082.*
Jain, K. K. "Applications of AmpliChip $^{TM}$ CYP450", Mol Diagn. 9, pp. 119-127 (2005).
Breslauer, et al. "Predicting DNA duplex stability form the base sequence", Proc. Natl. Acad. Sci. USA, vol. 83, pp. 3746-3750, Jun. (1986).
Freier, et al. "Improved free-energy parameters for predictions of RNA duplex staiblity", Proc. Natl. Acad. Sci. USA, vol. 83, pp. 9373-9377, Dec. 1986, Biochemistry.
Schildkraut, et al. "Dependence of the Melting Temperature of DNA on Salt Concentration" Biopolymers, vol. 3, pp. 195-208 (1965).
Adrian J. Fretland, et al., "Functional characterization of human N-acetyltransferase 2 (NAT2) single nucleotide polymorphisms", Pharmacogenetics, vol. 11, No. 3, XP-008043638, Jan. 1, 2001, pp. 207-215.
Naoko Nakamura, et al., "Detection of Six Single-Nucleotide Polymorphisms Associated with Rheumatoid Arthritis by a Loop-Mediated Isothermal Amplification Method and an Electrochemical DNA Chip", Analytical Chemistry, vol. 79, No. 24, XP-002489746, Dec. 15, 2007, pp. 9484-9493.
U.S. Appl. No. 11/624,814, filed Jan. 19, 2007, Nakamura et al.
David W. Hein, et al., "Metabolic Activation of N-Hydroxyarylamines and N-Hydroxyarylamides by 16 Recombinant Human NAT2 Allozymes: Effects of 7 Specific NAT2 Nucleic Acid Substitutions", Cancer Research, 55, Aug. 15, 1995, pp. 3531-3536.
U.S. Appl. No. 12/341,295, filed Dec. 22, 2008, Nakamura et al.
J. Nemoto, et al., "Rapid Detection of Shiga toxin-producing *Escherichia coil* by multiplex LAMP, a New DNA amplification method", Abstracts of the General Meeting of the American Society for Microbiology, vol. 103, XP009109834, May 19, 2003, p. P-065.
U.S. Appl. No. 12/015,645, filed Jan. 17, 2008, Nakamura et al.

* cited by examiner

*Primary Examiner* — Young J Kim
*Assistant Examiner* — Angela M Bertagna
(74) *Attorney, Agent, or Firm* — Oblon, Spivak, McClelland, Maier & Neustadt, L.L.P.

(57) ABSTRACT

There is provided a nucleotide primer set for LAMP amplification, used for detecting genotypes of single-nucleotide polymorphisms G590A, G857A and T341C of a NAT2 gene. There is also provided a nucleotide probe for detection of an amplification product amplified with the primer set according to the present invention. There is also provided a method of detecting the genotypes of NAT2 gene single-nucleotide polymorphisms G590A, G857A and T341C by using the primer set according to the present invention.

18 Claims, 25 Drawing Sheets

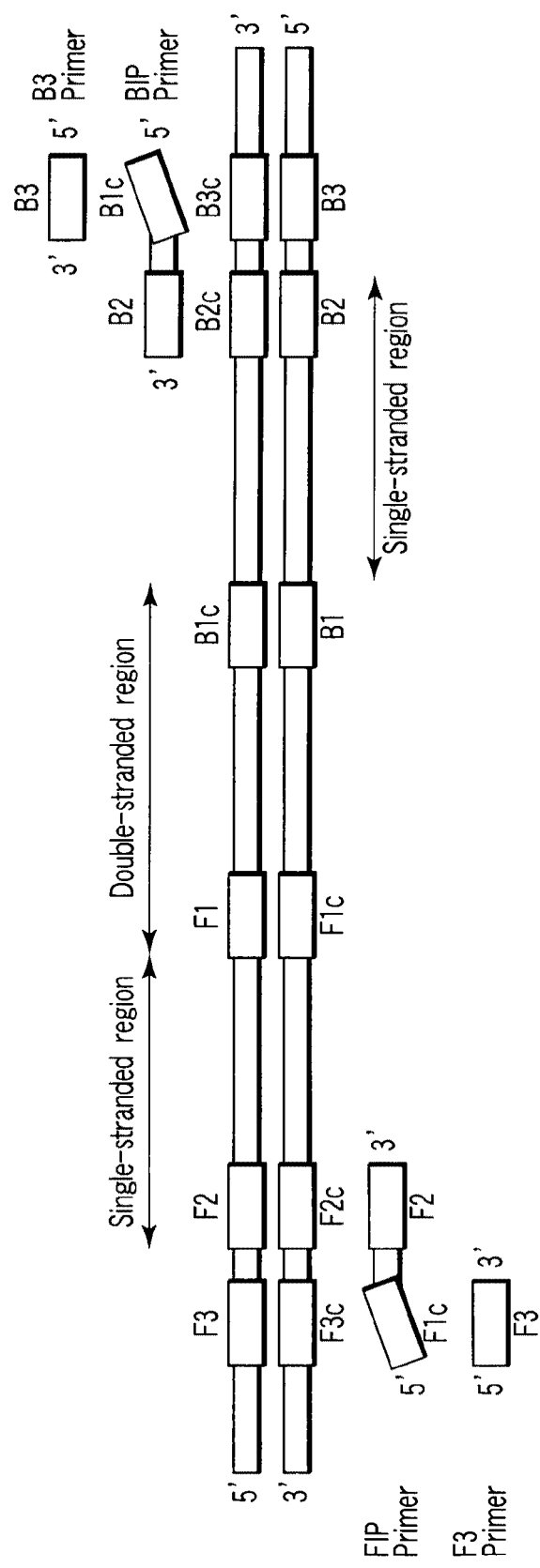
F I G. 1

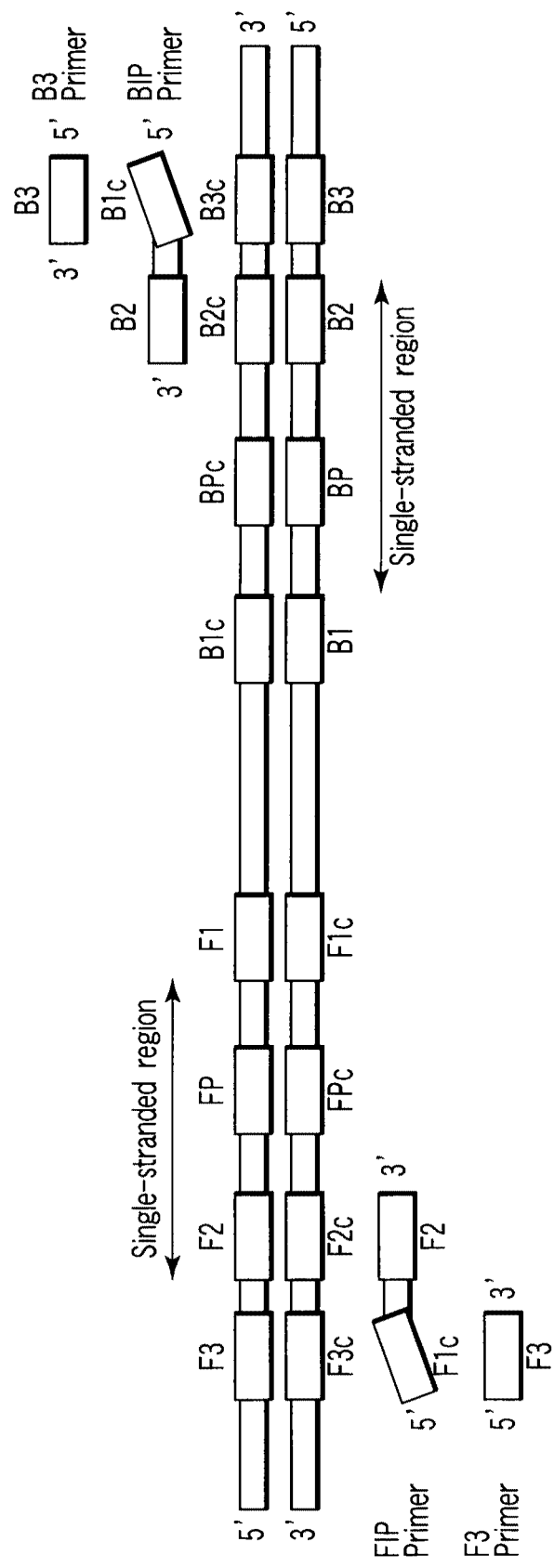
F I G. 5

```
NAT1.prj 241:TCTTCAACACCAGATCCGAGCTGTTCCCTTTGAGAACCTTAACATCCATTGTGGGGATGC 300
NAT2.prj  81:TCTTGAGCACCAGATCCGGGCTGTTCCCTTTGAGAACCTTAACATGCATTGTGGGCAAGC 140
            ****  ***************  *************************  ********* * **

NAT1.prj 301:CATGGACTTAGGCTTAGAGGCCATTTTTGATCAAGTTGTGAGAAGAAATCGGGGTGGATG 360
NAT2.prj 141:CATGGAGTTGGGCTTAGAGGCTATTTTTGATCACATTGTAAGAAGAAACCGGGTGGGTG  200
            ****** ** *********** ********** * ***** ********  *** ******** **

NAT1.prj 361:GTGTCTCCAGGTCAATCATCTTCTGTACTGGGCTCTGACCACTATTGGTTTTGAGACCAC 420
NAT2.prj 201:GTGTCTCCAGGTCAATCAACTTCTGTACTGGGCTCTGACCACAATCGGTTTTCAGACCAC 260
            ****************** ********************** ** ****** *******

NAT1.prj 421:GATGTTGGGAGGGTATGTTTACAGCACTCCAGCCAAAAAATACAGCACTGGCATGATTCA 480
NAT2.prj 261:AATGTTAGGAGGGTATTTTTACATCCCTCCAGTTAACAAATACAGCACTGGCATGGTTCA 320
            ***** ********* ****** *  ******  **  ****************** ****

NAT1.prj 481:CCTTCTCCTGCAGGTGACCATTGATGGCAGGAACTACATTGTCGATGCTGGGTTTGGACG 540
NAT2.prj 321:CCTTCTCCTGCAGGTGACCATTGACGGCAGGAATTACATTGTCGATGCTGGGTCTGGAAG 380
                                T341C
            ************************ ********* ***********************  **** *

NAT1.prj 541:CTCATACCAGATGTGGCAGCCTCTGGAGTTAATTTCTGGGAAGGATCAGCCTCAGGTGCC 600
NAT2.prj 381:CTCCTCCCAGATGTGGCAGCCTCTAGAATTAATTTCTGGGAAGGATCAGCCTCAGGTGCC 440
            *** * ****************** ** ** ********************** *******

NAT1.prj 601:TTGTGTCTTCCGTTTGACGGAAGAGAATGGATTCTGGTATCTAGACCAAATCAGAAGGGA 660
NAT2.prj 441:TTGCATTTTCTGCTTGACAGAAGAGAGAGGAATCTGGTACCTGGACCAAATCAGGAGAGA 500
            ***   * *** * ***** ******  *** *******  ** ********** ** **

NAT1.prj 661:ACAGTACATTCCAAATGAAGAATTTCTTCATTCTGATCTCCTAGAAGACAGCAAATACCG 720
NAT2.prj 501:GCAGTATATTACAAACAAAGAATTTCTTAATTCTCATCTCCTGCCAAAGAAGAAACACCA 560
             ***** ***  ****  ***********  **** ********    * *  *** ***

○ Reported mutation site
```

FIG. 9A

```
NAT1.prj  721: AAAAATCTACTCCTTTACTCTTAAGCCTCGAACAATTGAAGATTTTGAGTCTATGAATAC 780
NAT2.prj  561: AAAAATATACTTATTTACGCTTGAACCTC(G)AACAATTGAAGATTTTGAGTCTATGAATAC 620
                                            G590A
               ******  ****  ***** *** * ****************************

NAT1.prj  781: ATACCTGCAGACATCTCCATCATCTGTGTTTACTAGTAAATCATTTTGTTCCTTGCAGAC 840
NAT2.prj  621: ATACCTGCAGACGTCTCCAACATCTTCATTTATAACCACATCATTTTGTTCCTTGCAGAC 680
               ************ ***** ***** ****  * * ********************

NAT1.prj  841: CCCAGATGGGGTTCACTGTTTGGTGGGCTTCACCCTCACCCATAGGAGATTCAATTATAA 900
NAT2.prj  681: CCCAGAAGGGGTTTACTGTTTGGTGGGCTTCATCCTCACCTATAGAAAATTCAATTATAA 740
               ****** ****** ****************** ******* **** * ************

NAT1.prj  901: GGACAATACAGATCTAATAGAGTTCAAGACTCTGAGTGAGGAAGAAATAGAAAAAGTGCT 960
NAT2.prj  741: AGACAATACAGATCTGGTCGAGTTTAAAACTCTCACTGAGGAAGAGGTTGAAGAAGTGCT 800
               ************* * ***** ** ****  * ********* * ***  *** *******

NAT1.prj  961: GAAAAATATATTTAATATTTCCTTGCAGAGAAAGCTTGTGCCCAAACATGGTGATAGATT 1020
NAT2.prj  801: GA(A)AAATATATTTAAGATTTCCTTGGGGAGAAATCTCGTGCCCAAACCTGGTGATG(C)ATC 860
                                                                      G857A
               ** ************ ********* ******  * ********** ******* ***

NAT1.prj 1021: TTTTACTATTTAGAATAAGGAGTAAAACAATCTTGTCTATTTGT--CATCCAGCTCACCA 1078
NAT2.prj  861: CCTTACTATTTAGAATAAGGAACAAAATAAACCCTTGTGTATGTATCACCCAACTCACTA 920
                ******************** **** *    * * *** *** *** ***** *

NAT1.prj 1079: GTTATCAACTGACGACCTATCATGTATCTTCTGTACCCTTACCTTATTTTGAAGAAAATC 1138
NAT2.prj  921: ATTATCAACTTATGTGCTATCAGATATCCTCTCTACCCTCACGTTATTTTGAAGAAAATC 980
               ********* * *  ***** ****  ***  ****** ** ******************

O  Reported mutation site
```

FIG. 9B

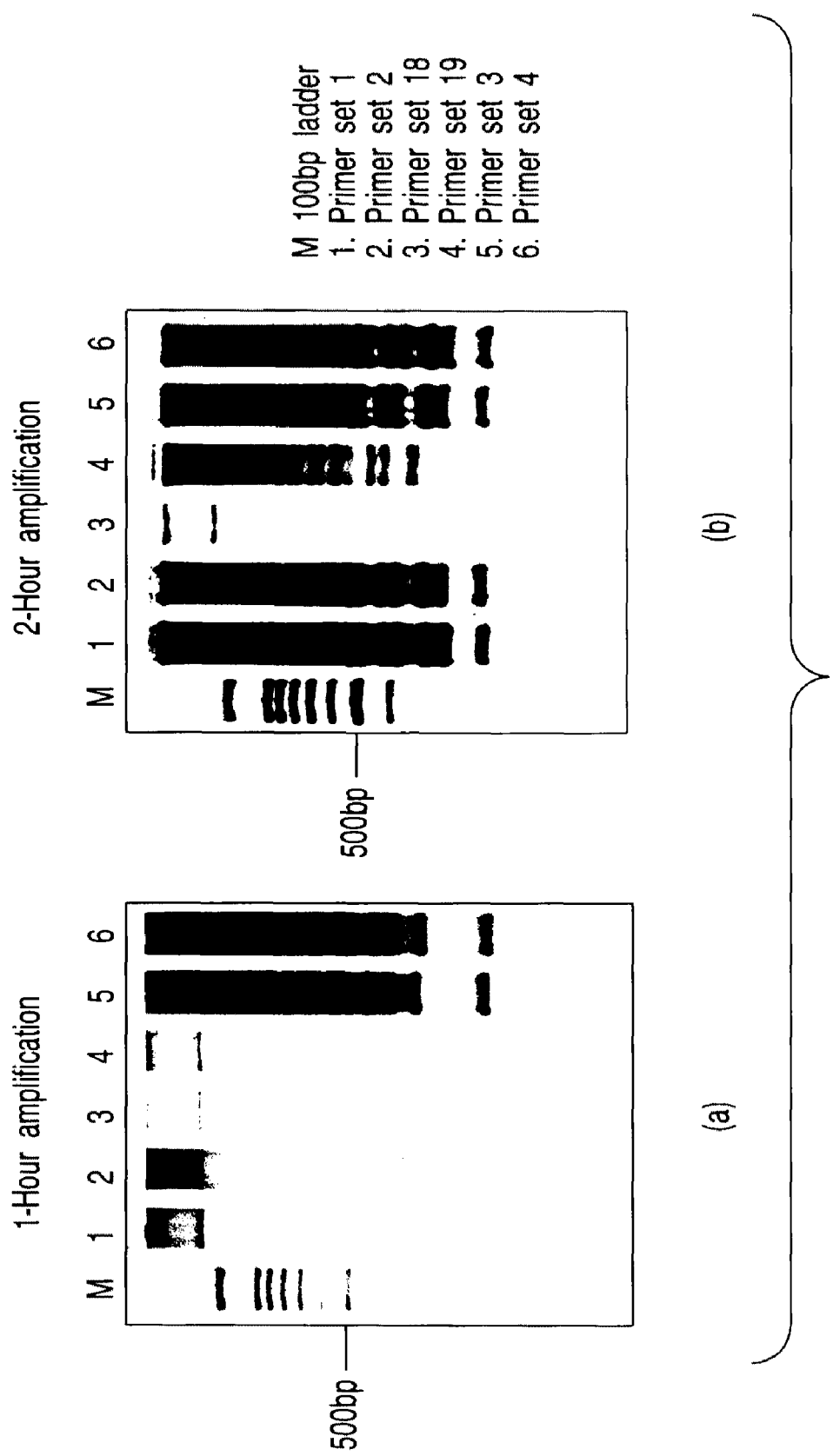
F I G. 10

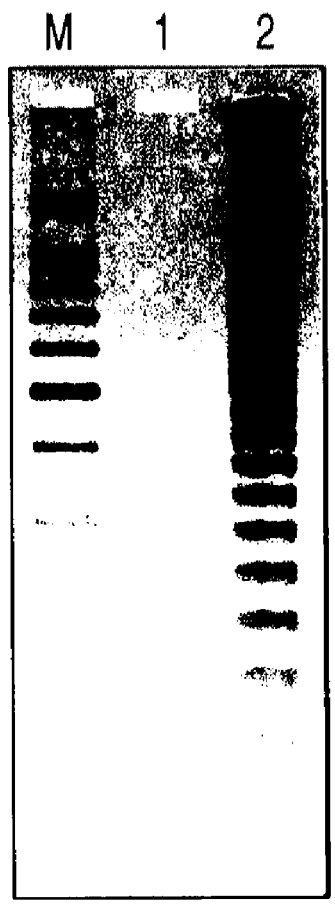
M 100bp ladder
1. Without non-specific amplification
2. With non-specific amplification
F I G. 12

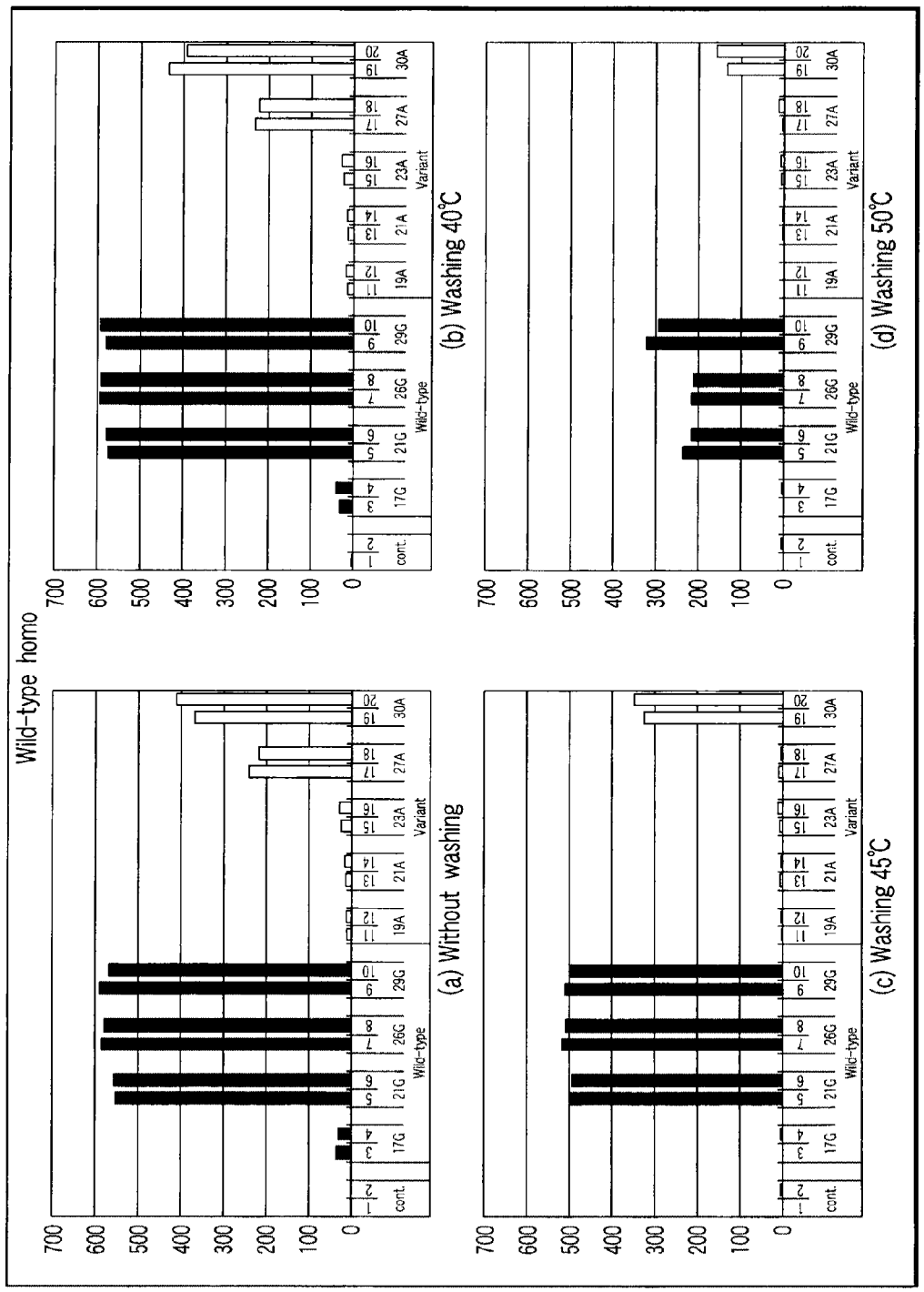
F I G. 15A

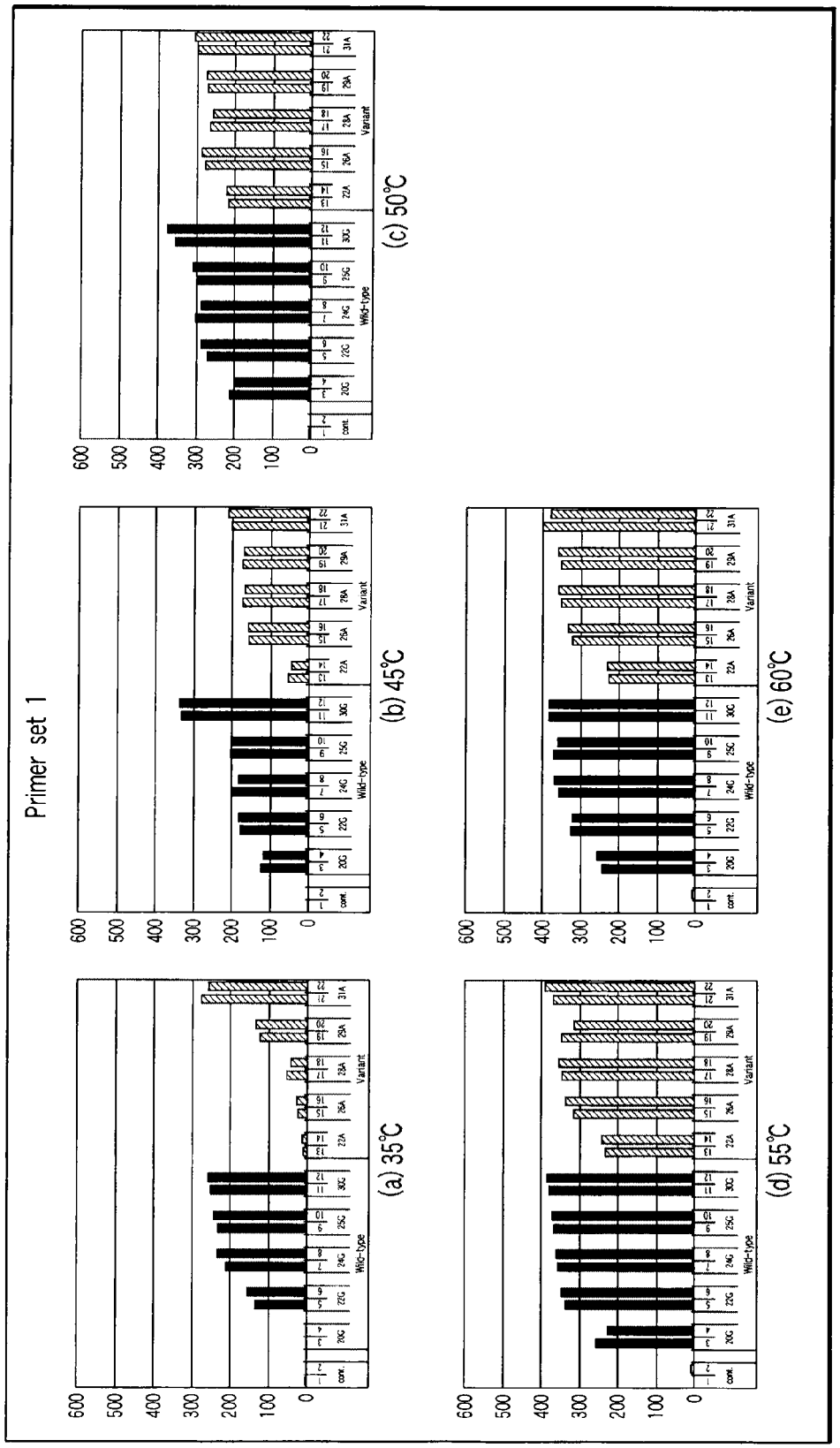
F I G. 16A

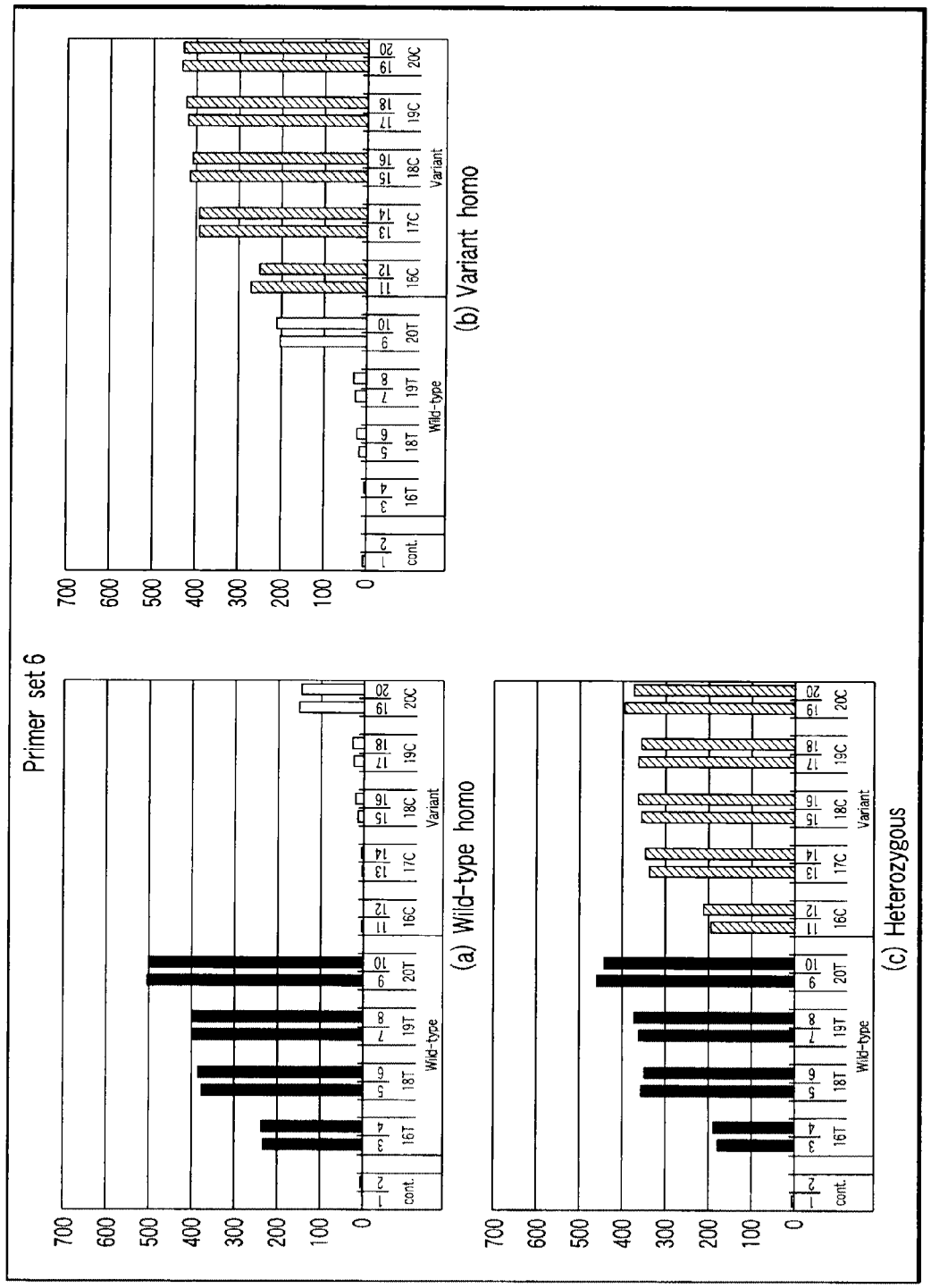
F I G. 18A

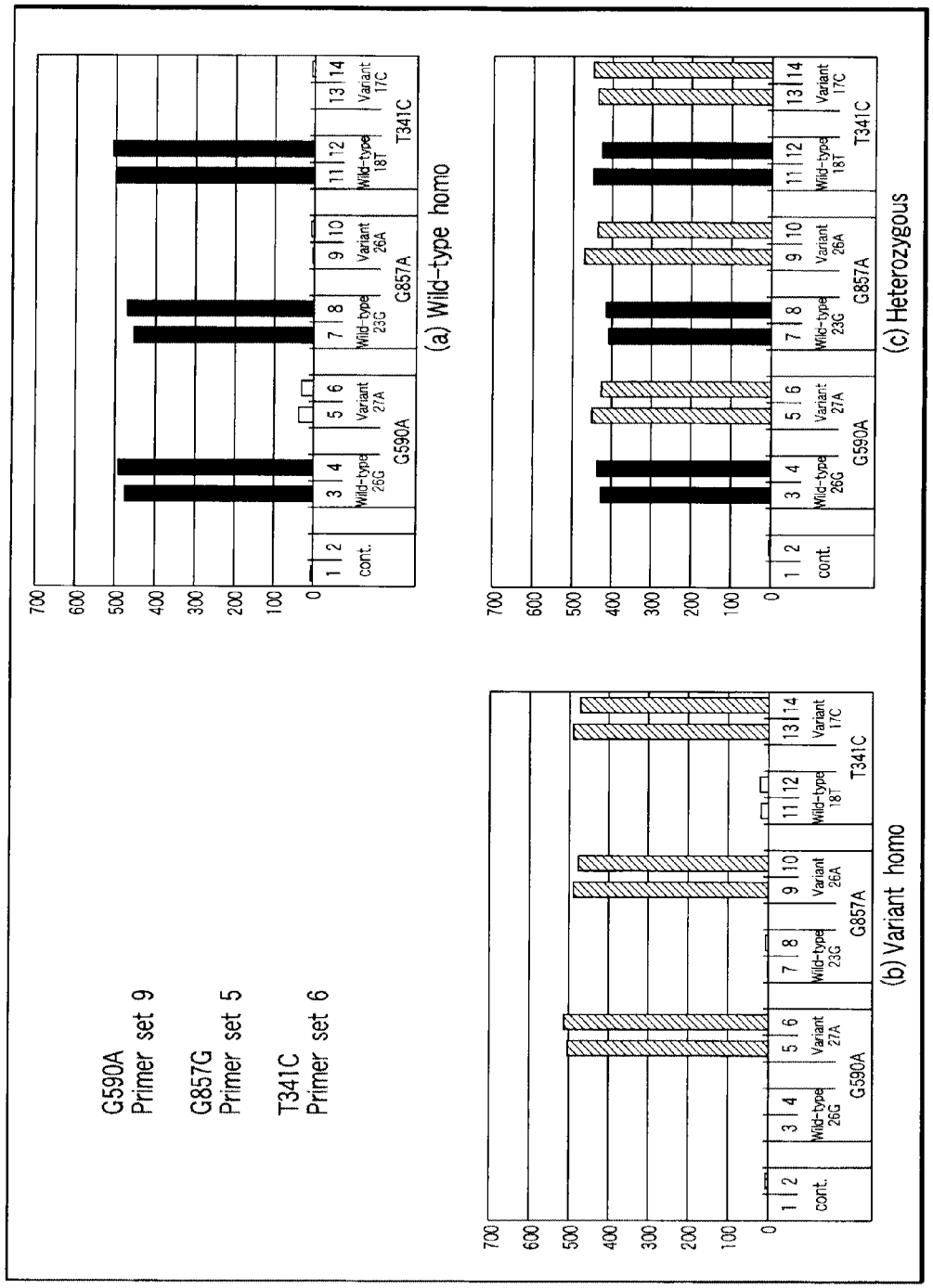
F I G. 20A

NUCLEOTIDE PRIMER SET AND NUCLEOTIDE PROBE FOR DETECTING GENOTYPE OF N-ACETYLTRANSFERASE-2 (NAT2)

CROSS-REFERENCE TO RELATED APPLICATIONS

This application is based upon and claims the benefit of priority from prior Japanese Patent Application No. 2007-084289, filed Mar. 28, 2007, the entire contents of which are incorporated herein by reference.

BACKGROUND OF THE INVENTION

1. Field of the Invention

The present invention relates to a nucleotide primer set and a detection probe for detecting a genotype of a single-nucleotide polymorphism in an N-acetyltransferase 2 (NAT2) gene.

2. Description of the Related Art

N-acetyltransferase 2 (NAT2) is involved in the metabolism of clinically important pharmaceuticals such as tuberculosis medicine isoniazid (INH) and salazosulfapyridine. Salazosulfapyridine is used for treatment of ulcerative colitis, rheumatoid arthritis, and the like.

It is known that there are genetic polymorphisms in the gene coding NAT2. The phenotype higher in NAT2 activity is called a rapid acetylator (RA), and that lower in activity is called a slow acetylator (SA). It is said that there are four kinds of polymorphisms (NAT2*4, NAT2*5, NAT*6, NAT2*7) in Japanese. NAT2*4 is a wild-type polymorphism. Mutant alleles NAT2*5, NAT*6, and NAT2*7 can be identified by analyzing the genotype of single-nucleotide polymorphisms T341C, G590A, and G857A, respectively. A person having a homozygote or composite heterozygote of the mutant allele is highly likely an SA, and has higher incidence of adverse drug action.

For this reason, identifying the mutation of the NAT2 gene is helpful to avoid adverse drug reactions. It is also possible to select pharmaceutical administration and treatment suitable for individual patient by determining the genotype of the NAT2 gene.

The single-nucleotide polymorphism is generally detected by amplifying a target nucleotide with the Polymerase chain reaction (PCR) method and detecting wild-type and variant amplification products with a specific probe (see, the reference "Jain K. K., Application of Amplicip. CYP450, Mol Diagn. 9, 119-27 (2005)"). However, the PCR method has disadvantages such as complicated procedure of pretreatment including nucleotide extraction, demand for a complex temperature-regulating device such as a thermal cycler, and a longer reaction period of two hours or more. Amplification products by the PCR method are double-stranded chains, and thus, there is a problem in that the complementary chain degrades the detection sensitivity, while functioning as a competitor to the probe during detection. Various methods of converting the amplification product into a single-stranded chain, for example, by decomposing or separating a complementary chain by using an enzyme or magnetic beads, have been studied, but these methods also have a problem in that the operation is complicated and expensive.

BRIEF SUMMARY OF THE INVENTION

According to one aspect of the present invention, there is provided a nucleotide primer set for LAMP amplification, used for detecting a genotype of a single-nucleotide polymorphism G590A of a NAT2 gene, wherein when a target nucleotide has F3 region, F2 region and F1 region in turn from a 5' terminal and B3c region, B2c region and B1c region in turn from a 3' terminal, and when there are nucleotide primers including an FIP primer having a sequence identical with that of the F2 region in the 3' terminal side and a sequence complementary to the F1 region in the 5' terminal side, an F3 primer having a sequence identical with that of the F3 region, a BIP primer having a sequence complementary to the B2c region in the 3' terminal side and a sequence identical with that of the B1c region in the 5' terminal side, and a B3 primer having a sequence complementary to the B3c region, wherein the primer set comprises: an FIP primer and a BIP primer selected from the primer sets 1 to 16 shown in Tables 2 and 3; an F3 primer binding to a region within 60 bases from the 5' terminal of the F2 region of the target nucleotide; and a B3 primer binding to a region within 60 bases from the 3' terminal of the B2c region of the target nucleotide.

The primer sets 1 to 16 shown in Tables 2 and 3 are as follows:

Primer set 1: FIP primer of SEQ ID No. 1 and BIP primer of SEQ ID No. 7,
Primer set 2: FIP primer of SEQ ID No. 2 and BIP primer of SEQ ID No. 7,
Primer set 3: FIP primer of SEQ ID No. 5 and BIP primer of SEQ ID No. 7,
Primer set 4: FIP primer of SEQ ID No. 6 and BIP primer of SEQ ID No. 7,
Primer set 5: FIP primer of SEQ ID No. 10 and BIP primer of SEQ ID No. 13,
Primer set 6: FIP primer of SEQ ID No. 10 and BIP primer of SEQ ID No. 14,
Primer set 7: FIP primer of SEQ ID No. 15 and BIP primer of SEQ ID No. 11,
Primer set 8: FIP primer of SEQ ID No. 15 and BIP primer of SEQ ID No. 12,
Primer set 9: FIP primer of SEQ ID No. 15 and BIP primer of SEQ ID No. 13,
Primer set 10: FIP primer of SEQ ID No. 15 and BIP primer of SEQ ID No. 14,
Primer set 11: FIP primer of SEQ ID No. 16 and BIP primer of SEQ ID No. 11,
Primer set 12: FIP primer of SEQ ID No. 16 and BIP primer of SEQ ID No. 12,
Primer set 13: FIP primer of SEQ ID No. 16 and BIP primer of SEQ ID No. 13,
Primer set 14: FIP primer of SEQ ID No. 16 and BIP primer of SEQ ID No. 14,
Primer set 15: FIP primer of SEQ ID No. 17 and BIP primer of SEQ ID No. 13, and
Primer set 16: FIP primer of SEQ ID No. 17 and BIP primer of SEQ ID No. 14.

According to another aspect of the present invention, there is provided a nucleotide primer set for LAMP amplification, used for detecting a genotype of a single-nucleotide polymorphism G857A of a NAT2 gene, wherein the primer set comprises: an FIP primer and a BIP primer selected from the primer sets 1 to 5 shown in Table 4; an F3 primer binding to a region within 60 bases from the 5' terminal of the F2 region of the target nucleotide; and a B3 primer binding to a region within 60 bases from the 3' terminal of the B2c region of the target nucleotide.

The primer sets 1 to 5 shown in Table 4 are as follows:
Primer set 1: FIP primer of SEQ ID No. 20 and BIP primer of SEQ ID No. 21, Primer set 2: FIP primer of SEQ ID No. 20 and BIP primer of SEQ ID No. 22,
Primer set 3: FIP primer of SEQ ID No. 20 and BIP primer of SEQ ID No. 23,
Primer set 4: FIP primer of SEQ ID No. 20 and BIP primer of SEQ ID No. 25, and
Primer set 5: FIP primer of SEQ ID No. 20 and BIP primer of SEQ ID No. 26.

According to another aspect of the present invention, there is provided a nucleotide primer set for LAMP amplification, used for detecting a genotype of a single-nucleotide polymorphism T341C of a NAT2 gene, wherein the primer set comprises: an FIP primer and a BIP primer selected from the primer sets 1 to 10 shown in Table 5; an F3 primer binding to a region within 60 bases from the 5' terminal of the F2 region of the target nucleotide; and a B3 primer binding to a region within 60 bases from the 3' terminal of the B2c region of the target nucleotide.

The primer sets 1 to 10 shown in Table 5 are as follows:
Primer set 1: FIP primer of SEQ ID No. 33 and BIP primer of SEQ ID No. 30,
Primer set 2: FIP primer of SEQ ID No. 33 and BIP primer of SEQ ID No. 31,
Primer set 3: FIP primer of SEQ ID No. 33 and BIP primer of SEQ ID No. 32,
Primer set 4: FIP primer of SEQ ID No. 34 and BIP primer of SEQ ID No. 30,
Primer set 5: FIP primer of SEQ ID No. 34 and BIP primer of SEQ ID No. 31,
Primer set 6: FIP primer of SEQ ID No. 34 and BIP primer of SEQ ID No. 32,
Primer set 7: FIP primer of SEQ ID No. 35 and BIP primer of SEQ ID No. 32,
Primer set 8: FIP primer of SEQ ID No. 36 and BIP primer of SEQ ID No. 32,
Primer set 9: FIP primer of SEQ ID No. 37 and BIP primer of SEQ ID No. 32, and
Primer set 10: FIP primer of SEQ ID No. 38 and BIP primer of SEQ ID No. 32.

According to another aspect of the present invention, there is provided a nucleotide primer set for LAMP amplification, used for detecting genotypes of single-nucleotide polymorphisms G590A and G857A of a NAT2 gene, wherein the primer set comprises: an FIP primer and a BIP primer selected from the primer sets 1 to 8 shown in Table 6; an F3 primer binding to a region within 60 bases from the 5' terminal of the F2 region of the target nucleotide; and a B3 primer binding to a region within 60 bases from the 3' terminal of the B2c region of the target nucleotide.

The primer sets 1 to 8 shown in Table 6 are as follows:
Primer set 1: FIP primer of SEQ ID No. 42 and BIP primer of SEQ ID No. 43,
Primer set 2: FIP primer of SEQ ID No. 42 and BIP primer of SEQ ID No. 44,
Primer set 3: FIP primer of SEQ ID No. 45 and BIP primer of SEQ ID No. 43,
Primer set 4: FIP primer of SEQ ID No. 45 and BIP primer of SEQ ID No. 46,
Primer set 5: FIP primer of SEQ ID No. 47 and BIP primer of SEQ ID No. 43,
Primer set 6: FIP primer of SEQ ID No. 48 and BIP primer of SEQ ID No. 43,
Primer set 7: FIP primer of SEQ ID No. 48 and BIP primer of SEQ ID No. 46, and
Primer set 8: FIP primer of SEQ ID No. 48 and BIP primer of SEQ ID No. 44.

According to another aspect of the present invention, there is provided a method of detecting a genotype of a single-nucleotide polymorphism G590A, G857A or T341C of a NAT2 gene, comprising the steps of: obtaining an amplification product by amplifying a target nucleotide by using the nucleotide primer set; and measuring and comparing amounts of a wild-type amplification product and a variant amplification product contained in the amplification product.

Another aspect of the invention provides Wild-type and variant nucleotide probes used for detecting a genotype of a single-nucleotide polymorphism G590A of a NAT2 gene from an amplification product obtained by amplification of a target nucleotide by using a nucleotide primer set.

In an aspect, wild-type nucleotide probe is complementary to wild-type amplification product and has a Tm value of 62 to 70° C., while variant nucleotide probe is complementary to variant amplification product and has a Tm value of 61 to 69° C., and the single-nucleotide polymorphism G590A site is located three bases or more inside from the terminal of respective nucleotide probes. In another aspect, wild-type nucleotide probe has a Tm value of 59 to 68° C. and variant nucleotide probe has a Tm value of 58 to 68° C., and the single-nucleotide polymorphism G857A site is located three bases or more inside from the terminal of respective nucleotide probes. In a further aspect, wild-type nucleotide probe has a Tm value of 61 to 69° C. and variant nucleotide probe has a Tm value of 58 to 70° C., and the single-nucleotide polymorphism T341C site is located 3 bases or more inside from the terminal of respective nucleotide probes.

Another aspect of the invention provides a method of detecting the genotype of the single-nucleotide polymorphisms G590A, G857A and T341C of a NAT2 gene simultaneously.

The present invention provides a nucleotide primer and a detection probe for detecting the genotype of the single-nucleotide polymorphism of a NAT2 gene. It is thus possible to detect the genotype at the single-nucleotide polymorphism sites of T341C, G590A, and G857A of NAT2 gene easily and cost-effectively.

Representative embodiments include the following:

1. A nucleotide primer set for LAMP amplification, used for detecting a genotype of a NAT2 gene single-nucleotide polymorphism G590A, wherein when a target nucleotide has F3 region, F2 region and F1 region in turn from a 5' terminal and B3c region, B2c region and B1c region in turn from a 3' terminal, and when there are nucleotide primers including an FIP primer having a sequence identical with that of the F2 region in the 3' terminal side and a sequence complementary to the F1 region in the 5' terminal side, an F3 primer having a sequence identical with that of the F3 region, a BIP primer having a sequence complementary to the B2c region in the 3' terminal side and a sequence identical with that of the B1c region in the 5' terminal side, and a B3 primer having a sequence complementary to the B3c region, the primer set comprises:

an FIP primer and a BIP primer selected from the primer sets 1 to 16 shown in Tables 2 and 3;

an F3 primer binding to a region within 60 bases from the 5' terminal of the F2 region of the target nucleotide; and a B3 primer binding to a region within 60 bases from the 3' terminal of the B2c region of the target nucleotide.

2. The nucleotide primer set according to embodiment 1, wherein the FIP primer and the BIP primer are selected from the primer sets 3, 4, and 9 shown in Tables 2 and 3.

3. The nucleotide primer set according to embodiment 1, wherein the FIP primer and the BIP primer are a primer of the primer set 9 shown in Table 3.

4. A method of detecting a genotype of single-nucleotide polymorphism G590A of a NAT2 gene, comprising the steps of:

obtaining an amplification product by amplification of a target nucleotide by using the nucleotide primer set according to embodiment 1; and measuring and comparing amounts of a wild-type amplification product and a variant amplification product contained in the amplification product.

5. The method according to embodiment 4, wherein the amplification product is measured by hybridization of nucleotide probes immobilized on a support with the amplification product and subsequent determination of an amounts of the amplification product bound to the nucleotide probe, and the nucleotide probes include a wild-type nucleotide probe complementary to the wild-type amplification product and a variant nucleotide probe complementary to the variant amplification product.

6. The method according to embodiment 5, wherein the wild-type nucleotide probe has a Tm value of 62 to 70° C., the variant nucleotide probe has a Tm value of 61 to 69° C., and the single-nucleotide polymorphism G590A site is located three bases or more inside from the terminal of the respective nucleotide probes.

7. The method according to embodiment 6, wherein the wild-type nucleotide probe has a Tm value of 62 to 66° C. and the variant nucleotide probe has a Tm value of 66 to 67° C.

8. The method according to embodiment 5, wherein the wild-type nucleotide probe has a sequence of SEQ ID No. 53 or 54 or a sequence complementary thereto, and the variant nucleotide probe has a sequence of SEQ ID No. 59 or a sequence complementary thereto.

9. The method according to embodiment 8, wherein the wild-type nucleotide probe has a sequence of SEQ ID No. 54 or a sequence complementary thereto, and the variant nucleotide probe has a sequence of SEQ ID No. 59 or a sequence complementary thereto.

10. Wild-type and variant nucleotide probes for detecting a genotype of a single-nucleotide polymorphism G590A of a NAT2 gene from an amplification product obtained by amplification of a target nucleotide by using a nucleotide primer set, wherein:

the wild-type nucleotide probe is complementary to a wild-type amplification product and has a Tm value of 62 to 70° C., and the single-nucleotide polymorphism G590A site is located three bases or more inside from the terminal thereof, and the variant nucleotide probe is complementary to a variant amplification product and has a Tm value of 61 to 69° C., and the single-nucleotide polymorphism G590A site is located three bases or more inside from the terminal thereof;

when the target nucleotide has F3 region, F2 region and F1 region in turn from a 5' terminal and B3c region, B2c region and B1c region in turn from a 3' terminal, when the nucleotide primer set includes an FIP primer having a sequence identical with that of the F2 region in the 3' terminal side and a sequence complementary to the F1 region in the 5' terminal side, an F3 primer having a sequence identical with that of the F3 region, a BIP primer having a sequence complementary to the B2c region in the 3' terminal side and a sequence identical with that of the B1c region in the 5' terminal side, and a B3 primer having a sequence complementary to the B3c region, the FIP primer and a BIP primer are selected from the primer sets 1 to 16 shown in Tables 2 and 3;

the F3 primer binds to a region within 60 bases from the 5' terminal of the F2 region of the target nucleotide; and the B3 primer binds to a region within 60 bases from the 3' terminal of the B2c region of the target nucleotide.

11. The wild-type and variant nucleotide probes according to embodiment 10, wherein the wild-type nucleotide probe has a sequence of SEQ ID No. 53 or 54 or a sequence complementary thereto, and the variant nucleotide probe has a sequence of SEQ ID No. 59 or a sequence complementary thereto.

12. The wild-type and variant nucleotide probes according to embodiment 10, wherein the probes are immobilized on a support.

13. A nucleotide primer set for LAMP amplification, used for detecting a genotype of a single-nucleotide polymorphism G857A of a NAT2 gene, wherein when a target nucleotide has F3 region, F2 region and F1 region in turn from a 5' terminal and B3c region, B2c region and B1c region in turn from a 3' terminal, and when there are nucleotide primers including an FIP primer having a sequence identical with that of the F2 region in the 3' terminal side and a sequence complementary to the F1 region in the 5' terminal side, an F3 primer having a sequence identical with that of the F3 region, a BIP primer having a sequence complementary to the B2c region in the 3' terminal side and a sequence identical with that of the B1c region in the 5' terminal side, and a B3 primer having a sequence complementary to the B3c region, the primer set comprises:

an FIP primer and a BIP primer selected from the primer sets 1 to 5 shown in Table 4;

an F3 primer binding to a region within 60 bases from the 5' terminal of the F2 region of the target nucleotide; and a B3 primer binding to a region within 60 bases from the 3' terminal of the B2c region of the target nucleotide.

14. The nucleotide primer set according to embodiment 13, wherein the FIP primer and the BIP primer are primers of the primer set 5 shown in Table 4.

15. A method of detecting a genotype of a single-nucleotide polymorphism G857A of a NAT2 gene, comprising the steps of:

obtaining an amplification product by amplifying a target nucleotide by using the nucleotide primer set according to embodiment 13; and measuring and comparing amounts of a wild-type amplification product and a variant amplification product contained in the amplification product.

16. The method according to embodiment 15, wherein the amplification product is measured by hybridization of nucleotide probes immobilized on a support with the amplification product and subsequent determination of an amount of the amplification product bound to the nucleotide probe, and the nucleotide probes include a wild-type nucleotide probe complementary to the wild-type amplification product and a variant nucleotide probe complementary to the variant amplification product.

17. The method according to embodiment 16, wherein the wild-type nucleotide probe has a Tm value of 59 to 68° C., the variant nucleotide probe has a Tm value of 58 to 68° C., and the single-nucleotide polymorphism G857A site is located three bases or more inside from the terminal of the respective nucleotide probes.

18. The method according to embodiment 17, wherein the wild-type nucleotide probe has a Tm value of 64 to 65° C., and the variant nucleotide probe has a Tm value of 64 to 66° C.

19. The method according to embodiment 18, wherein the wild-type nucleotide probe has a sequence of SEQ ID No. 62, 63 or 64 or a sequence complementary thereto, and the variant nucleotide probe has a sequence of SEQ ID No. 67, 68 or 69 or a sequence complementary thereto.

20. The method according to embodiment 19, wherein the wild-type nucleotide probe has a sequence of SEQ ID No. 62 or a sequence complementary thereto, and the variant nucleotide probe has a sequence of SEQ ID No. 67 or a sequence complementary thereto.

21. Wild-type and variant nucleotide probes for detecting a genotype of a single-nucleotide polymorphism G857A of a NAT2 gene from an amplification product obtained by amplification of a target nucleotide by using a nucleotide primer set, wherein:

the wild-type nucleotide probe is complementary to a wild-type amplification product and has a Tm value of 59 to 68° C., and the single-nucleotide polymorphism G857A site is located three bases or more inside from the terminal thereof, and the variant nucleotide probe is complementary to a variant amplification product and has a Tm value of 58 to 68° C., and the single-nucleotide polymorphism G857A site is located three bases or more inside from the terminal thereof;

when the target nucleotide has F3 region, F2 region and F1 region in turn from a 5' terminal and B3c region, B2c region and B1c region in turn from a 3' terminal, when the nucleotide primer set includes an FIP primer having a sequence identical with that of the F2 region in the 3' terminal side and a sequence complementary to the F1 region in the 5' terminal side, an F3 primer having a sequence identical with that of the F3 region, a BIP primer having a sequence complementary to the B2c region in the 3' terminal side and a sequence identical with that of the B1c region in the 5' terminal side, and a B3 primer having a sequence complementary to the B3c region, the FIP primer and a BIP primer are selected from the primer sets 1 to 5 shown in Table 4;

the F3 primer binds to a region within 60 bases from the 5' terminal of the F2 region of the target nucleotide; and the B3 primer binds to a region within 60 bases from the 3' terminal of the B2c region of the target nucleotide.

22. The wild-type and variant nucleotide probes according to embodiment 21, wherein the wild-type nucleotide probe has a sequence of SEQ ID No. 62, 63 or 64 or a sequence complementary thereto, and the variant nucleotide probe has a sequence of SEQ ID No. 67, 68 or 69 or a sequence complementary thereto.

23. The wild-type and variant nucleotide probes according to embodiment 21, wherein the probes are immobilized on a support.

24. A nucleotide primer set for LAMP amplification, used for detecting a genotype of a single-nucleotide polymorphism T341C of a NAT2 gene, wherein when a target nucleotide has F3 region, F2 region and F1 region in turn from a 5' terminal and B3c region, B2c region and B1c region in turn from a 3' terminal, and when there are nucleotide primers including an FIP primer having a sequence identical with that of the F2 region in the 3' terminal side and a sequence complementary to the F1 region in the 5' terminal side, an F3 primer having a sequence identical with that of the F3 region, a BIP primer having a sequence complementary to the B2c region in the 3' terminal side and a sequence identical with that of the B1c region in the 5' terminal side, and a B3 primer having a sequence complementary to the B3c region, the primer set comprises:

an FIP primer and a BIP primer selected from the primer sets 1 to 10 shown in Table 5;

an F3 primer binding to a region within 60 bases from the 5' terminal of the F2 region of the target nucleotide; and a B3 primer binding to a region within 60 bases from the 3' terminal of the B2c region of the target nucleotide.

25. The nucleotide primer set according to embodiment 24, wherein the FIP primer and the BIP primer are selected from the primer sets 3, 6, 9, and 10 shown in Table 5.

26. The nucleotide primer set according to embodiment 24, wherein the FIP primer and the BIP primer are primers of the primer set 6 or 10 shown in Table 5.

27. A method of detecting a genotype of a single-nucleotide polymorphism T341C of a NAT2 gene, comprising the steps of:

obtaining an amplification product by amplifying a target nucleotide by using the nucleotide primer set according to embodiment 24; and measuring and comparing amounts of a wild-type amplification product and a variant amplification product contained in the amplification product.

28. The method according to embodiment 27, wherein the amplification product is measured by hybridization of nucleotide probes immobilized on a support with the amplification product and subsequent determination of an amounts of the amplification product bound to the nucleotide probe, and the nucleotide probes include a wild-type nucleotide probe complementary to the wild-type amplification product and a variant nucleotide probe complementary to the variant amplification product.

29. The method according to embodiment 28, wherein the wild-type nucleotide probe has a Tm value of 61 to 69° C., the variant nucleotide probe has a Tm value of 58 to 70° C., and the single-nucleotide polymorphism site T341C is located three bases or more inside from the terminal of the respective nucleotide probes.

30. The method according to embodiment 29, wherein the wild-type nucleotide probe has a Tm value of 66 to 68° C., and the variant nucleotide probe has a Tm value of 63 to 69° C.

31. The method according to embodiment 30, wherein the wild-type nucleotide probe has a sequence of SEQ ID No. 72 or 73 or a sequence complementary thereto, and the variant nucleotide probe has a sequence of SEQ ID No. 76, 77 or 78 or a sequence complementary thereto.

32. The method according to embodiment 31, wherein the wild-type nucleotide probe has a sequence of SEQ ID No. 72 or a sequence complementary thereto, and the variant nucleotide probe has a sequence of SEQ ID No. 76 or a sequence complementary thereto.

33. Wild-type and variant nucleotide probes for detecting a genotype of a single-nucleotide polymorphism T341C of a NAT2 gene from an amplification product obtained by amplification of a target nucleotide by using a nucleotide primer set, wherein:

the wild-type nucleotide probe is complementary to a wild-type amplification product and has a Tm value of 61 to 69° C., and the single-nucleotide polymorphism T341C site is located three bases or more inside from the terminal thereof, and the variant nucleotide probe is complementary to a variant amplification product and has a Tm value of 58 to 70°C., and the single-nucleotide polymorphism T341C site is located three bases or more inside from the terminal thereof;

when the target nucleotide has F3 region, F2 region and F1 region in turn from a 5' terminal and B3c region, B2c region and B1c region in turn from a 3' terminal, when the nucleotide primer set included an FIP primer having a sequence identical with that of the F2 region in the 3' terminal side and a sequence complementary to the F1 region in the 5' terminal side, an F3 primer having a sequence identical with that of the F3 region, a BIP primer having a sequence complementary to the B2c region in the 3' terminal side and a sequence identical with that of the B1c region in the 5' terminal side, and a B3 primer having a sequence complementary to the B3c region, the FIP primer and a BIP primer are selected from the primer sets 1 to 10 shown in Table 5;

the F3 primer binds to a region within 60 bases from the 5' terminal of the F2 region of the target nucleotide; and the B3 primer binds to a region within 60 bases from the 3' terminal of the B2c region of the target nucleotide.

34. The wild-type and variant nucleotide probes according to embodiment 33, wherein the wild-type nucleotide probe has a sequence of SEQ ID No. 72 or 73 or a sequence complementary thereto, and the variant nucleotide probe has a sequence of SEQ ID No 76, 77 or 78 or a sequence complementary thereto.

35. The wild-type and variant nucleotide probes according to embodiment 33, wherein the probes immobilized on a support.

36. A nucleotide primer set for LAMP amplification, used for detecting genotypes of NAT2 gene single-nucleotide polymorphisms G590A and G857A, wherein when a target nucleotide has F3 region, F2 region and F1 region in turn from a 5' terminal and B3c region, B2c region and B1c region in turn from a 3' terminal, and when there are nucleotide primers including an FIP primer having a sequence identical with that of the F2 region in the 3' terminal side and a sequence complementary to the F1 region in the 5' terminal side, an F3 primer having a sequence identical with that of the F3 region, a BIP primer having a sequence complementary to the B2c region in the 3' terminal side and a sequence identical with that of the B1c region in the 5' terminal side, and a B3 primer having a sequence complementary to the B3c region, the primer set comprises:

an FTP primer and a BIP primer selected from the primer sets 1 to 8 shown in Table 6;

an F3 primer binding to a region within 60 bases from the 5' terminal of the F2 region of the target nucleotide; and a B3 primer binding to a region within 60 bases from the 3' terminal of the B2c region of the target nucleotide.

37. The nucleotide primer set according to embodiment 36, wherein the FIP primer and the BIP primer are selected from the primer sets 1, 6, 7, and 8 shown in Table 6.

38. The nucleotide primer set according to embodiment 36, wherein the FIP primer and the BIP primer are a primer of the primer set 6 shown in Table 6.

39. A method of detecting genotypes of single-nucleotide polymorphisms G590A and G857A of a NAT2 gene, comprising the steps of:

obtaining an amplification product by amplifying a target nucleotide by using the nucleotide primer set according to embodiment 36; and measuring and comparing amounts of a wild-type amplification product and a variant amplification product contained in the amplification product.

40. The method according to embodiment 39, wherein the amplification product is measured by hybridization of nucleotide probe immobilized on a support with the amplification product and subsequent determination of amounts of the amplification product bound to the nucleotide probe, and the nucleotide probes include a wild-type nucleotide probe complementary to the wild-type amplification product and a variant nucleotide probe complementary to the variant amplification product.

41. The method according to embodiment 40, wherein the wild-type nucleotide probes include a wild-type nucleotide probe for G590A having a sequence of SEQ ID No. 54 or a sequence complementary thereto and a wild-type nucleotide probe for G857A having a sequence of SEQ ID No. 62 or a sequence complementary thereto, and the variant nucleotide probes include a variant nucleotide probe for G590A having a sequence of SEQ ID No. 59 or a sequence complementary thereto and a variant nucleotide probe for G857A having a sequence of SEQ ID No. 67 or a sequence complementary thereto.

42. A method of detecting genotypes of single-nucleotide polymorphisms G590A, G857A and T341C of a NAT2 gene simultaneously, comprising the steps of:

obtaining an amplification product by amplifying a target nucleotide by using the primer set 9 shown in Table 3;

obtaining an amplification product by amplifying a target nucleotide by using the primer set 5 shown in Table 4;

obtaining an amplification product by amplifying a target nucleotide by using the primer set 6 or 10 shown in Table 5;

mixing the amplification products to prepare a liquid mixture;

hybridizing the amplification products to the nucleotide probes by bringing the liquid mixture into contact with a nucleotide probe-immobilized support carrying a wild-type nucleotide probe for G590A having a sequence of SEQ ID No. 54 or a sequence complementary thereto, a variant nucleotide probe for G590A having a sequence of SEQ ID No. 59 or a sequence complementary thereto, a wild-type nucleotide probe for G857A having a sequence of SEQ ID No. 62 or a sequence complementary thereto, a variant nucleotide probe for G857A having a sequence of SEQ ID No. 67 or a sequence complementary thereto, a wild-type nucleotide probe for T341C having a sequence of SEQ ID No. 72 or a sequence complementary thereto, and a variant nucleotide probe for T341C having a sequence of SEQ ID No. 76 or a sequence complementary thereto immobilized thereon;

measuring amounts of the amplification product bound to the respective nucleotide probes;

comparing amounts of the amplification product bound respectively to the wild-type nucleotide probe for G590A and the variant nucleotide probe for G590A;

comparing amounts of the amplification products bound respectively to the wild-type nucleotide probe for G857A and the variant nucleotide probe for G857A; and comparing amounts of the amplification products bound respectively to the wild-type nucleotide probe for T341C and the variant nucleotide probe for T341C.

BRIEF DESCRIPTION OF THE SEVERAL VIEWS OF THE DRAWING

FIG. 1 is a schematic diagram showing the LAMP method;

FIG. 5 is a schematic diagram showing the detection position of amplification products;

FIG. 9A shows the sequence of NAT1 and NAT2 genes; where NAT1.prj is depicted by SEQ ID NO: 81 and NAT2.prj by SEQ ID NO: 82;

FIG. 9B shows the sequence of NAT1 and NAT2 genes following that shown in FIG. 9A; where NAT1.prj is depicted by SEQ ID NO: 81 and NAT2.prj by SEQ ID NO: 82;

FIG. 10 shows electrophoretograms of the amplification products obtained by using the primer set;

FIG. 12 shows an electrophoretogram of the amplification products including non-specific amplification product;

FIG. 15A shows graphs indicating the test result 3 (wild-type) obtained by using the probe for detection of G590A;

FIG. 16A shows graphs indicating the test result 1 (primer set 1) obtained by using the probe for detection of G857A;

FIG. 18A shows graphs indicating the test result 1 (primer set 6) obtained by using the probe for detection of T341C;

FIG. 20A shows graphs indicating the results of simultaneous detection of G590A, G857A, and T341A (primer set 6 for T341C)

DETAILED DESCRIPTION OF THE INVENTION

Figure 2:
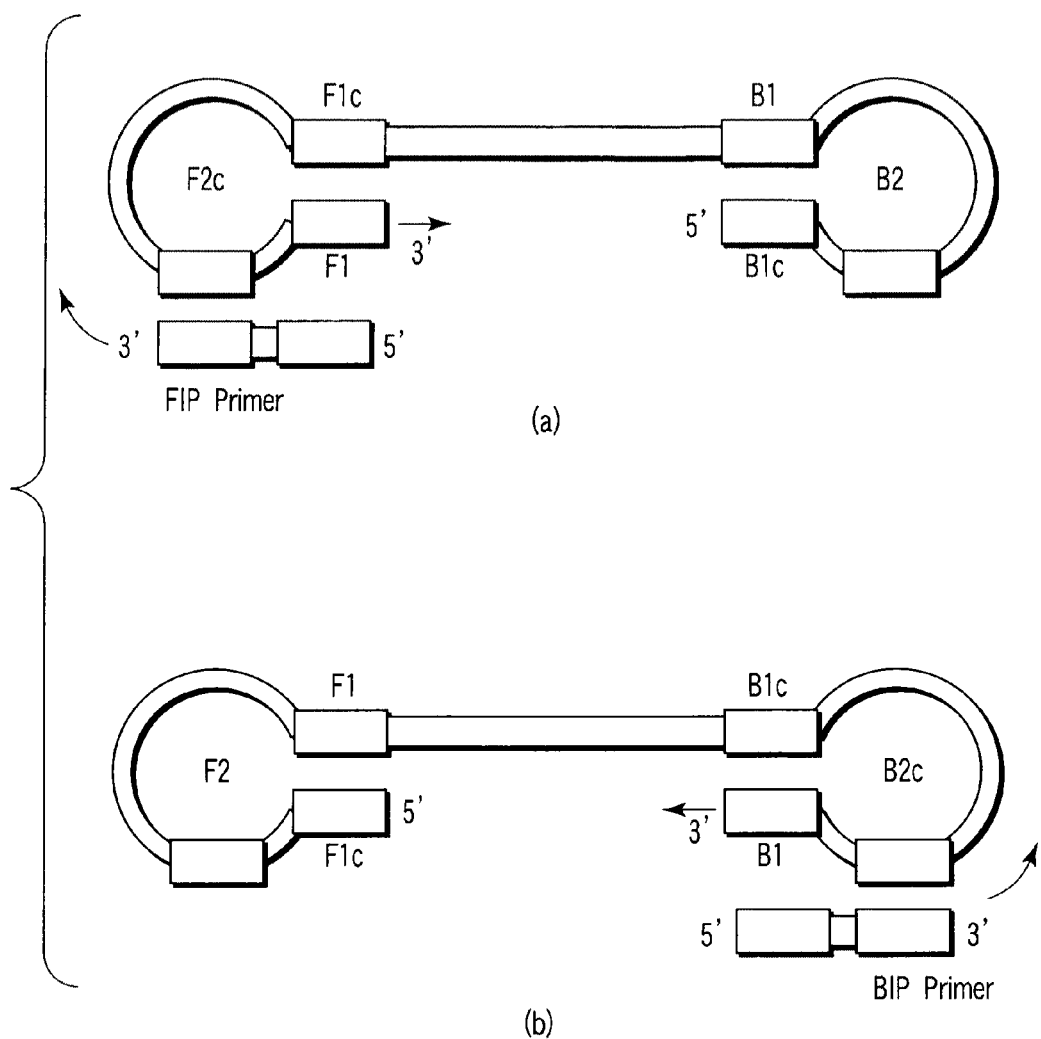
FIG. 2 is a schematic chart showing an intermediate product and the annealing site of an inner primer (FIP or BIP) by the LAMP method.

The PCR method has been frequently used for detection of a single-nucleotide polymorphism, but the PCR method has the disadvantages described above. Thus in the present invention, the single-nucleotide polymorphism is detected by the loop-mediated isothermal amplification (LAMP) method, replacing the PCR method. In the LAMP method, a nucleotide is amplified under an isothermal condition at 60 to 65° C. The LAMP method has the advantage that it is possible to obtain amplification products in a shorter period in a greater amount than the PCR method. It is also reported that the reaction is less influenced by impurities in a sample. It is therefore possible to amplify a target nucleotide easily by the LAMP method.

In an embodiment of the present invention, a target nucleotide is amplified by the LAMP method, and the amounts of the wild-type amplification products and variant amplification products in the amplification products obtained are respectively determined. When there are many wild-type amplification products, the genotype of the tested target nucleotide can be judged as a wild-type homo. On the contrary, when there are many variant amplification products, the target nucleotide can be judged as a variant homo. Alternatively, when there are almost the same amounts of the wild-type and variant amplification products, the target nucleotide can be judged as a heterozygous.

The amounts of the amplification products are determined, for example, by using a nucleotide probe. The nucleotide probes include one complementary to wild-type amplification products and one complementary to variant amplification products. Amplification products and the respective nucleotide probes are allowed to hybridize to each other, and the amounts of the amplification products bound to respective nucleotide probes are determined. It is possible to determine the genotype of the target nucleotide by comparing the amounts of the amplification products bound to a wild-type nucleotide probe and the amounts of the amplification products bound to a variant nucleotide probe.

<Summary of LAMP Method>

Hereinafter, the LAMP method will be described briefly. In the present specification, the nucleotide (including genomic DNA or the like) subjected to detection of a single-nucleotide polymorphism will be called analyte nucleotide. The region in the NAT2 gene amplified by the LAMP method will be called a target nucleotide. The products obtained by the LAMP method will be called amplification products. The solution containing human genomic DNA will be called a sample solution.

In the LAMP method, the target nucleotide is designed to have F3 region, F2 region, and F1 region in turn from the 5' terminal and B3c region, B2c region, and B1c region in turn from the 3' terminal. The target nucleotides are amplified by using the four kinds of primers shown in FIG. 1. The regions F1c, F2c, F3c, B1, B2, and B3 are regions of the complementary chains respectively corresponding to the regions F1, F2, F3, B1c, B2c, and B3c.

The four kinds of primer used for amplification of the nucleotide in the LAMP method are (1) FIP primer having the sequence identical with the F2 region in the 3' terminal side and the sequence complementary to the F1 region in the 5' terminal side; (2) F3 primer having the sequence identical with the F3 region; (3) BIP primer having the sequence complementary to the B2c region in the 3' terminal side and the sequence identical with the B1c region in the 5' terminal side; and (4) B3 primer having the sequence complementary to the B3c region. Generally, FIP and BIP primers are called inner primers, while F3 and B3 primers are called outer primers.

LAMP amplification by using the four kinds of primers gives intermediate products having the dumbbell structure shown in FIG. 2. FIP and BIP primers bind to F2c region and B2c region in single-stranded loops, and extending reaction proceeds from the 3' terminal of the each primer and the 3' terminal of the intermediate product itself. See Japanese Patent No. 3313358 for details.

Figure 3:
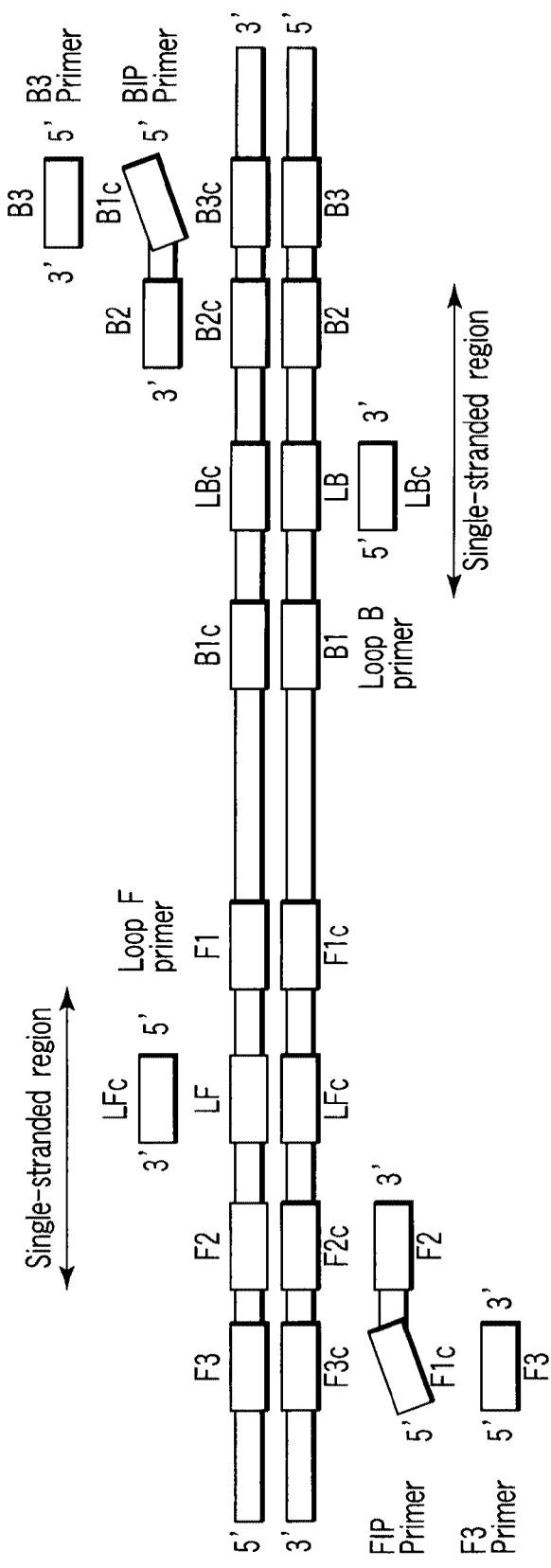
FIG. 3 is a schematic diagram showing the location of loop primers.
Figure 4:
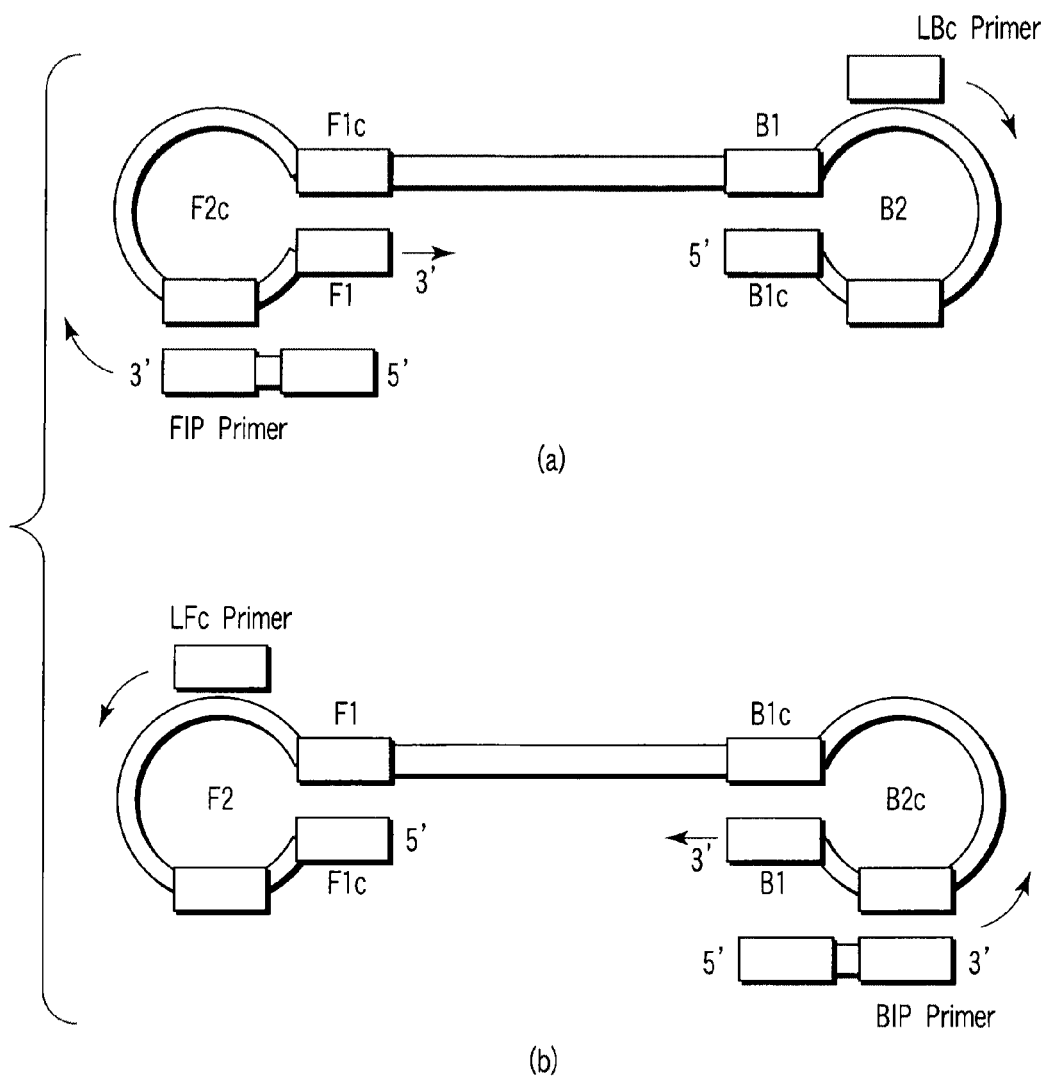
FIG. 4 is a schematic chart showing an intermediate product and the annealing site of a loop primer (LFc or LBc) by the LAMP method.

It is possible to shorten the amplification period by using a primer, called a loop primer, optionally in the LAMP method. In such a case, as shown in FIG. 3, a LF region is designed in the region from F2 region to F1 region and a LBc region is designed in the region from B2c region to B1c region. These regions are called loop primer region. In addition to the four kinds of primers, a loop primer LFc having the sequence complementary to the LF region and a loop primer LBc having the sequence identical with the LBc region are used. See WO2002/024902 for details. These loop primers LFc and LBc may be used simultaneously, or alternatively, only one of them may be used. The loop primers are annealed to a loop different from the loop to which FIT and BIP primers are annealed, as shown in FIG. 4, giving additional synthetic origins and thus accelerating amplification.

<Detection of LAMP Amplification Products; Nucleotide Probe>

For detection of a single-nucleotide polymorphism, the polymorphic site to be detected is located in the FP region or BPc region shown in FIG. 5. Alternatively, different polymorphisms may be located in the FP region and BPc region, respectively. As shown in FIG. 5, the region from F2 region to F1 region is a part that becomes single stranded in the amplification product. Similarly, the region from B2c region to B1c region is also a part that becomes single-stranded in the amplification product. It is possible to make the detection by nucleotide probe easier, by locating the polymorphic site to be detected in a single-stranded part.

The nucleotide probe is designed to bind to the FP region or BPc region containing the polymorphic site. Thus, the nucleotide probe has a sequence complementary to that of the region containing the polymorphic site among FP region or BPc region.

FPc region complementary to FP region and BP region complementary to BPc region is also present in the amplification products. Accordingly, it is possible to use the FPc region and BP region for detection.

In the present specification, nucleotide probes containing sequences complementary to that of wild-type amplification products are called wild-type nucleotide probes, while the nucleotide probes containing the sequences complementary to that of variant amplification products are called variant nucleotide probes.

The nucleotide probe may be consisted of, but is not limited to, DNA, RNA, PNA, LNA, a nucleotide having a methyl phosphonate skeleton, or other synthetic nucleotide chain. For immobilization on a support, the terminal thereof may be modified with a reactive functional group such as amino, carboxyl, hydroxyl, thiol, or sulfonyl group. A spacer may be introduced between the functional group and the nucleotide. The spacer may have, for example, an alkane skeleton, an ethylene glycol skeleton, or the like.

<Nucleotide Probe-Immobilized Support>

The nucleotide probe may be used, for example, as it is immobilized on a support. The nucleotide probe-immobilized support may be used in a known apparatus such as a so-called DNA chip and DNA microarray.

Figure 6:
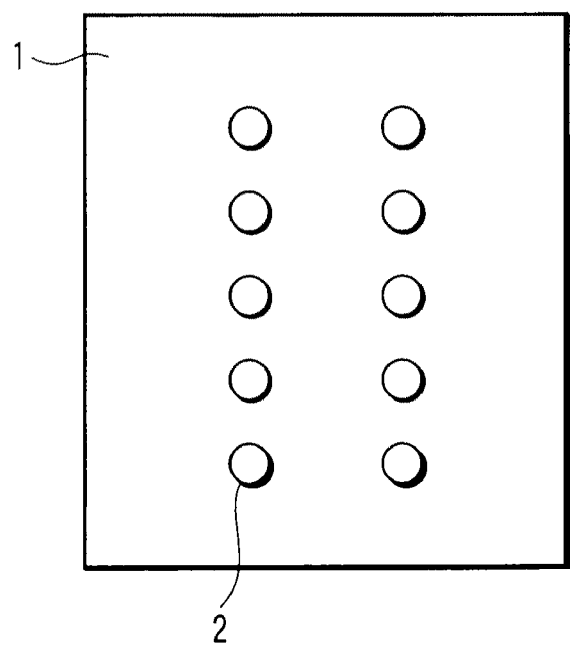
FIG. 6 is a schematic planar view of an embodiment of a probe-immobilized support.

An embodiment of the probe-immobilized support is shown in FIG. 6. The probe is immobilized in an immobilization area 2 of a support 1. The support 1 may be prepared with a silicon substrate, but is not limited thereto. The probe may be immobilized by any known means. Only one kind of probe may be immobilized on a support, or different kinds of probe may be immobilized on a support, the location and the number thereof may be modified as needed by those who are skilled in the art. As will be described below, a probe-immobilized support according to the present embodiment may be used for fluorescent detection of a probe.

Figure 7:
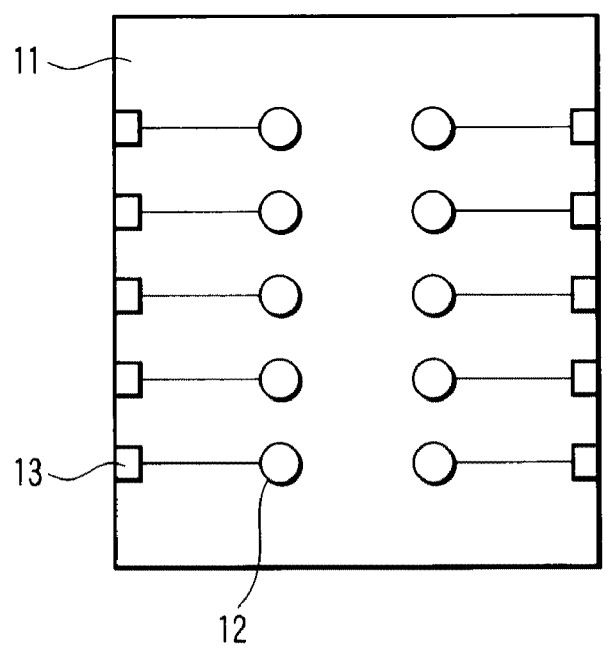
FIG. 7 is a schematic planar view of an embodiment of the probe-immobilized support.

A schematic view of the probe-immobilized support in another embodiment is shown in FIG. 7. In the present embodiment, electrodes 12 are formed on a support 11. The probe is immobilized on the electrode 12. Each electrode 12 is connected to a pad 13 for extracting electrical information. The support 11 may be prepared, for example, from a silicon substrate, but is not limited thereto. Production of electrode and immobilization of probe may be performed by any known means. The electrode can be made of any material which include, but not limited to, single metals such as gold, gold alloy, silver, platinum, mercury, nickel, palladium, silicon, germanium, gallium and tungsten, alloys thereof, carbons such as graphite and glassy carbon, and the oxides or compounds thereof.

The immobilization support shown in FIG. 7 has 10 electrodes, but the number of the electrodes formed on a single support is not limited thereto and may be modified optionally. The positional pattern of the electrodes is also not limited to that shown in the figure, and may be modified as needed by those who are skilled in the art. Reference electrodes and counter electrodes may be formed as needed on the support 1. As will be described below, a probe-immobilized support according to this embodiment may be used for electrochemical detection.

<Hybridization of Nucleotide Probe with Amplification Product>

The amplification products are hybridized to the nucleotide probe under a suitable condition. The suitable condition varies according to the kind and structure of the amplification products, the kind of nucleotide contained in the sequence to be detected, and the kind of nucleotide probe. Specifically, the hybridization is performed in a buffer solution at an ionic strength in the range of 0.01 to 5 and at a pH in the range of 5 to 10. Dextran sulfate, which is a hybridization accelerator, salmon sperm DNA, bovine thymic DNA, EDTA, a surfactant, and the like may be added to the reaction solution. The reaction temperature is, for example, in the range of 10 to 90° C., and the reaction mixture may be stirred or shaken to improve the reaction efficiency. After reaction, a buffer solution for example at an ionic strength in the range of 0.01 to 5 and at a pH in the range of 5 to 10 may be used for washing.

<Detection Method>

Hybridization between the probe immobilized on the support and the amplification products gives double-strand nucleotides. The double-strand nucleotides can be detected electrochemically or by fluorescence.

(a) Current Detection System

Electrochemical detection of the double-strand nucleotide will be described below. The method uses a double-stranded chain-recognizing compound that recognizes a double-strand nucleotide specifically. Examples of the double-stranded chain-recognizing compounds include, but are not limited to, Hoechst 33258, acridine orange, quinacrine, daunomycin, metallointercalators, bisintercalators such as bisacridine, trisintercalators, and polyintercalators. These substances may be modified with an electrochemically active metal complex such as ferrocene or viologen.

The concentration of the double-stranded chain-recognizing compound may vary according to its kind, but generally, it is used at a concentration range of 1 ng/mL to 1 mg/mL. In this case, a buffer solution at an ionic strength in the range of 0.001 to 5 and at a pH in the range of 5 to 10 is used preferably.

A double-stranded chain-recognizing compound is added to the reaction solution during or after a hybridization reaction. The double-stranded chain-recognizing compound binds to double-strand nucleotides, if formed by hybridization. For example, it is possible to measure the reaction current derived from the double-stranded chain-recognizing compound, by applying an electric potential higher than that causing electrochemical reaction of the double-stranded chain-recognizing compound. In this case, the electric potential may be applied at a constant velocity, or applied in a pulse shape or at a constant voltage. The current and voltage may be controlled during measurement by using a device such as a potentiostat, digital multimeter, or function generator. For example, the known electrochemical detecting means disclosed in JP-A 10-146183 (KOKAI) is used preferably.

(b) Fluorescent Detection Method

The method of detecting a double-strand nucleotide by fluorescence will be described below. The primer is previously labelled with a fluorescently active substance. Alternatively, it is detected with a secondary probe labelled with a fluorescently active substance. A secondary probe with multiple labels may be used. Examples of the fluorescently active substance include, but are not limited to, fluorescent colorants such as FITC, Cy3, Cy5, and rhodamine. The fluorescent material is detected, for example, with a fluorescence detector. A detector suitable for the kind of label is used for detection of labeled sequence to be detected or secondary probe.

<Selection of Nucleotide Primer>

Figure 8:
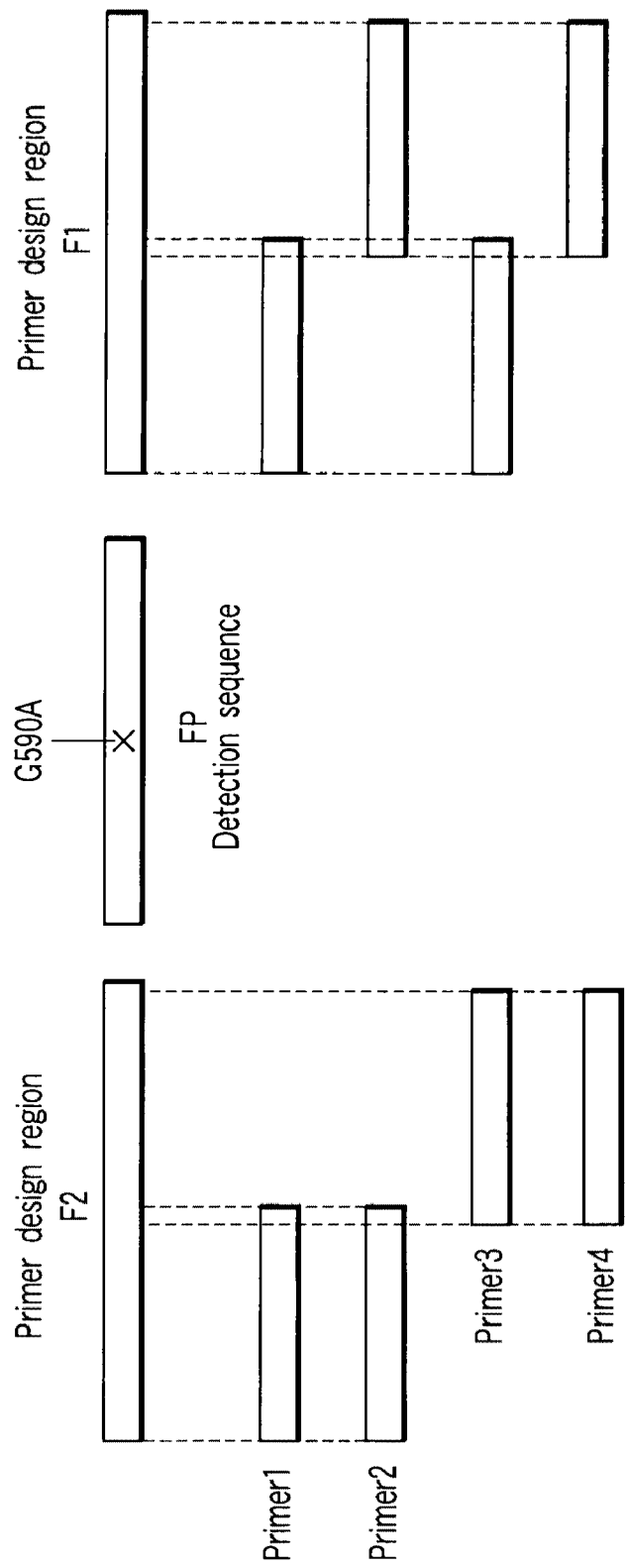
FIG. 8 is a schematic diagram showing the location of an FIP primer.

FIG. 8 is a schematic diagram showing nucleotide primers when a single-nucleotide polymorphism G590A is located in the region between F2 and F1, i.e., FP region. The FIP primer has the same sequence as the F2 region and the sequence complementary to that of the F1 region. Various kinds of primers may be designed, as long as the F2 region and F1 region is positioned at places holding G590A inside.

However, studies by the inventors have revealed that the amplification efficiency by the LAMP method varies according to the kind of primer. For example, amplification is performed by using primer one of the four kinds of primers shown in FIG. 8, and common three primers (BIP, F3, and B3 primers). As a result, the sample with primer 1 is not amplified even after a sufficient period, for example after 2 hours. The sample with primer 2 is amplified after approximately 1 hour, but non-specific amplification of primers is occurred. The sample with primer 3 does not cause non-specific amplification of primers, but requires an amplification period of 1.5 to 2 hours. The sample with primer 4 causes no non-specific amplification of primers and completes amplification within 1 hour. In this case, the primers preferable for amplification are the primers 3 and 4, and the best primer is the primer 4. Thus, it is superior primer that is higher in amplification efficiency, allows amplification in a short period of time, and causes no non-specific amplification.

For detection of amplification products with a nucleotide probe, the amplification product preferably hybridizes with the nucleotide probe at a high efficiency. Accordingly, the hybridization efficiency of the amplification products is also considered in evaluating the primer.

Human NAT2 gene is extremely highly homologous to human NAT1. The sequence of the NAT2 and NAT1 genes is shown in FIGS. 9A and 9B. It is necessary to place a primer in a region different in sequence between NAT2 and NAT1 for specific amplification of NAT2, because NAT2 and NAT1 genes are highly homologous to each other.

Accordingly, at least one primer needs to be placed in the region different in sequence between NAT2 and NAT1. Preferably, at least one of regions F1, F2, B1, and B2 need to be designed in a region which has different sequence between NAT2 and NAT1. Moreover no primer is placed in the region where mutation is reported as shown in FIG. 9. If a primer is inevitably placed at such a mutation site, a universal base such as mix base or deoxyinosine (dI) is introduced. Another inner primer having no single-nucleotide polymorphism inside is preferably placed in a region having a F2 to B2 length of 450 bp or less, more preferably 350 bp or less. In addition, both inner primers are preferably designed to make the length of the single-stranded loop 100 bp or less, more preferably 70 bp or less.

Non-specific amplification among primers is a phenomenon often found in the LAMP reaction. The FIP primer, which contains the F1c region and F2 region, is often a long-chain nucleotide. Similarly, the BIP primer, which contains the B1c region and B2 region, is often a long-chain nucleotide. Thus, among FIP primers, among BIP primers, or FIP and BIP primers may be entangled with each other, frequently allowing amplification of which template is primer. The possibility of a non-specific reaction is higher in the LAMP reaction than in the PCR reaction, because the reaction solution contains the F3 and B3 primers and additionally LFc and LBc primers in some cases. Such non-specific reaction leads to a decrease in the amount of desirable LAMP products obtained by using the analyte nucleotide as the template.

If a non-specific reaction occurs in a negative control reaction solution containing no added analyte nucleotide, it is not possible to determine whether the white precipitate of pyrophosphoric acid and Mg released along with progress of amplification is caused by non-specific amplification or by contamination. Accordingly, it is important to eliminate the primers possibly causing non-specific amplification.

Accordingly, the inventors have conducted tests for selection of the nucleotide primer most preferable for amplification of a single-nucleotide polymorphism G590A of the NAT2 gene, and also for amplification of a single-nucleotide polymorphism G857A and T341C.

[Test 1-1: Primer for G590A; FP Region]

An amplification reaction was performed at 63° C. for 1 hour or 2 hours, by using six kinds of nucleotide primer sets containing the NAT2 G590A polymorphic sites in the FP region. The composition of the reaction solution is shown in Table 1. The template DNA used was a human genome. For examination of the presence or absence of contamination and non-specific amplification, a negative control containing sterilized ultrapure water instead of the human genome was prepared in all sets. After the amplification reaction, amplification products were identified by 3% agarose electrophoresis.

The nucleotide primer sets used are shown in Table 2.

TABLE 1

| LAMP reaction composition | |
|---|---|
| Bst DNA Polymerase | 1 µL |
| 2 × Buffer | 12.5 µL |
| Tris · HCl pH 8.0 40 mM | |
| KCl 20 mM | |
| MgSO$_4$ 16 mM | |
| (NH$_4$)$_2$SO$_4$ 20 mM | |
| Tween20 0.2% | |
| Betaine 1.6M | |
| dNTP 2.8 mM | |
| F3 primer (10 µM) | 0.5 µL |
| B3 primer (10 µM) | 0.5 µL |
| FIP primer (40 µM) | 1 µL |
| BIP primer (40 µM) | 1 µL |
| LFc primer (20 µM) | 1 µL |
| Human genome (30 ng/µL) | 1 µL |
| Sterilized ultrapure water | 6.5 µL |
| Total | 25 µL |

TABLE 2

Primer set having G590A in region FP or FPc

| Primer set | SEQ ID No. | Name | Sequence | 1-hour amplification | 2-hour amplification | Non-specific amplification |
|---|---|---|---|---|---|---|
| 1 | 1 | FIP-1 | CGTCTGCAGGTATGTATTCATAGACTCAAAAAATATACTTATTTACGCTTGAACC | x | o | Not-occurred |
|  | 7 | BIP-1 | ATAACCACATCATTTTGTTCCTTGCATGAATTTTCTATAGGTGAGGATGA |  |  |  |
| 2 | 2 | FIP-2 | CGTCTGCAGGTATGTATTCATAGACTCAACACCAAAAAATATACTTATTTACGC | x | o | Not-occurred |
|  | 7 | BIP-1 | ATAACCACATCATTTTGTTCCTTGCATGAATTTTCTATAGGTGAGGATGA |  |  |  |
| 18 | 3 | FIP-3 | CGTCTGCAGGTATGTATTCATAGACTCAACAAAGAAGAAACACCAAAAAATATAC | x | x | Not-occurred |
|  | 7 | BIP-1 | ATAACCACATCATTTTGTTCCTTGCATGAATTTTCTATAGGTGAGGATGA |  |  |  |
| 19 | 4 | FIP-4 | CGTCTGCAGGTATGTATTCATAGACTCAACTCCTGCCAAAGAAGAAACACCAA | x | x | Not-occurred |
|  | 7 | BIP-1 | ATAACCACATCATTTTGTTCCTTGCATGAATTTTCTATAGGTGAGGATGA |  |  |  |
| 3 | 5 | FIP-5 | GCAGGTATGTATTCATAGACTCAAAATCTCACCAAAAAATATACTTATTTACGC | o | o | Not-occurred |
|  | 7 | BIP-1 | ATAACCACATCATTTTGTTCCTTGCATGAATTTTCTATAGGTGAGGATGA |  |  |  |
| 4 | 6 | FIP-6 | GGAGACGTCTGCAGGTATGTATTCCACCAAAAAATATACTTATTTACGC | o | o | Not-occurred |
|  | 7 | BIP-1 | ATAACCACATCATTTTGTTCCTTGCATGAATTTTCTATAGGTGAGGATGA |  |  |  |
|  | 8 | F3 | CAAACAAAGAATTTCTTAATTCTCATC |  |  |  |
|  | 9 | B3 | CGACCAGATCTGTATTGTCTT |  |  |  |

F3 primer has the sequence of SEQ ID No. 8, and B3 primer has the sequence of SEQ ID No. 9; and both primers were used commonly in all sets.

[Test 1-1: Results]

The amplification products obtained by using the six kinds of primer sets shown in Table 2 were subjected to electrophoresis. The results are summarized in FIG. 10. After amplification for 1 hour, sufficient amounts of amplification products were obtained with the primer sets 3 and 4 (lanes 5 and 6). After amplification for 2 hours, sufficient amounts of amplification products were obtained with the primer sets 1, 2, 3 and 4 (lanes 1, 2, 5 and 6). With the primer sets 18 and 19 (lanes 3 and 4), there were few amplification products, or no amplification was confirmed. No non-specific amplification was observed in any of the sets. The results above showed that the primer sets 1, 2, 3, and 4 were preferable, and that the primer sets 3 and 4 were the most preferable. The results are summarized in Table 2.

[Test 1-2: Primer for G590A; BP Region]

An amplification reaction was performed at 63° C. for 1 hour or 2 hours, by using 16 kinds of nucleotide primer sets containing the NAT2 G590A polymorphic sites in the BP region. The r composition of the reaction solution is shown in Table 1. The template DNA used was a human genome. For examination of the presence or absence of contamination and non-specific amplification, a negative control containing sterilized ultrapure water instead of the human genome was prepared in all sets. After the amplification reaction, amplification products were identified by 3% agarose electrophoresis.

The nucleotide primer sets used are shown in Table 3.

TABLE 3

Primer set having G590A in BP or BPc region

| Primer set | SEQ ID No. | Name | Sequence | 1-hour amplification | 2-hour amplification | Non-specific amplification |
|---|---|---|---|---|---|---|
| 20 | 10 | FIP-1 | GTTTGTAATATACTGCTCTCTCCTGGCTTGACAGAAGAGAGAGGAATC | x | o | Occurred |
|  | 11 | BIP-1 | GAAACACCAAAAAATATACTTATTTACGCCTGCAGGTATGTATTCATAGACTCA |  |  |  |
| 21 | 10 | FIP-1 | GTTTGTAATATACTGCTCTCTCCTGGCTTGACAGAAGAGAGAGGAATC | x | o | Occurred |
|  | 12 | BIP-2 | GAAACACCAAAAAATATACTTATTTACGCCAGGTATGTATTCATAGACTCAAAATCT |  |  |  |

TABLE 3-continued

Primer set having G590A in BP or BPc region

| Primer set | SEQ ID No. | Name | Sequence | 1-hour amplification | 2-hour amplification | Non-specific amplification |
|---|---|---|---|---|---|---|
| 5 | 10 | FIP-1 | GTTTGTAATATACTGCTCTCTCCTGGCTTGACAGAAGAGAGGAATC | x | o | Not-occurred |
|  | 13 | BIP-3 | CACCAAAAAATATACTTATTTACGCCTGCAGGTATGTATTCATAGACTC |  |  |  |
| 6 | 10 | FIP-1 | GTTTGTAATATACTGCTCTCTCCTGGCTTGACAGAAGAGAGGAATC | x | o | Not-occurred |
|  | 14 | BIP-4 | CACCAAAAAATATACTTATTTACGCCAGGTATGTATTCATAGACTCAAAATC |  |  |  |
| 7 | 15 | FIP-2 | GTTTGTAATATCTGCTCTCTCCTGCCTTGCATTTTCTGCTTGAC | x | o | Not-occurred |
|  | 11 | BIP-1 | GAAACACCAAAAAATATACTTATTTACGCCTGCAGGTATGTATTCATAGACTCA |  |  |  |
| 8 | 15 | FIP-2 | GTTTGTAATATACTGCTCTCTCCTGCCTTGCATTTTCTGCTTGAC | x | o | Not-occurred |
|  | 12 | BIP-2 | GAAACACCAAAAAATATACTTATTTACGCCAGGTATGTATTCATAGACTCAAAATCT |  |  |  |
| 9 | 15 | FIP-2 | GTTTGTAATATACTGCTCTCTCCTGCCTTGCATTTTCTGCTTGAC | o | o | Not-occurred |
|  | 13 | BIP-3 | CACCAAAAAATATACTTATTTACGCCTGCAGGTATGTATTCATAGACTC |  |  |  |
| 10 | 15 | FIP-2 | GTTTGTAATATACTGCTCTCTCCTGCCTTGCATTTTCTGCTTGAC | x | o | Not-occurred |
|  | 14 | BIP-4 | CACCAAAAAATATACTTATTTACGCCAGGTATGTATTCATAGACTCAAAATC |  |  |  |
| 11 | 16 | FIP-3 | GAAATTCTTTGTTTGTAATATACTGCGCTTGACAGAAGAGAGGAATC | x | o | Not-occurred |
|  | 11 | BIP-1 | GAAACACCAAAAAATATACTTATTTACGCCTGCAGGTATGTATTCATAGACTCA |  |  |  |
| 12 | 16 | FIP-3 | GAAATTCTTTGTTTGTAATATACTGCGCTTGACAGAAGAGAGGAATC | x | o | Not-occurred |
|  | 12 | BIP-2 | GAAACACCAAAAAATATACTTATTTACGCCAGGTATGTATTCATAGACTCAAAATCT |  |  |  |
| 13 | 16 | FIP-3 | GAAATTCTTTGTTTGTAATATACTGCGCTTGACAGAAGAGAGGAATC | x | o | Not-occurred |
|  | 13 | BIP-3 | CACCAAAAAATATACTTATTTACGCCTGCAGGTATGTATTCATAGACTC |  |  |  |
| 14 | 16 | FIP-3 | GAAATTCTTTGTTTGTAATATACTGCGCTTGACAGAAGAGAGGAATC | x | o | Not-occurred |
|  | 14 | BIP-4 | CACCAAAAAATATACTTATTTACGCCAGGTATGTATTCATAGACTCAAAATC |  |  |  |
| 22 | 17 | FIP-4 | GAAATTCTTTGTTTGTAATATACTGCCCTTGCATTTTCTGCTTGAC | x | x | Not-occurred |
|  | 11 | BIP-1 | GAAACACCAAAAAATATACTTATTTACGCCTGCAGGTATGTATTCATAGACTCA |  |  |  |
| 23 | 17 | FIP-4 | GAAATTCTTTGTTTGTAATATACTGCCCTTGCATTTTCTGCTTGAC | x | x | Not-occurred |
|  | 12 | BIP-2 | GAAACACCAAAAAATATACTTATTTACGCCAGGTATGTATTCATAGACTCAAAATCT |  |  |  |
| 15 | 17 | FIP-4 | GAAATTCTTTGTTTGTAATATACTGCCCTTGCATTTTCTGCTTGAC | x | o | Not-occurred |
|  | 13 | BIP-3 | CACCAAAAAATATACTTATTTACGCCTGCAGGTATGTATTCATAGACTC |  |  |  |
| 16 | 17 | FIP-4 | GAAATTCTTTGTTTGTAATATACTGCCCTTGCATTTTCTGCTTGAC | x | o |  |
|  | 14 | BIP-4 | CACCAAAAAATATACTTATTTACGCCAGGTATGTATTCATAGACTCAAAATC |  |  |  |
|  | 18 | F3 | CTGGGAAGGATCAGCCTC |  |  |  |
|  | 19 | B3 | AAATGAAGATGTTGGAGACG |  |  |  |

F3 primer has the sequence of SEQ ID No. 18, and B3 primer has the sequence of SEQ ID No. 19; and both primers were used commonly in all sets.

[Test 1-2: Results]

Figure 11:
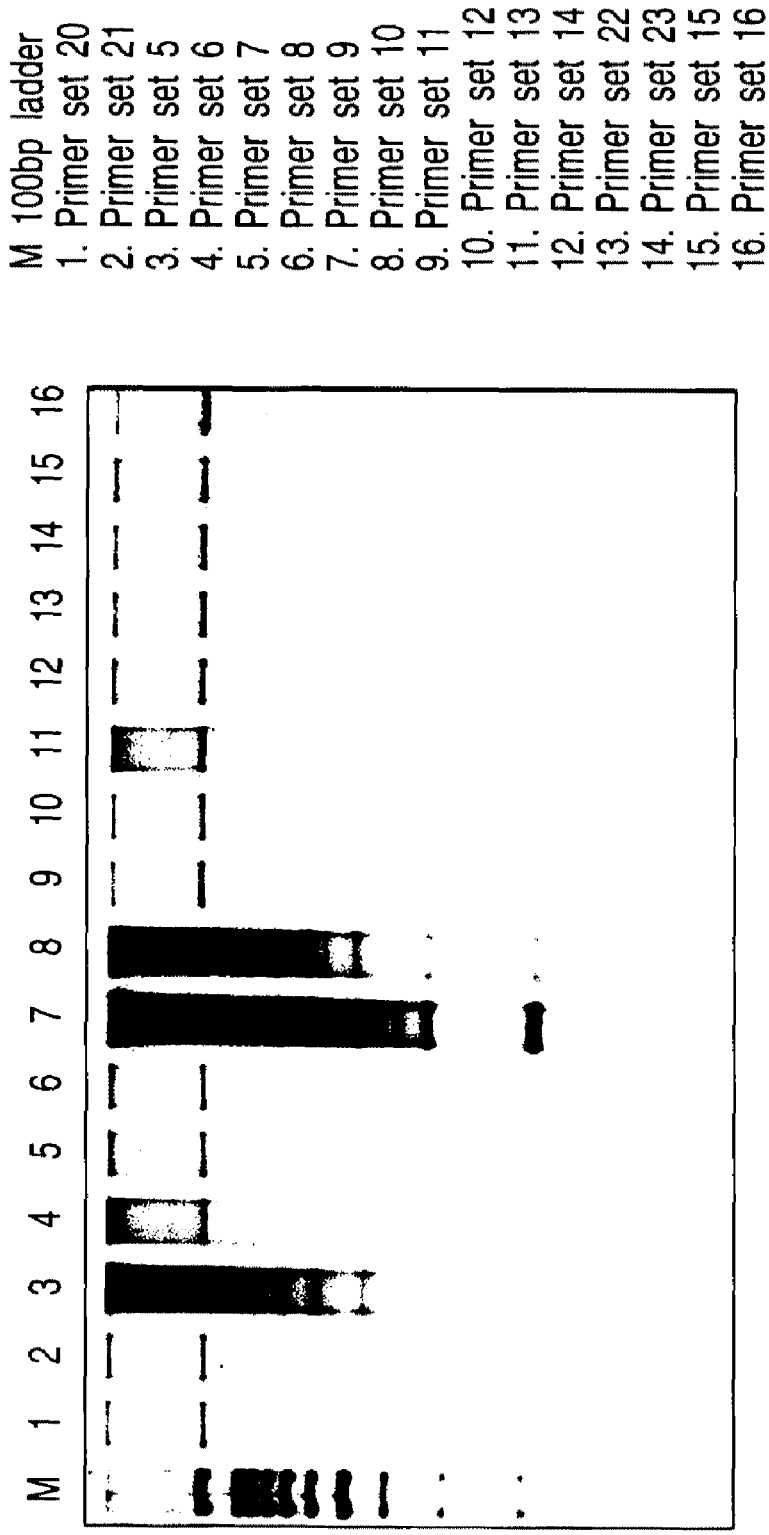
FIG. 11 shows another electrophoretogram of the amplification products obtained by using the primer set.

The amplification product obtained by using the 16 kinds of primer sets shown in Table 3 were subjected to electrophoresis. The results are summarized in FIG. 11. After amplification for 1 hour, the primer set 9 gave sufficient amounts of amplification products (lane 7). After amplification for 2 hours, the primer sets 5, 6, 7, 8, 9, 10, 11, 12, 13, 14, 15, 20, and 21 gave sufficient amounts of amplification products. There was no amplification with the primer sets 22 and 23. Non-specific amplification was occurred with the primer sets 20 and 21 as shown in FIG. 12. The results above showed that the primer sets 5, 6, 7, 8, 9, 10, 11, 12, 13, 14, 15 and 16 were preferable, and that the primer set 9 was the most preferable. The results are summarized in Table 3.

[Test 2: Primer for G857A; BP Region]

An amplification reaction was performed at 63° C. for 1 hour or 2 hours, by using six kinds of nucleotide primer sets containing the NAT2 G857A polymorphic sites in the BP region. The composition of the reaction solution is shown in Table 1. The template DNA used was a human genome. For examination of the presence or absence of contamination and non-specific amplification, a negative control containing sterilized ultrapure water instead of the human genome was prepared in all sets. After the amplification reaction, amplification products were identified by 3% agarose electrophoresis.

The nucleotide primer sets used are shown in Table 4.

F3 primer has the sequence of SEQ ID No. 27, and B3 primer has the sequence of SEQ ID No. 28; and both primers were used commonly in all sets.

[Test 2: Results]

Amplification products obtained by using the six kinds of primer sets shown in Table 4 were subjected to electrophoresis. After amplification for 1 hour, the primer sets 1, 2, 3, 4 and 5 gave sufficient amounts of amplification products. Similarly, after amplification for 2 hours, the primer sets 1, 2, 3, 4 and 5 gave sufficient amounts of amplification products. No amplification was observed with the primer set 6 even after 2 hours. No non-specific amplification was observed in any of the sets. The results showed that the primer sets 1, 2, 3, 4, and 5 were the most preferable. The results are summarized in Table 4.

[Test 3: Primer for T341C; BP Region]

An amplification reaction was performed at 63° C. for 1 hour or 2 hours, by using 13 kinds of nucleotide primer sets containing the NAT2 T341C polymorphic sites in the BP region. The composition of the reaction solution is shown in Table 1. The template DNA used was a human genome. For examination of the presence or absence of contamination and non-specific amplification, a negative control containing sterilized ultrapure water instead of the human genome was prepared in all sets. After the amplification reaction, amplification products were identified by 3% agarose electrophoresis.

The nucleotide primer sets used are shown in Table 5.

TABLE 4

Primer set having G857A in BP or BPc region

| Primer set | SEQ ID No. | Name | Sequence | 1-hour amplification | 2-hour amplification | Non-specific amplification |
|---|---|---|---|---|---|---|
| 1 | 20 | FIP-1 | AGCACTTCTTCAACCTCTTCCTCTAAAGACAATACAGATCTGGTCG | ○ | ○ | Not-occurred |
|   | 21 | BIP-1 | CCTTGGGGAGAAATCTCGTGCGTTCCTTATTCTAAATAGTAAGGGAT |   |   |   |
| 2 | 20 | FIP-1 | AGCACTTCTTCAACCTCTTCCTCTAAAGACAATACAGATCTGGTCG | ○ | ○ | Not-occurred |
|   | 22 | BIP-2 | GAGAAATCTCGTGCCCAAACCGTTCCTTATTCTAAATAGTAAGGGAT |   |   |   |
| 3 | 20 | FIP-1 | AGCACTTCTTCAACCTCTTCCTCTAAAGACAATACAGATCTGGTCG | ○ | ○ | Not-occurred |
|   | 23 | BIP-3 | GAAATCTGTGCCCAAACCCAAGGGTTTATTTTGTTCCTTATTC | ○ | ○ | Not-occurred |
| 6 | 20 | FIP-1 | AGCACTTCTTCAACCTCTTCCTCTAAAGACAATACAGATCTGGTCG | x | x | Not-occurred |
|   | 24 | BIP-4 | GAGAAATCTCGTGCCCAAACGTTCCTTATTCTAAATAGTAAGGG |   |   |   |
| 4 | 20 | FIP-1 | AGCACTTCTTCAACCTCTTCCTCTAAAGACAATACAGATCTGGTCG | ○ | ○ | Not-occurred |
|   | 25 | BIP-5 | CCTTGGGGAGAAATCTCGTGAGGGTTTATTTTGTTCCTTATTC |   |   |   |
| 5 | 20 | FIP-1 | AGCACTTCTTCAACCTCTTCCTCTAAAGACAATACAGATCTGGTCG | ○ | ○ | Not-occurred |
|   | 26 | BIP-6 | GGGGAGAAATCTCGTGCCCAAGGGTTTATTTTGTTCCTTATTC |   |   |   |
|   | 27 | F3 | GTGGGCTTCATCCTCAC |   |   |   |
|   | 28 | B3 | TGATAATTAGTGAGTTGGGTGAT |   |   |   |

TABLE 5

Primer set having T341C in BP or BPc region

| Primer set | SEQ ID No. | Name | Sequence | 1-hour amplification | 2-hour amplification | Non-specific amplification |
|---|---|---|---|---|---|---|
| 11 | 29 | FIP-1 | CTGTATTTGTTAACTGGAGGCTCTGACCACAATCGGTTC | x | o | Occurred |
|  | 30 | BIP-1 | CATGGTTCACCTTCTCCTGCAGACCCAGCATYGACAATG |  |  |  |
| 12 | 29 | FIP-1 | CTGTATTTGTTAACTGGAGGCTCTGACCACAATCGGTTC | x | x | Not-occurred |
|  | 31 | BIP-2 | CATGGTTCACCTTCTCCTGGAGCTTCCAGACCCAGCA |  |  |  |
| 13 | 29 | FIP-1 | CTGTATTTGTTAACTGGAGGCTCTGACCACAATCGGTTC | x | x | Not-occurred |
|  | 32 | BIP-3 | CATGGTTCACCTTCTCCTGAGCTTCCAGACCCAGCAT |  |  |  |
| 1 | 33 | FIP-2 | TGTGGTCTGAAAACCGATTGGGTGTCTCCAGGTCAATCAA | x | o | Not-occurred |
|  | 30 | BIP-1 | CATGGTTCACCTTCTCCTGCAGACCCAGCATYGACAATG |  |  |  |
| 2 | 33 | FIP-2 | TGTGGTCTGAAAACCGATTGGGTGTCTCCAGGTCAATCAA | x | o | Not-occurred |
|  | 31 | BIP-2 | CATGGTTCACCTTCTCCTGGAGCTTCCAGACCCAGCA |  |  |  |
| 3 | 33 | FIP-2 | TGTGGTCTGAAAACCGATTGGGTGTCTCCAGGTCAATCAA | o | o | Not-occurred |
|  | 32 | BIP-3 | CATGGTTCACCTTCTCCTGAGCTTCCAGACCCAGCAT |  |  |  |
| 4 | 34 | FIP-3 | GAAAACCGATTGTGGTCAGAGGGTGTCTCCAGGTCAATCAA | x | o | Not-occurred |
|  | 30 | BIP-1 | CATGGTTCACCTTCTCCTGCAGACCCAGCATYGACAATG |  |  |  |
| 5 | 34 | FIP-3 | GAAAACCGATTGTGGTCAGAGGGTGTCTCCAGGTCAATCAA | x | o | Not-occurred |
|  | 31 | BIP-2 | CATGGTTCACCTTCTCCTGGAGCTTCCAGACCCAGCA |  |  |  |
| 6 | 34 | FIP-3 | GAAAACCGATTGTGGTCAGAGGGTGTCTCCAGGTCAATCAA | o | o | Not-occurred |
|  | 32 | BIP-3 | CATGGTTCACCTTCTCCTGAGCTTCCAGACCCAGCAT |  |  |  |
| 7 | 35 | FIP-4 | TTGATTGACCTGGAGACACGGCTTAGAGGCTATTTTTGATCA | x | o | Not-occurred |
|  | 32 | BIP-3 | CATGGTTCACCTTCTCCTGAGCTTCCAGACCCAGCAT |  |  |  |
| 8 | 36 | FIP-5 | TTGATTGACCTGGAGACAGGCTTAGAGGCTATTTTTGATCA | x | o | Not-occurred |
|  | 32 | BIP-3 | CATGGTTCACCTTCTCCTGAGCTTCCAGACCCAGCAT |  |  |  |
| 9 | 37 | FIP-6 | TTGATTGACCTGGAGACACGGCTTAGAGGCTATTTTTGATCACA | o | o | Not-occurred |
|  | 32 | BIP-3 | CATGGTTCACCTTCTCCTGAGCTTCCAGACCCAGCAT |  |  |  |
| 10 | 38 | FIP-7 | TTGATTGACCTGGAGACACGCTTAGAGGCTATTTTTGATCACA | o | o | Not-occurred |
|  | 32 | BIP-3 | CATGGTTCACCTTCTCCTGAGCTTCCAGACCCAGCAT |  |  |  |
|  | 39 | F3-1 | GAGGCTATTTTTGATCACATTGTA |  |  |  |
|  | 40 | B3-1 | GGCTGCCACATCTGGGAG |  |  |  |
|  | 41 | F3-2 | TGTGGGCAAGCCATGGAG |  |  |  |

The F3 primer in the primer sets 1, 2, 3, 4, 5, 11, 12, 13 and 14 had the sequence of SEQ ID No. 39. The F3 primer in the primer sets 6, 7, 8 and 9 had the sequence of SEQ ID No. 41. The B3 primer had the sequence of SEQ ID No. 40 and was used commonly in all sets.

[Test 3: Results]

Amplification products obtained by using the 13 kinds of primer sets shown in Table 5 were subjected to electrophoresis. After amplification for 1 hour, the primer sets 3, 6, 9, and 10 gave sufficient amounts of amplification products. After amplification for 2 hours, the primer sets 1, 2, 3, 4, 5, 6, 7, 8, 9, 10 and 11 gave sufficient amounts of amplification products. No amplification was observed with the primer sets 12 and 13 even after 2 hours. There was observed non-specific amplification with the primer set 11. No non-specific amplification was observed with the primer sets 1, 2, 3, 4, 5, 6, 7, 8, 9, and 10. The results above showed that the primer sets 1, 2, 3, 4, 5, 6, 7, 8, 9 and 10 were preferable and that the primer sets 3, 6, 9, and 10 were the most preferable. The results are summarized in Table 5.

<Selection of Nucleotide Primer for Simultaneous Amplification of G590A and G857A Polymorphic Sites>

Polymorphic sites may be placed both in the FP region and the BP region. In this way, it is possible to measure two or more single-nucleotide polymorphism sites only with one amplification product. For example, in the case of G590A and G857A, G590A may be placed in the FP region, and G857A in the FP region. Although the amplification efficiency is lowered to some extent, because G590A and G857A are separated to some extent from each other and a target length (length from F2 to B2) becomes approximately 350 bp, it is possible to amplify in a short period of 1 hour, for example, by introducing a loop primer. For simultaneous amplification of G590A and G857A, it is possible to use a method of amplifying respective products in a single reaction tube (multiamplification), but the multiamplification demands strict condition setting. In addition, even strict control may result in preferential amplification of only one product and no amplification of the other. Thus, the simultaneous measurement of 2 or more single-nucleotide polymorphism sites with one amplification product by the method described above is particularly advantageous.

[Test 4: Primer for G590A (FP Region) and Primer for G857A (BP Region)]

An amplification reaction was performed at 63° C. for 1 hour or 2 hours, by using 11 kinds of nucleotide primer sets containing the NAT2 G590A polymorphic sites in the FP region and the NAT2 G857A polymorphic sites in the BPc region. The composition of the reaction solution is shown in Table 1. The template DNA used was a human genome. For examination of the presence or absence of contamination and non-specific amplification, a negative control containing sterilized ultrapure water instead of the human genome was prepared in all sets. After the amplification reaction, amplification products were identified by 3% agarose electrophoresis.

The nucleotide primer sets used are shown in Table 6.

F3 primer has the sequence of SEQ ID No. 49, and B3 primer has the sequence of SEQ ID No. 50; and both primers were used commonly in all sets.

[Test 4: Results]

Amplification products obtained by using the 11 kinds of primer sets shown in Table 6 were subjected to electrophoresis. After amplification for 1 hour, there was no amplification observed with any primer set. After amplification for 1.5 hours, the primer sets 1, 6, 7, and 8 gave sufficient amounts of amplification products. After amplification for 2 hours, the

TABLE 6

Primer set having G590A in FP or FPc region and G857A in BP or BPc region

| Primer set | SEQ ID No. | Name | Sequence | 1-hour amplification | 1.5-hour amplification | 2-hour amplification | Non-specific amplification |
|---|---|---|---|---|---|---|---|
| 1 | 42 | FIP-1 | GGAGACGTCTGCAGGTATGTATTCACTTATTTACGCTTGAACC | x | o | o | Not-occurred |
|   | 43 | BIP-1 | GATTTCCTTGGGGAGAAATCTCGTGACACAAGGGTTTATTTTGTTCC | | | | |
| 2 | 42 | FIP-1 | GGAGACGTCTGCAGGTATGTATTCACTTATTTACGCTTGAACC | x | x | o | Not-occurred |
|   | 44 | BIP-3 | GGGGAGAAATCTCGTGCCCAAGGGTTTATTTTGTTCCTTATTC | | | | |
| 3 | 45 | FIP-2 | GAGACGTCTGCAGGTATGTATTCATCCAAAAAATATACTTATTTACGC | x | x | o | Not-occurred |
|   | 43 | BIP-1 | GATTTCCTTGGGGAGAAATCTCGTGACACAAGGGTTTATTTTGTTCC | | | | |
| 4 | 45 | FIP-2 | GAGACGTCTGCAGGTATGTATTCATCCAAAAAATATACTTATTTACGC | x | x | o | Not-occurred |
|   | 46 | BIP-2 | CTTGGGGAGAAATCTCGTGCCCCATACACAAGGGTTTATTTTGTTCC | | | | |
| 9 | 45 | FIP-2 | GAGACGTCTGCAGGTATGTATTCATCCAAAAAATATACTTATTTACGC | x | x | x | Not-occurred |
|   | 44 | BIP-3 | GGGGAGAAATCTCGTGCCCAAGGGTTTATTTTGTTCCTTATTC | | | | |
| 5 | 47 | FIP-3 | CGTCTGCAGGTATGTATTCATAGACCCAAAAAATATACTTATTTACGC | x | x | o | Not-occurred |
|   | 43 | BIP-1 | GATTTCCTTGGGGAGAAATCTCGTGACACAAGGGTTTATTTTGTTCC | | | | |
| 10 | 47 | FIP-3 | CGTCTGCAGGTATGTATTCATAGACCCAAAAAATATACTTATTTACGC | x | x | o | Occurred |
|   | 46 | BIP-2 | CTTGGGGAGAAATCTCGTCCCCATACACAAGGGTTTATTTTGTTCC | | | | |
| 11 | 47 | FIP-3 | CGTCTGCAGGTATGTATTCATAGACCCAAAAAATATACTTATTTACGC | x | x | x | Not-occurred |
|   | 44 | BIP-3 | GGGGAGAAATCTCGTGCCCAAGGGTTTATTTTGTTCCTTATTC | | | | |
| 6 | 48 | FIP-4 | CTGCAGGTATGTATTCATAGACTCCACCAAAAAATATACTTATTTACGC | x | o | o | Not-occurred |
|   | 43 | BIP-1 | GATTTCCTTGGGGAGAAATCTCGTGACACAAGGGTTTATTTTGTTCC | | | | |
| 7 | 48 | FIP-4 | CTGCAGGTATGTATTCATAGACTCCACCAAAAAATATACTTATTTACGC | x | o | o | Not-occurred |
|   | 46 | BIP-2 | CTTGGGGAGAAATCTCGTGCCCCATACACAAGGGTTTATTTTGTTCC | | | | |
| 8 | 48 | FIP-4 | CTGCAGGTATGTATTCATAGACTCCACCAAAAAATATACTTATTTACGC | x | o | o | Not-occurred |
|   | 44 | BIP-3 | GGGGAGAAATCTCGTGCCCAAGGGTTTATTTTGTTCCTTATTC | | | | |
|   | 49 | F3 | TCTCATCTCCTGCCAAAGAAG | | | | |
|   | 50 | B3 | AGTTGATAATTAGTGAGTTGGGTG | | | | |
|   | 80 | LB | GTGCCCAAACCTGGTG | | | | | primer set 1, 2, 3, 4, 5, 6, 7, 8 and 10 gave sufficient amounts of amplification products. There was no amplification observed even after 2 hours with the primer sets 9 and 11. There was non-specific amplification observed with the primer set 10. No non-specific amplification was observed with the primer sets 1, 2, 3, 4, 5, 6, 7, and 8. The results above showed that the primer sets 1, 2, 3, 4, 5, 6, 7 and 8 were preferable and that the primer sets 1, 6, 7, and 8 were the most preferable. The results are summarized in Table 6.

The preferable inner primer provided by the present invention was determined by the above tests. As apparent for those who are skilled in the art, the primer most important in the LAMP reaction is the inner primer. An inner primer is essential for amplification reaction, but outer and loop primers are not. The addition of outer and loop primers to the amplification reaction solution may lead to an increase of amplification efficiency, but it's positional change gives less influence on amplification efficiency than that of the inner primer. Thus, the outer primers (F3 and B3 primers) can be designed optionally. For example, it is preferably placed in the region within 60 bases from the 5' terminal of the F2 region and the region within 60 bases from the 3' terminal of the B2c region. Thus, the F3 region having the same sequence as the F3 primer is preferably placed in the region within 60 bases from the 5' terminal of the F2 region, and the B3c region having a sequence complementary to the B3 primer in the region within 60 bases from the 3' terminal of the B2c region. The loop primer is preferably designed to bind to a loop other than the loop to which the inner primer binds, and the loop primer is not placed in the inner primer region.

<Selection of Nucleotide Probe>

The chain of the nucleotide probe is neither too long nor too short. Generally, an increase in chain length leads to an increase in the binding force, although there is some difference in the binding force according to the kind of the base. An excessively small chain length of the nucleotide probe leads to deterioration of the hybridization efficiency between the nucleotide probe and amplification products. On the other hand, an excessively large chain length of the nucleotide probe leads to a decrease in one-base difference between the wild-type nucleotide probe and the variant nucleotide probe. Accordingly, non-specific bonding between wild-type amplification products and variant nucleotide probes and also between variant amplification products and wild-type nucleotide probes increases. Thus, it is preferable to use a nucleotide probe having an appropriate chain length, for example of 10 to 35 bases, for detection of single-nucleotide polymorphism.

The binding force may be indicated by the dissociation temperature Tm of the double-strand nucleotide. The Tm value is calculated, for example, by nearest neighbor method, Wallance method, or GC % method. In the present invention, used is the nearest neighbor method (Breslauer et. al., 1986; Freier et. al., 1986; Schildkraut et. al., 1965). In the invention, it is calculated under the condition of an $Na^+$ concentration of 50 mM and a nucleotide probe (oligonucleotide) concentration of 0.5 µM.

Hereinafter, a test for selecting a nucleotide probe suitably used in detecting amplification products obtained according to the present invention will be described.

[Test 5-1: Probe for Detection of G590A]

LAMP amplification was performed at 63° C. for 1 hour, by using a human genome determined to be heterozygous by Polymerase chain reaction-restriction fragment length polymorphism (PCR-RFLP) analysis as a template and also the primer set 9 for detection of G590A. The primer set 9 for detection of G590A is a set determined to be the best primer in the test 1-2 above. The amplification products obtained were detected on a current-detection DNA chip.

Nucleotide Probe:

The nucleotide sequences of the nucleotide probes tested are summarized in Table 7. The nucleotide probe used was a plus chain. The 3' terminal of the nucleotide probe was thiol-modified for immobilization on an electrode. The negative control probe was a nucleotide having a sequence completely unrelated to the NAT2 gene.

TABLE 7

Nucleotide probe used for detection of products amplified with G590A-detecting primer set 9

|  | SEQ ID No. | Base number | Tm value | F/R | Sequence |
|---|---|---|---|---|---|
| Negative | 51 | 14 mer |  |  | GTGCTGCAGGTGCG |
| G590A Wild-type | 52 | 17 mer | 53.9 | F | GAACCTCGAACAATTGA |
|  | 53 | 21 mer | 61.6 | F | TTGAACCTCGAACAATTGAAG |
|  | 54 | 26 mer | 66.2 | F | TTGAACCTCGAACAATTGAAGATTTT |
|  | 55 | 29 mer | 69.9 | F | TTGAACCTCGAACAATTGAAGATTTTGAG |
| Variant | 56 | 19 mer | 54.5 | F | GAACCTCAAACAATTGAAG |
|  | 57 | 21 mer | 57.1 | F | GAACCTCAAACAATTGAAGAT |
|  | 58 | 23 mer | 61.2 | F | TTGAACCTCAAACAATTGAAGAT |
|  | 59 | 27 mer | 66.5 | F | TTGAACCTCAAACAATTGAAGATTTTG |
|  | 60 | 30 mer | 68.6 | F | TTGAACCTCAAACAATTGAAGATTTTGAGT |

Nucleotide Probe-Immobilized Support:

Gold electrodes were made on a DNA chip, and the nucleotide probes were immobilized thereon. Immobilization was performed by using the strong bonding force between thiol and gold. A probe solution containing a nucleotide probe with a thiol-modified terminal was spotted on the gold electrode, and, after 1 hour, the DNA chip was immersed in 1 mM mercaptohexanol solution and then, washed with 0.2×SSC solution. The same probe was spotted on two electrodes. After washing, the chip was washed with ultrapure water and dried in air, to give a nucleotide probe-immobilized support.

The nucleotide probes were immobilized on the following electrodes respectively:

Electrodes 1-2: negative probe (SEQ ID No. 51)
Electrodes 3-4: wild-type nucleotide probe 17mer (SEQ ID No. 52)
Electrodes 5-6: wild-type nucleotide probe 21mer (SEQ ID No. 53)
Electrodes 7-8: wild-type nucleotide probe 26mer (SEQ ID No. 54)
Electrodes 9-10: wild-type nucleotide probe 29mer (SEQ ID No. 55)

Electrodes 11-12: variant nucleotide probe 19mer (SEQ ID No. 56)
Electrodes 13-14: variant nucleotide probe 21mer (SEQ ID No. 57)
Electrodes 15-16: variant nucleotide probe 23mer (SEQ ID No. 58)
Electrodes 17-18: variant nucleotide probe 27mer (SEQ ID No. 59)
Electrodes 19-20: variant nucleotide probe 30mer (SEQ ID No. 60)

Hybridization between amplification products and nucleotide probe, and detection thereof:

To the amplification products obtained by amplification were added salts at a final concentration of 2×SSC, and the mixture was allowed to hybridize with the electrode-immobilized nucleotide probe. The reaction temperatures were 35, 45, 50, 55, and 60° C., and the reaction period was 60 minutes. Then, the DNA chip was washed mildly with ultrapure water. The DNA chip was immersed in a phosphate buffer containing 50 μM of an intercalating agent Hoechst 33258 for 10 minutes and washed, and then the oxidative current response of the Hoechst 33258 molecule was measured.

[Test 5-1: Results]

Figure 13:
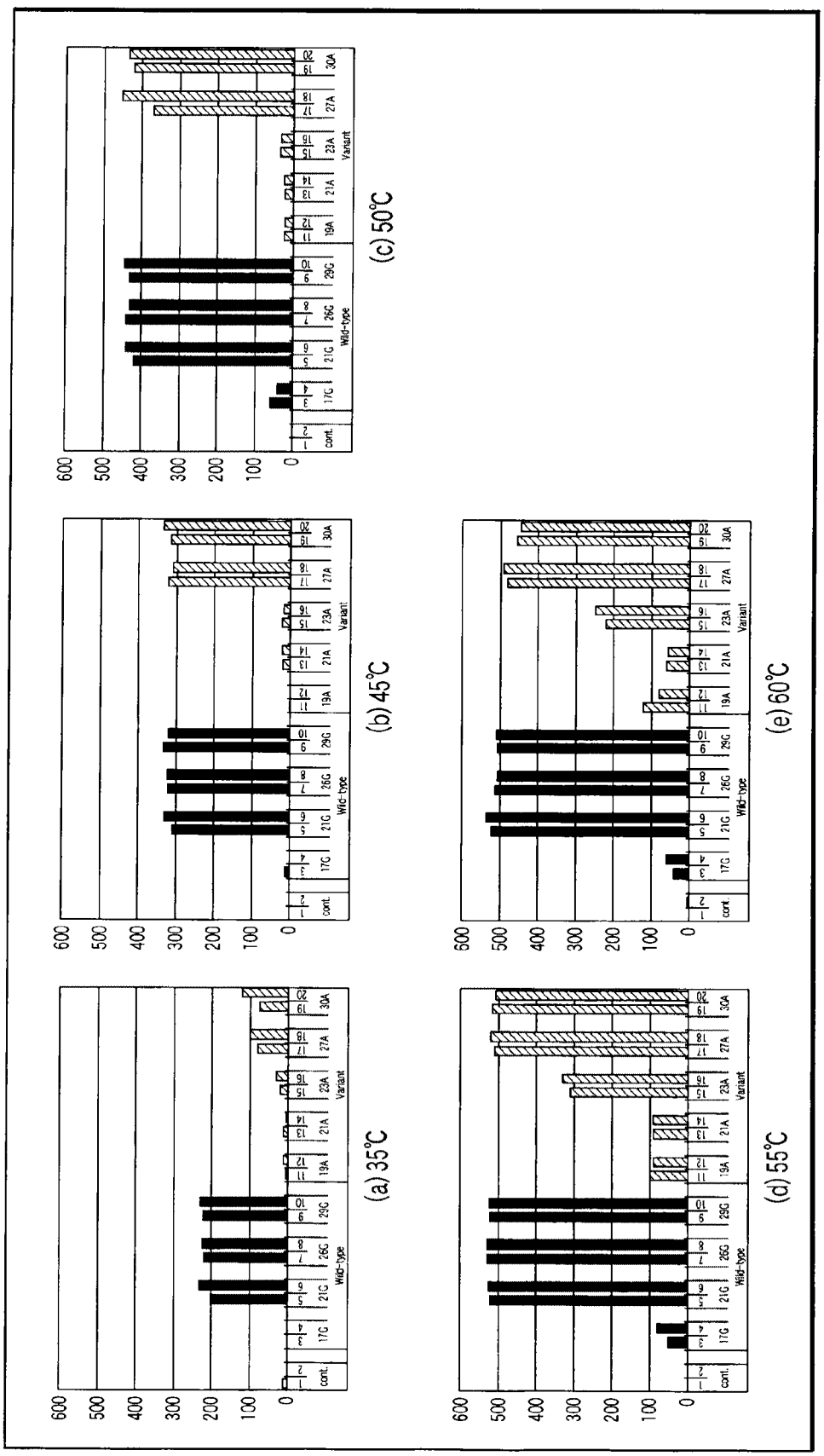
FIG. 13 shows graphs indicating the test result 1 obtained by using the probe for detection of G590A.

The results are summarized in FIG. 13. The signal increased as the reaction temperature increased, indicating that an increase in reaction temperature leads to an increase in hybridization efficiency. The tests at reaction temperatures of 55 and 60° C. gave almost the same results.

[Test 5-2: Probe for Detection of G590A]

Then, hybridization was performed in a similar manner to the test 5-1, except that the reaction temperature was 55° C. and the reaction times were 10, 20, 40, 60, and 120 minutes.

[Test 5-2: Results]

Figure 14:
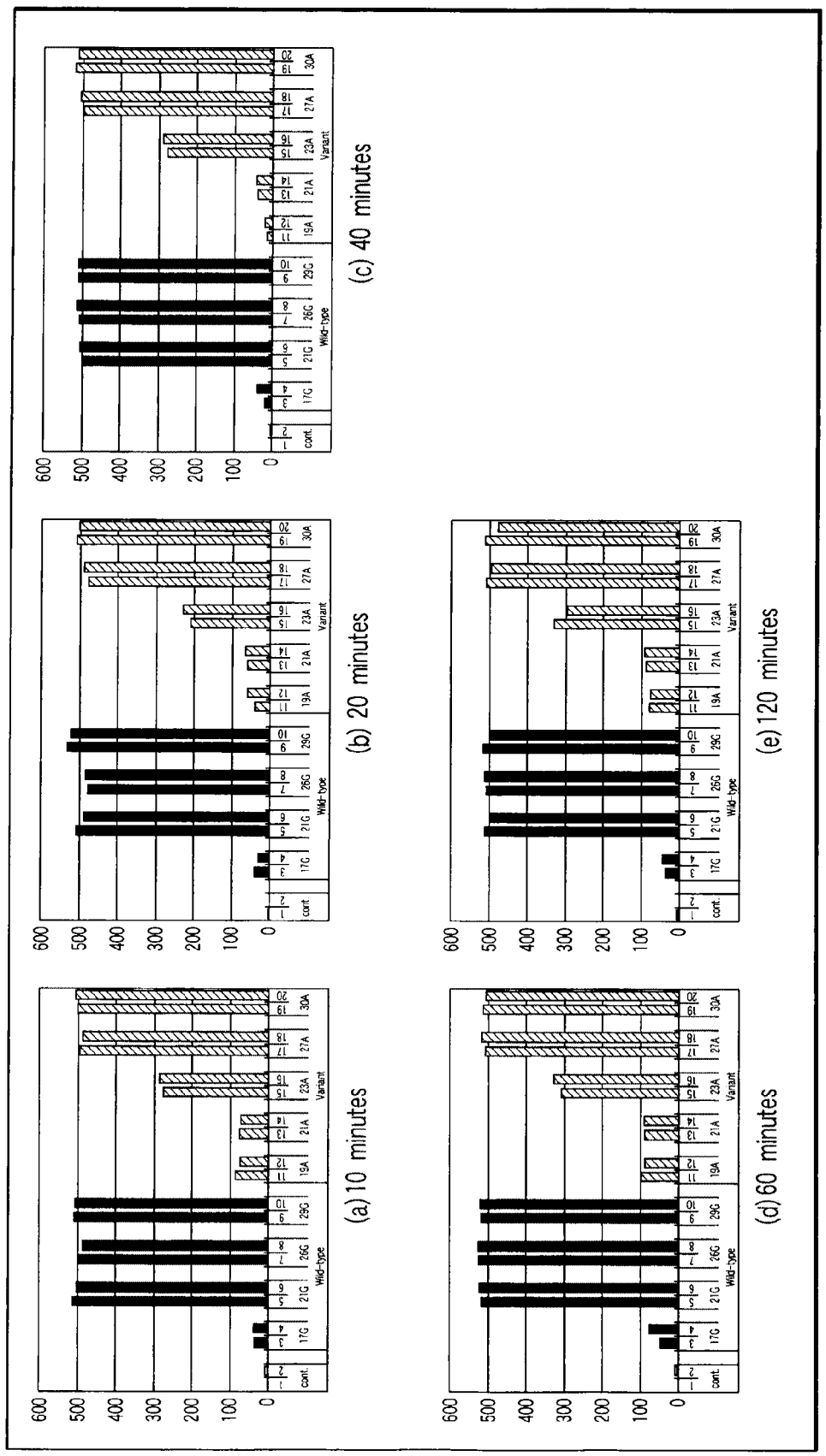
FIG. 14 shows graphs indicating the test result 2 obtained by using the probe for detection of G590A.

The results are summarized in FIG. 14. The tests at reaction times of 10 and 120 minutes gave almost the same results, indicating that the hybridization reaction was already in the saturated state after 10 minutes.

Wild-type nucleotide probe (17G: SEQ ID No. 52) and variant nucleotide probes (19A: SEQ ID No. 56, 21A: SEQ ID No. 57, and 23A: SEQ ID No. 58) relatively shorter in chain length gave a signal relatively lower in intensity. Wild-type nucleotide probes (21G: SEQ ID No. 53, 26G: SEQ ID No. 54, and 29G: SEQ ID No. 55) and variant nucleotide probes (27A: SEQ ID No. 59 and 30A: SEQ ID No. 60) gave a signal almost the same in intensity.

[Test 5-3: Probe for Detection of G590A]

Then, hybridization was performed in a manner similar to the test 5-1 at a reaction temperature of 55° C. for 20 minutes. Subsequently, the nucleotide probe-immobilized support was immersed for 20 minutes in a 0.2×SSC washing buffer at 40, 45, or 50° C. The analyte nucleotides used for amplification in the present test were 3 kinds of human genomes determined to be respectively wild homozygous, variant homozygous, and heterozygous respectively, by PCR-RFLP analysis.

[Test 5-3: Results]

Figure 15B:
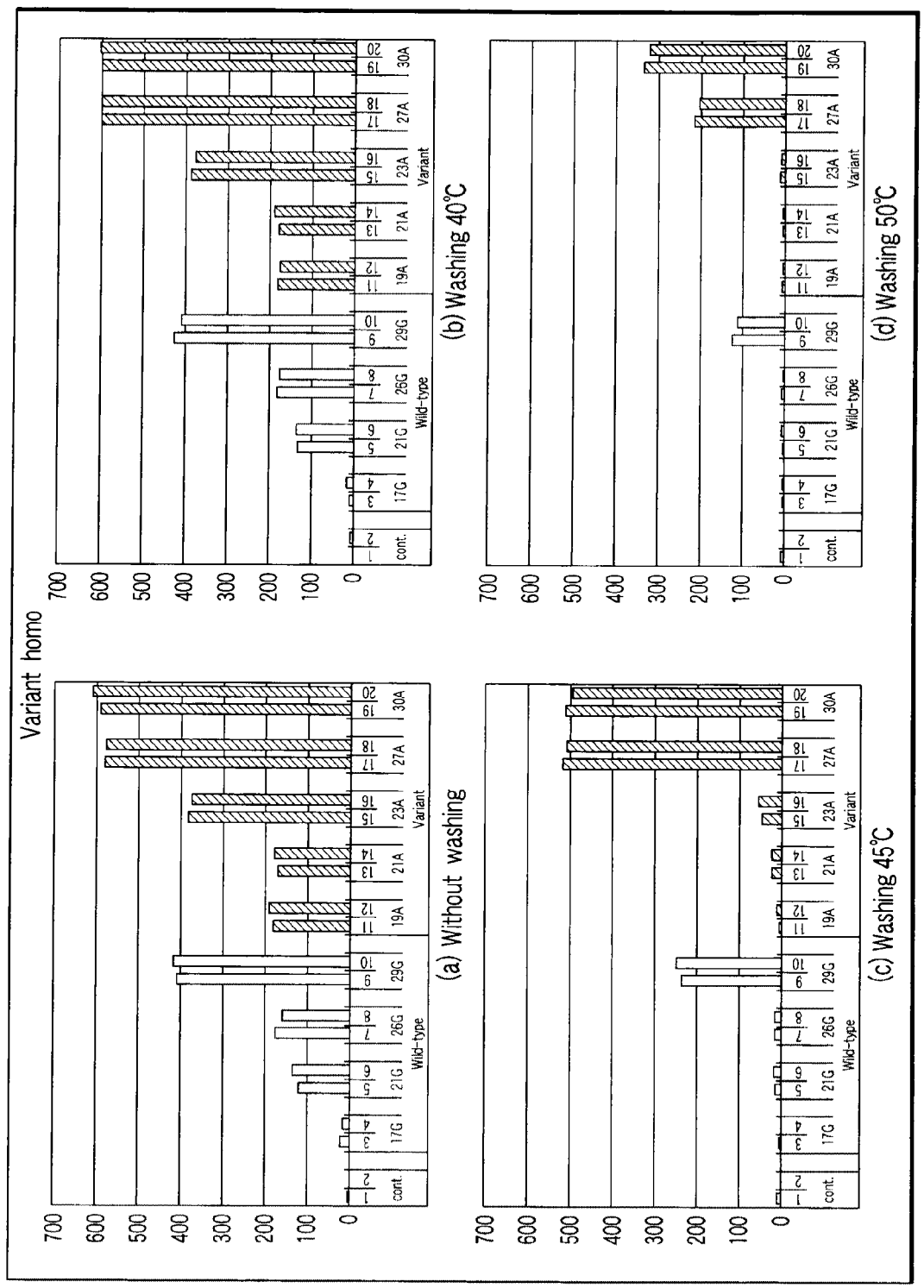
FIG. 15B shows graphs indicating the test result 3 (variant) obtained by using the probe for detection of G590A.
Figure 15C:
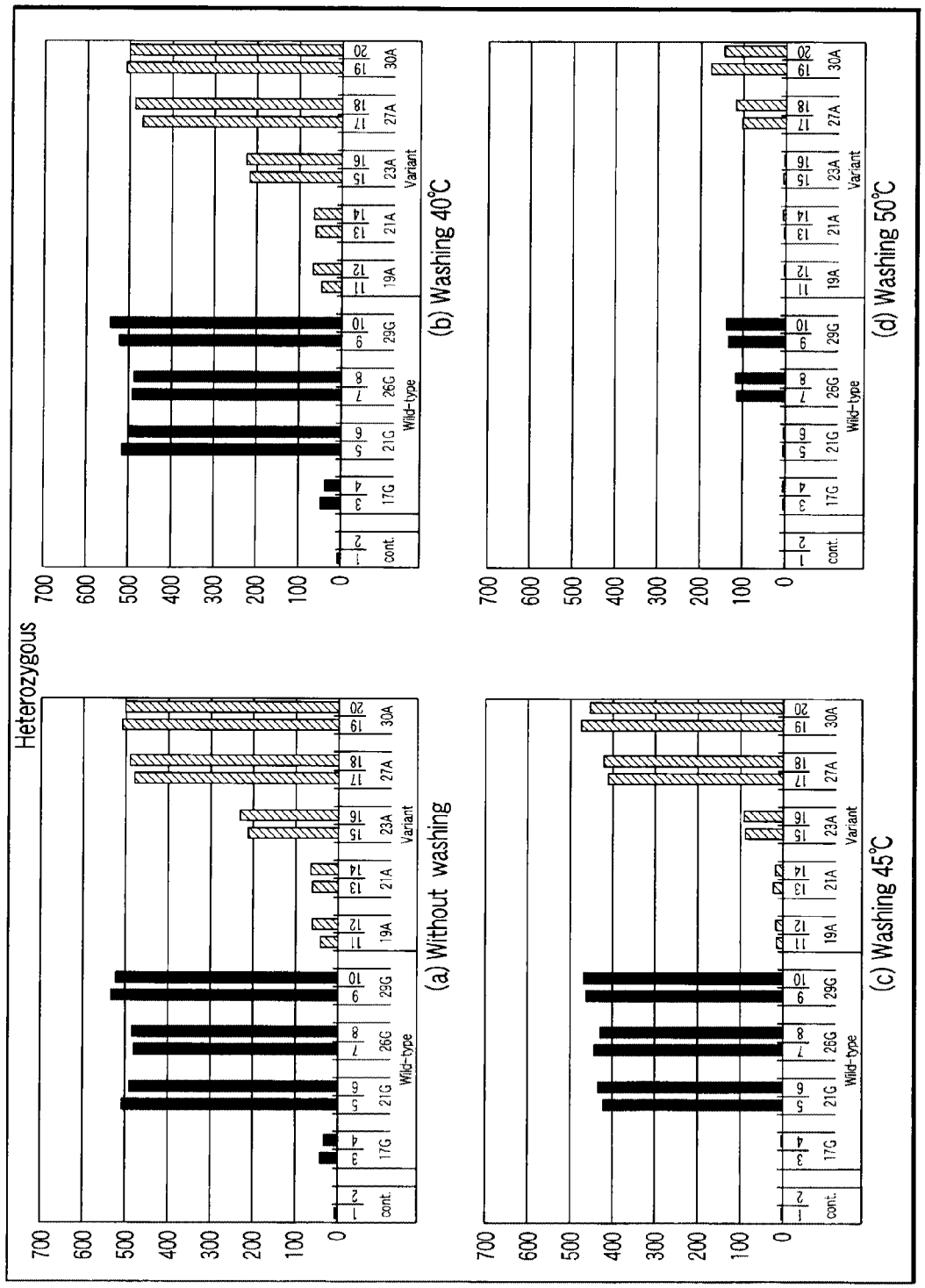
FIG. 15C shows graphs indicating the test result 3 (heterozygous) obtained by using the probe for detection of G590A.

The results are summarized in FIGS. 15A to 15C. When the DNA chip was not washed (only washed mildly with ultrapure water), there were wild-type amplification products detected by the variant nucleotide probe and also variant amplification products detected by the wild-type nucleotide probe, indicating the presence of non-specific hybridization. The results at a washing temperature of 40° C. were almost the same as those without washing.

At a washing temperature of 45° C., wild-type amplification products were detected by wild-type nucleotide probes (21G and 26G) at high signal intensity, but almost no signal was detected by a variant nucleotide probe (27A). Similarly, variant amplification products were detected by the variant nucleotide probe (27A) at high signal intensity, but almost no signal was detected by the wild-type nucleotide probes (21G and 26G), indicating that bonds formed by non-specific hybridization were broken by washing at 45° C. Alternatively, heterozygous amplification products were detected both by the wild-type nucleotide probes (21G and 26G) and the variant nucleotide probe (27A) at high signal intensity.

At a washing temperature of 50° C., the current detected was lower, indicating that amplification products were separated from the nucleotide probe by washing. At a washing temperature of 50° C., the signal of wild-type amplification products by wild-type nucleotide probe (29G) decreased, but the signal of the variant amplification product by wild-type nucleotide probe remained high, indicating non-specific binding remaining. Similarly, the signal of the variant amplification product by variant nucleotide probe (30A) decreased, but the signal of wild-type amplification products by variant nucleotide probe remained high.

The results showed that the wild-type nucleotide probes (21G and 26G) and the variant nucleotide probe (27A) give an ideal detection pattern. Accordingly, the nucleotide probes most preferably used according to the present invention are the wild-type nucleotide probes (21G: SEQ ID No. 53 and 26G: SEQ ID No. 54) and the variant nucleotide probe (27A: SEQ ID No. 59).

The Tm values of the nucleotide probes used in the test are also summarized in Table 7. As apparent from Table 7, the nucleotide probes preferably used in the present invention are wild-type nucleotide probes having a Tm value of 62 to 70° C., preferably 62 to 66° C., and variant nucleotide probes having a Tm value of 61 to 69° C., preferably 66 to 67° C.

[Test 6-1: Probe for Detection of G857A]

LAMP amplification was performed at 63° C. for 1 hour by using a human genome determined to be heterozygous by PCR-RFLP analysis as the template and also by using the primer sets 1 and 5 for detection of G857A. The primer sets 1 and 5 for detection of G857A were the sets determined to be the best in the test 2 above. The amplification products obtained were detected on a current-detection DNA chip.

Nucleotide Probe:

The nucleotide sequences of the nucleotide probes tested are summarized in Table 8. The nucleotide probe used was a plus chain. The 3' terminal of the nucleotide probe was thiol-modified for immobilization on an electrode. The negative control probe was a nucleotide having a sequence completely unrelated to the NAT2 gene sequence.

TABLE 8

Nucleotide probe used for detection of products amplified with G857A-detecting primer set 5

| | SEQ ID No. | Base number | Tm value | F/R | Sequence |
|---|---|---|---|---|---|
| G857A Wild-type | 61 | 20 mer | 59.3 | F | TGGTGATGGATCCCTTACTA |
| | 62 | 23 mer | 63.8 | F | CCTGGTGATGGATCCCTTACTAT |
| | 63 | 24 mer | 64.8 | F | CCTGGTGATGGATCCCTTACTATT |
| | 64 | 25 mer | 65.3 | F | ACCTGGTGATGGATCCCTTACTATT |
| | 65 | 30 mer | 68.4 | F | AACCTGGTGATGGATCCCTTACTATTTAGA |

TABLE 8-continued

Nucleotide probe used for detection of products
amplified with G857A-detecting primer set 5

| | SEQ ID No. | Base number | Tm value | F/R | Sequence |
|---|---|---|---|---|---|
| Variant | 66 | 22 mer | 58.4 | F | CTGGTGATGAATCCCTTACTAT |
| | 67 | 26 mer | 64.4 | F | ACCTGGTGATGAATCCCTTACTATTT |
| | 68 | 28 mer | 65.1 | F | AACCTGGTGATGAATCCCTTACTATTTA |
| | 69 | 29 mer | 65.6 | F | AACCTGGTGATGAATCCCTTACTATTTAG |
| | 70 | 31 mer | 67.5 | F | AACCTGGTGATGAATCCCTTACTATTTAGAA |

Nucleotide Probe-Immobilized Support:

A nucleotide probe-immobilized support was prepared in a similar manner to the test 5-1.

The nucleotide probes were immobilized on the following electrodes respectively:

Electrodes 1-2: negative probe (SEQ ID No. 51)
Electrodes 3-4: wild-type nucleotide probe 20mer (SEQ ID No. 61)
Electrodes 5-6: wild-type nucleotide probe 23mer (SEQ ID No. 62)
Electrodes 7-8: wild-type nucleotide probe 24mer (SEQ ID No. 63)
Electrodes 9-10: wild-type nucleotide probe 25mer (SEQ ID No. 64)
Electrodes 11-12: wild-type nucleotide probe 30mer (SEQ ID No. 65)
Electrodes 13-14: variant nucleotide probe 24mer (SEQ ID No. 66)
Electrodes 15-16: variant nucleotide probe 26mer (SEQ ID No. 67)
Electrodes 17-18: variant nucleotide probe 28mer (SEQ ID No. 68)
Electrodes 19-20: variant nucleotide probe 29mer (SEQ ID No. 69)
Electrodes 21-22: variant nucleotide probe 31mer (SEQ ID No. 70)

Hybridization between amplification products and nucleotide probe, and detection thereof:

To the amplification products obtained by amplification were added salts at a final concentration of 2×SSC, and the mixture was allowed to hybridize with the electrode-immobilized nucleotide probe. The reaction temperatures were 35, 45, 50, 55, and 60° C., and the reaction period was 20 minutes. Then, the DNA chip was washed mildly with ultrapure water. The DNA chip was immersed in a phosphate buffer containing 50 μM of an intercalating agent Hoechst 33258 for 10 minutes and washed, and then, the oxidative current response of the Hoechst 33258 molecule was measured.

[Test 6-1: Results]

Figure 16B:
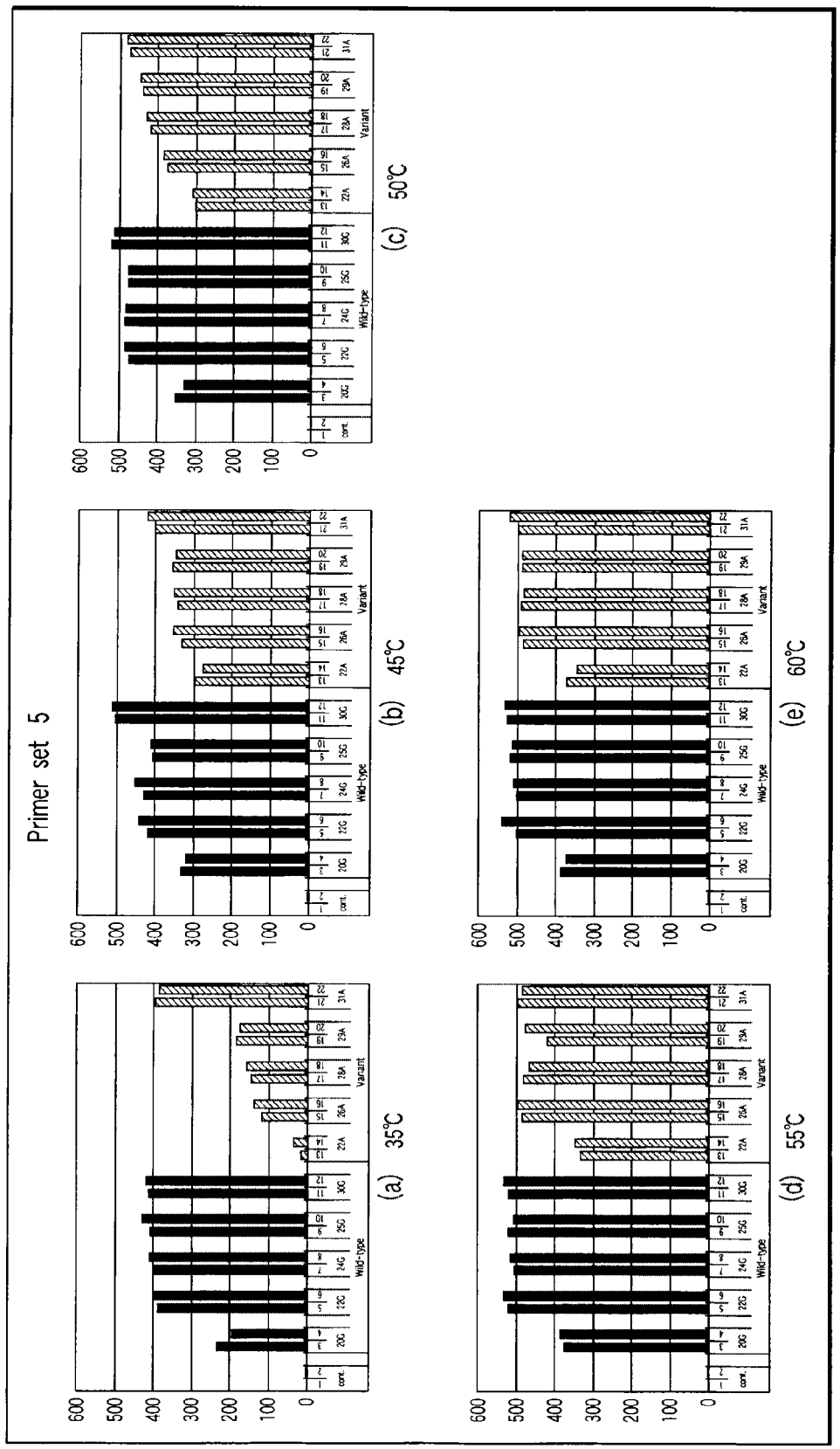
FIG. 16B shows graphs indicating the test result 1 (primer set 5) obtained by using the probe for detection of G857A.

The results are summarized in FIG. 16. FIG. 16A shows the results with the primer set 1, while FIG. 16B with the primer set 5. The signal increased as the reaction temperature increased, indicating that an increase in reaction temperature leads to an increase in hybridization efficiency. The tests at reaction temperatures of 55° C. and 60° C. gave almost the same results.

Detection of the LAMP products amplified by using the primer sets 1 and 5 for detection of G857A result in that the primer set 5 showed an increase in signal intensity associated with hybridization higher than that of the primer set 1. The reason for the difference in signal increase between the primer sets 1 and 5 is unclear. It is likely that the hybridization efficiency may be changed according to the length of the single-stranded region in an amplification product or the position of the region binding to the nucleotide probe. Alternatively, it is likely that the quantity of Hoechst 33258 added to the amplification products may be different slightly.

[Test 6-2: Probe for Detection of G857A]

Then, hybridization was performed in a manner similar to the test 5-3 at a reaction temperature of 55° C. for 20 minutes by using the products amplified with the primer set 5. Subsequently, the nucleotide probe-immobilized support was washed as immersed in a 0.2×SSC washing buffer at 45° C. for 20 minutes. The analyte nucleotides used for amplification in the present test were 3 kinds of human genomes determined to be wild homozygous, variant homozygous and heterozygous respectively, by PCR-RFLP analysis.

[Test 6-2: Results]

Figure 17:
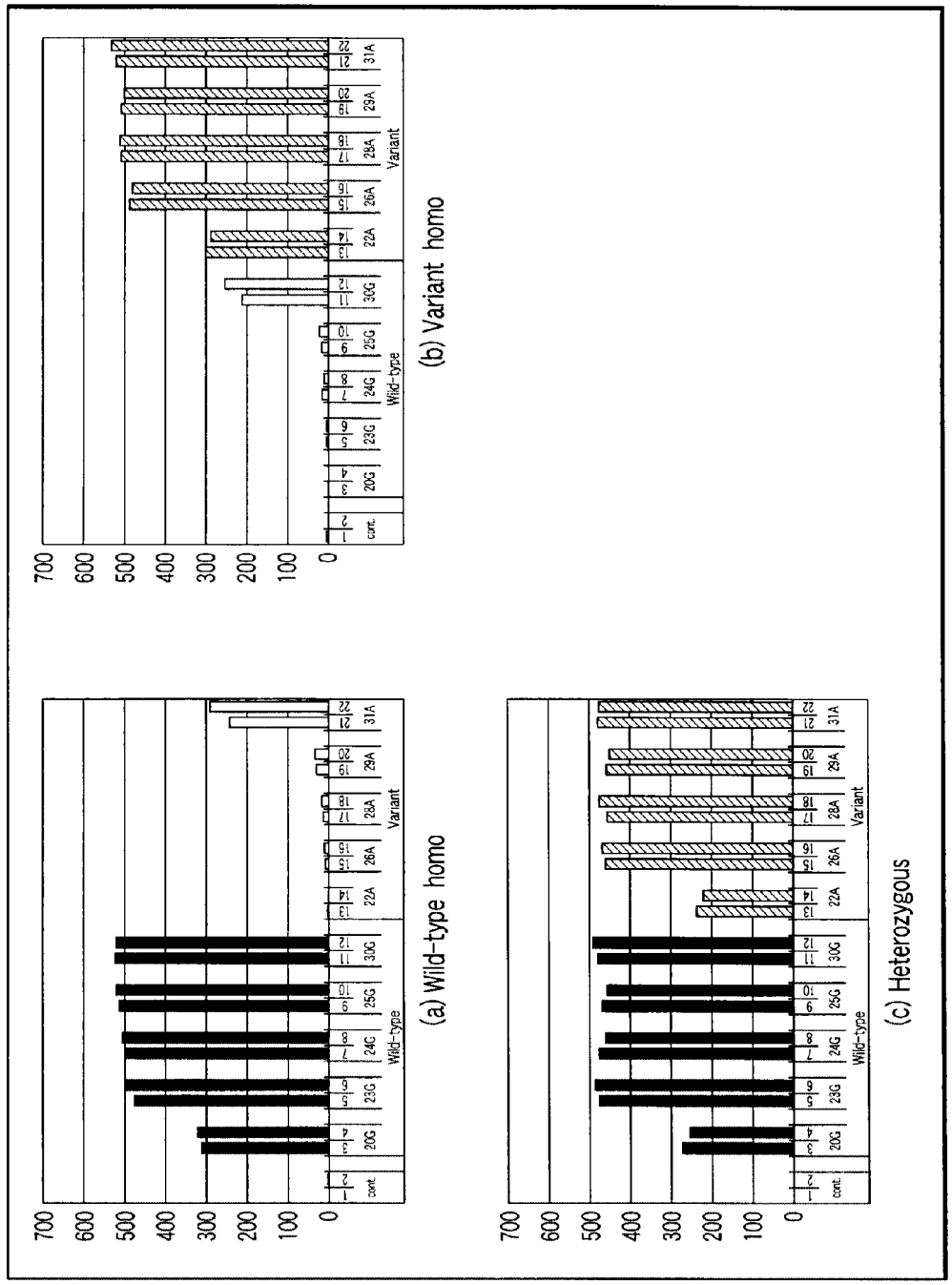
FIG. 17 shows graphs indicating the test result 2 obtained by using the probe for detection of G857A.

The results are summarized in FIG. 17. Wild-type amplification products were detected by wild-type nucleotide probes (23G, 24G, and 25G) at high signal intensity, while almost no signal was detected by the variant nucleotide probes (26A, 28A, and 29A). Similarly, variant amplification products were detected by the variant nucleotide probes (26A, 28A, and 29A) at high signal intensity, while almost no signal was detected by the wild-type nucleotide probes (23G, 24G, and 25G). In addition, heterozygous amplification products were detected both by the wild-type nucleotide probes (23G, 24G, and 25G) and also by the variant nucleotide probes (26A, 28A, and 29A) at high signal intensity.

The results showed that the wild-type nucleotide probes (23G, 24G, and 25G) and the variant nucleotide probes (26A, 28A, and 29A) give an ideal detection pattern. Thus, the nucleotide probes used most preferably according to the present invention are the wild-type nucleotide probes (23G: SEQ ID No. 62, 24G: SEQ ID No. 63, and 25G: SEQ ID No. 64) and the variant nucleotide probes (26A: SEQ ID No. 67, 28A: SEQ ID No. 68, and 29A: SEQ ID No. 69).

The Tm values of the nucleotide probes used were also summarized in Table 8. As apparent from in Table 8, the nucleotide probes preferably used in the present invention are wild-type nucleotide probes having a Tm value of 59 to 68° C., preferably 64 to 65° C., and variant nucleotide probes having a Tm value of 58 to 68° C., preferably 64 to 66° C.

[Test 7-1: Probe for Detection of T341C]

LAMP amplification was performed at 63° C. for 1 hour, by using human genomes determined to be wild homozygous, variant homozygous, and heterozygous by sequence analysis as the templates and the primer sets 6 and 10 for detection of T341C. The primer sets 6 and 10 for detection of T341C were the sets determined to be the best in the test 3 above. The amplification products obtained were detected on a current-detection DNA chip.

Nucleotide Probe:

The nucleotide sequences of the nucleotide probes tested are summarized in Table 9. The nucleotide probes used was a plus chain. The 3' terminal of the nucleotide probe was thiol-modified for immobilization on an electrode. The negative control probe used was a nucleotide having a sequence completely unrelated to the NAT2 gene sequence.

TABLE 9

Nucleotide probe used for detection of products amplified with T341C-detecting primer sets 6 and 10

|  |  | SEQ ID No. | Base number | Tm value | F/R | Sequence |
|---|---|---|---|---|---|---|
| T341C | Wild-type | 71 | 16 mer | 61.2 | F | GGTGACCATTGACGGC |
|  |  | 72 | 18 mer | 65.5 | F | AGGTGACCATTGACGGCA |
|  |  | 73 | 19 mer | 68.4 | F | CAGGTGACCATTGACGGCA |
|  |  | 74 | 20 mer | 69.0 | F | CAGGTGACCATTGACGGCAG |
|  | Variant | 75 | 16 mer | 57.8 | F | AGGTGACCACTGACGG |
|  |  | 76 | 17 mer | 62.6 | F | AGGTGACCACTGACGGC |
|  |  | 77 | 18 mer | 65.8 | F | AGGTGACCACTGACGGCA |
|  |  | 78 | 19 mer | 68.9 | F | CAGGTGACCACTGACGGCA |
|  |  | 79 | 20 mer | 69.5 | F | CAGGTGACCACTGACGGCAG |

Nucleotide probe-immobilized support:

A nucleotide probe-immobilized support was prepared in a similar manner to the test 5-1.

The nucleotide probes were immobilized on the following electrodes respectively:
Electrodes 1-2: negative probe (SEQ ID No. 51)
Electrodes 3-4: wild-type nucleotide probe 16mer (SEQ ID No. 71)
Electrodes 5-6: wild-type nucleotide probe 18mer (SEQ ID No. 72)
Electrodes 7-8: wild-type nucleotide probe 19mer (SEQ ID No. 73)
Electrodes 9-10: wild-type nucleotide probe 20mer (SEQ ID No. 74)
Electrodes 11-12: variant nucleotide probe 16mer (SEQ ID No. 75}
Electrodes 13-14: variant nucleotide probe 17mer (SEQ ID No. 76)
Electrodes 15-16: variant nucleotide probe 18mer (SEQ ID No. 77}
Electrodes 17-18: variant nucleotide probe 19mer (SEQ ID No. 78)
Electrodes 19-20: variant nucleotide probe 20mer (SEQ ID No. 79)

Hybridization between amplification products and nucleotide probe, and detection thereof:

To the amplification products obtained by amplification were added salts at a final concentration of 2×SSC, and the mixture was allowed to hybridize with the electrode-immobilized nucleotide probe. The reaction temperature was 55° C., and the reaction period was 20 minutes. Then, the chip was washed at 45° C. for 20 minutes. The electrode was immersed in a phosphate buffer containing 50 μM of an intercalating agent Hoechst 33258 for 10 minutes and washed, and then the oxidative current response of the Hoechst 33258 molecule was measured.

[Test 7-1: Results]

Figure 18B:
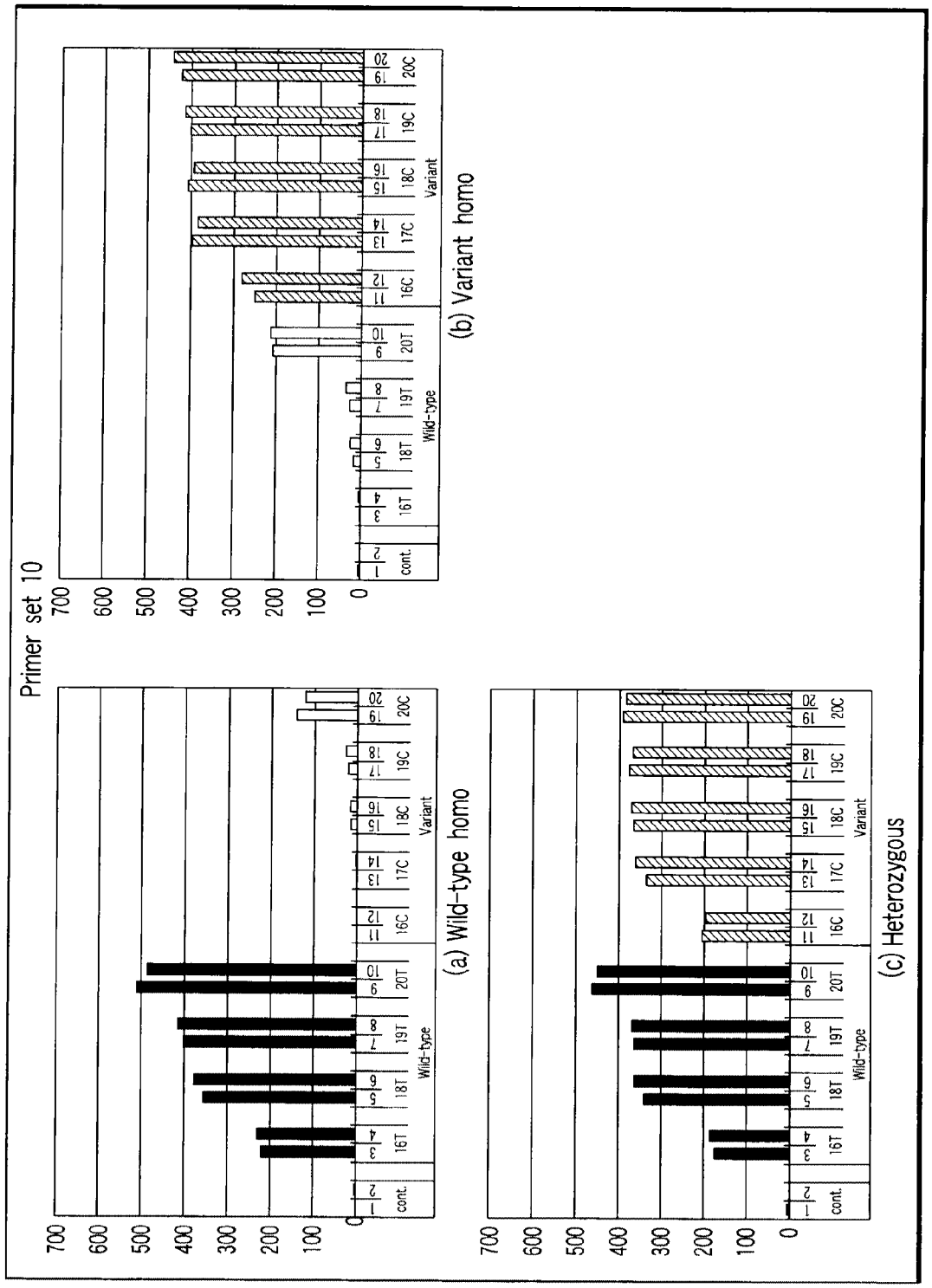
FIG. 18B shows graphs indicating the test result 1 (primer set 10) obtained by using the probe for detection of T341C.

The results are summarized in FIG. 18. FIG. 18A shows the results with the primer set 6, while FIG. 18B with the primer set 10. Nucleotide probes for detection of wild-type mutation (18T and 19T) and nucleotide probes for detection of variant (17C, 18C, and 19C) showed an ideal detection pattern. Wild-type amplification products were detected by the wild-type nucleotide probes (18T and 19T) at high signal intensity, while almost no signal increase was detected by the variant nucleotide probes (17C, 18C, and 19C) in which non-specific hybridization was broken. Similarly, variant amplification products were detected by the variant nucleotide probes (17C, 18C, and 19C) at high signal intensity, while almost no signal increase was detected by the wild-type nucleotide probes (18T and 19T) in which non-specific hybridization was broken. In addition, heterozygous amplification products were detected both by the wild-type nucleotide probes (18T and 19T) and the variant nucleotide probes (17C, 18C, and 19C) at high signal intensity. The amplification products obtained respectively by using the primer sets 6 and 10 for detection of T341C showed almost the same detection pattern.

The results showed that the nucleotide probes used most preferably according to the present invention were the wild-type nucleotide probes (18T: SEQ ID No. 72 and 19T: SEQ ID No. 73) and the variant nucleotide probes (17C: SEQ ID No. 76, 18C: SEQ ID No. 77, and 19C: SEQ ID No. 78).

The Tm values of the nucleotide probes used in the test are also summarized in Table 9. As apparent from the results in Table 9, the nucleotide probes preferably used in the present invention are wild-type nucleotide probes having a Tm value of 61 to 69° C., preferably 66 to 68° C., and variant nucleotide probes having a Tm value of 58 to 70° C., preferably 63 to 69° C.

[Test 8-1: Probe for Detection of G590A and G857A]

LAMP amplification was performed at 63° C., by using human genomes determined to be wild homozygous, variant homozygous and heterozygous respectibely, by PCR-RFLP analysis as the templates and the primer set 6 for detection of G590A and G857A. The primer set 6 for detection of G590A and G857A was the set determined to be the best in the test 4 above. The amplification products obtained were detected on a current-detection DNA chip.

Shortening of amplification period with loop primer:

The primer set for detection of G590A and G857A takes about 1.5 hours for amplification. Thus, shortening of the amplification period was examined by introducing a loop primer. The loop primer was the LB primer (SEQ ID No. 80) shown in Table 6. The loop primer was added to a 25 μl reaction solution in an amount of 40 pmol. Amplification results showed that the introduction of a loop primer led to completion of amplification within 1 hour.

DNA Chip Detection Result:

The amplification products of the primer set 6 for detection of G590A and G857A amplified with the introduced loop primer were detected by using the following nucleotide probes shown to be the most preferable nucleotide probes in the tests 5 and 6.

Nucleotide Probe:

The probe for detection of wild-type (SEQ ID No. 54) and the probe for detection of variant (SEQ ID No. 59) shown in Table 7 were used for G590A polymorphism, while the probe for detection of wild-type (SEQ ID No. 62) and the probe for detection of variant (SEQ ID No. 67) shown in Table 8, for G857A polymorphism. The probe for detection of G590A polymorphism was a minus chain, while the probe for detection of G837A polymorphism was a plus chain. The 3' terminal of the nucleotide probe was thiol-modified for immobilization on an electrode.

Nucleotide Probe-Immobilized Support:

A nucleotide probe-immobilized support was prepared in a similar manner to the test 5-1.

The nucleotide probes were immobilized on the following electrodes respectively:

Electrodes 1-2: negative probe (SEQ ID No. 51)
Electrodes 3-4: wild-type nucleotide probe 26mer (SEQ ID No. 54)
Electrodes 5-6: variant nucleotide probe 27mer (SEQ ID No. 59)
Electrodes 7-8: wild-type nucleotide probe 23mer (SEQ ID No. 62)
Electrodes 9-10: variant nucleotide probe 26mer (SEQ ID No. 67)

Hybridization between amplification products and nucleotide probe, and detection thereof:

The test was performed in a similar manner to the test 7.

[Test 8-1: Results]

Figure 19:
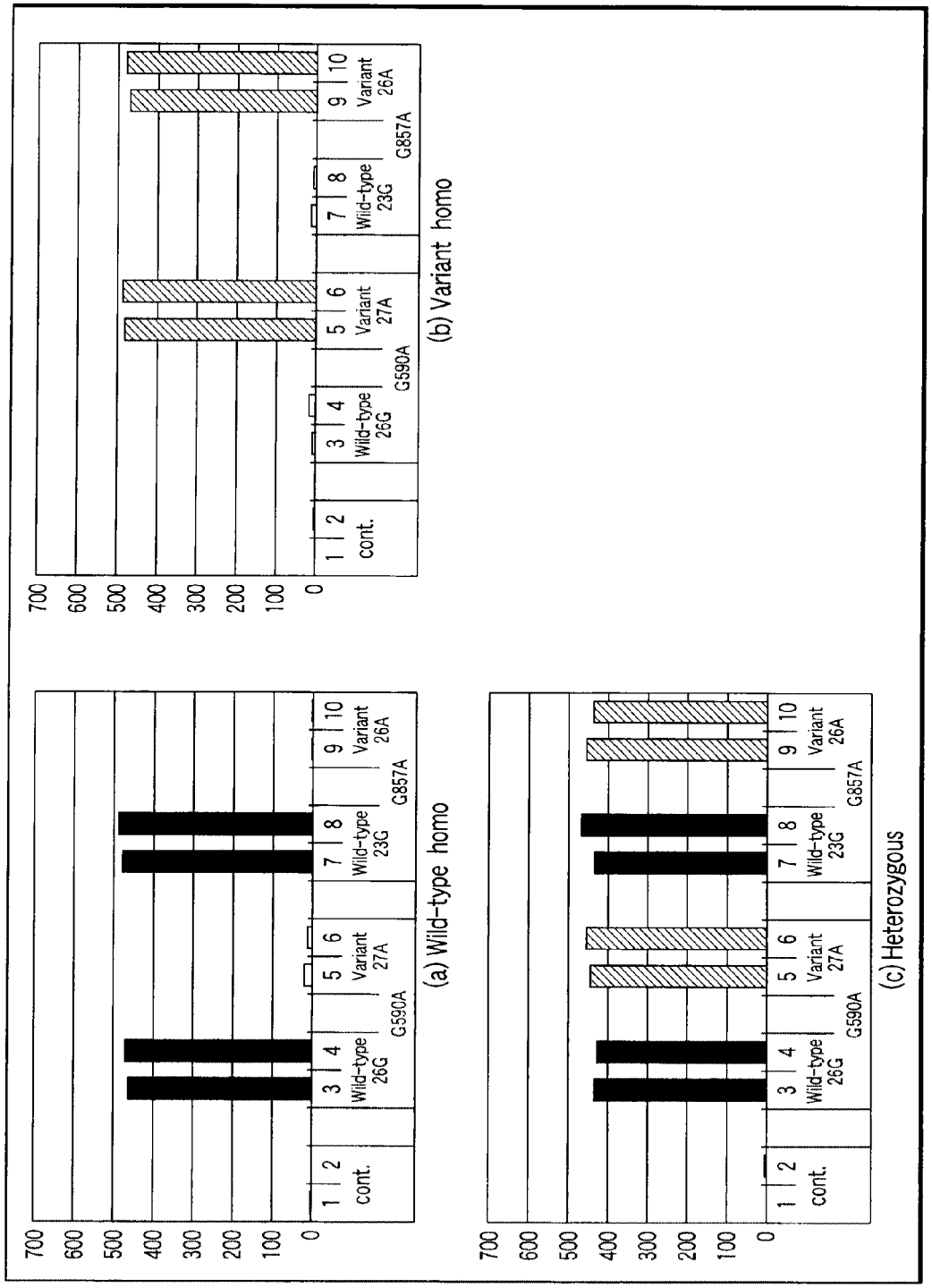
FIG. 19 shows graphs indicating the results of simultaneous amplification of G590A and G857A.

The results are summarized in FIG. 19. The probe for detection of G590A wild-type (SEQ ID No. 54), the probe for detection of variant (SEQ ID No. 59), the probe for detection of G857A wild-type (SEQ ID No. 62), and the probe for detection of variant (SEQ ID No. 67) provided the ideal detection results.

<Analyte Sample>

The analyte sample subjected to the present invention is not particularly limited, and may be, for example, human blood, serum, leukocyte, hair root, or oral mucous membranes. Nucleotide components are extracted from the analyte sample, to prepare a sample solution subjected to the test for detecting a target nucleotide. The extraction method is not particularly limited, and, for example, a commercially available nucleotide extraction tool such as QIAamp (manufactured by QIAGEN) or Sumai test (Sumitomo Metal Industries, Ltd.) may be used.

<Kit>

Another aspect of the present invention provides a kit including the primer set described above for the LAMP method for use in the detection method according to the present invention. The kit may optionally contain, for example, a chain-substituting DNA polymerase, a synthesis substrate, and a buffer solution.

In another aspect, the invention provides a nucleotide probe for detection of the amplification products amplified with the primer set according to the invention. The present invention also provides a nucleotide probe-immobilized support on which the nucleotide probe according to the invention was immobilized. The probe-immobilized support is provided preferably as a DNA chip or DNA microarray.

The kit according to the invention can also include the nucleotide probe or the nucleotide probe-immobilized support additionally.

In another aspect, the present invention, provided is a method of detecting single-nucleotide polymorphisms G590A, G857A and T341C of NAT2 simultaneously. In the present aspect, G590A, G857A and T341C are amplified as described above, separately, and then the amplification products are mixed to prepare a liquid mixture. The liquid mixture is subjected to the detection as described above. In the present aspect, it is possible to detect the genotypes of G590A, G857A and T341C simultaneously.

Examples

[Simultaneous Detection of G590A, G857A, and T341C]

A test for simultaneous detection of G590A, G857A, and T341C was performed. A human genome was amplified at 63° C. for 1 hour, respectively by using the nucleotide primer set 9 for detection of G590A (test 1-2), the nucleotide primer set 5 for detection of G857A (test 2), or the nucleotide primer sets 6 and 10 for detection of T341C (test 3). The human genomes used were three kinds of human genomes determined to be wild homozygous, variant homozygous and heterozygous respectively by PCR-RFLP analysis or sequence analysis. After the amplification reaction, three amplification products were mixed, to prepare a mixed reaction solution.

Nucleotide Probe:

The mixed reaction solution was subjected to the detection with the nucleotide probe for G590A, the nucleotide probe for G857A, and the nucleotide probe for T341C.

The nucleotide probes were as follows:

G590A wild-type nucleotide probe (SEQ ID No. 54), variant nucleotide probe (SEQ ID No. 59), G857A wild-type nucleotide probe (SEQ ID No. 62), variant nucleotide probe (SEQ ID No. 67), T341C wild-type nucleotide probe (SEQ ID No. 72), and variant nucleotide probe (SEQ ID No. 76).

All the nucleotide probes were plus chain, and the 3' terminal of the nucleotide probe was thiol-modified.

Preparation of probe nucleotide-immobilized electrode:

A probe nucleotide-immobilized electrode was prepared in a manner similar to the method described in the test 5-1 above.

The nucleotide probes were immobilized on the following electrodes respectively:

Electrodes 1-2: negative probe (SEQ ID No. 51)
Electrodes 3-4: G590A wild-type nucleotide probe 26mer (SEQ ID No. 54)
Electrodes 5-6: G590A variant nucleotide probe 27mer (SEQ ID No. 59)
Electrodes 7-8: G857A wild-type nucleotide probe 23mer (SEQ ID No. 62)
Electrodes 9-10: G857A variant nucleotide probe 26mer (SEQ ID No. 67)
Electrodes 11-12: T341C wild-type nucleotide probe 18mer (SEQ ID No. 72)
Electrodes 13-14: T341C variant nucleotide probe 17mer (SEQ ID No. 76)

Hybridization between amplification products and nucleotide probe, and detection thereof:

The test was performed in a manner similar to the test 7.

[Results]

Figure 20B:
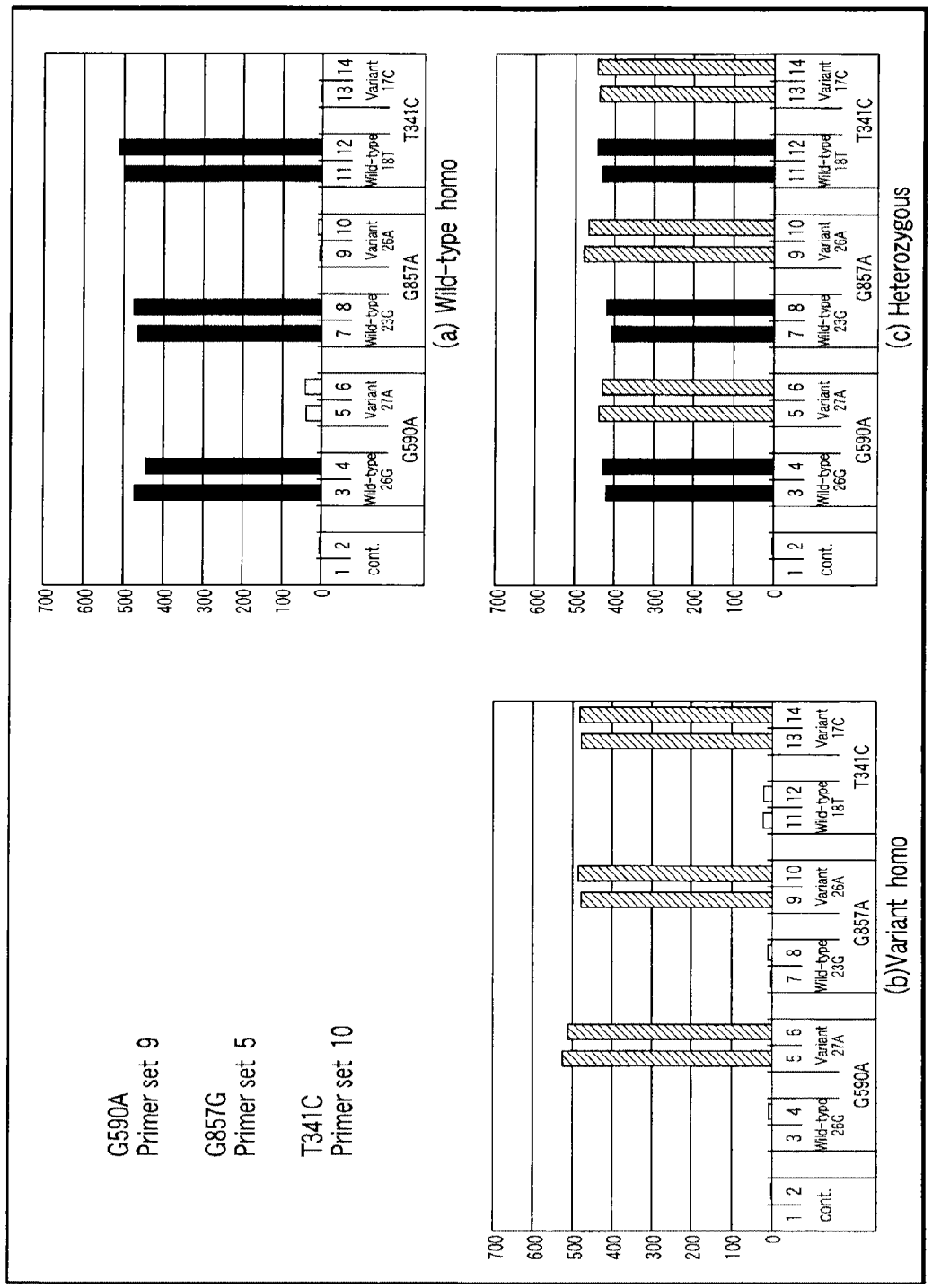
FIG. 20B shows graphs indicating the results of simultaneous detection of G590A, G857A, and T341A (primer set 10 for T341C).

The results are summarized in FIG. 20. FIG. 20A shows the results obtained by using the primer sets 9, 5, and 6, while FIG. 20B, by using the primer sets 9, 5, and 10. An ideal detection pattern was obtained with each of G590A, G857A, and T341C. The results showed that it was possible to detect G590A, G857A, and T341C simultaneously by using a DNA chip according to the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A nucleotide primer set for LAMP amplification, used for detecting a genotype of a single-nucleotide polymorphism G590A of the N-acetyltransferase 2 (NAT2) gene, wherein the nucleotide primer set comprises:
   an FIP and BIP primer set selected from the group consisting of: SEQ ID NO: 2 and SEQ ID NO: 7; SEQ ID NO: 5 and SEQ ID NO: 7; SEQ ID NO: 6 and SEQ ID NO: 7; SEQ ID NO: 10 and SEQ ID NO: 13; SEQ ID NO: 10 and SEQ ID NO: 14; SEQ ID NO: 15 and SEQ ID NO: 11; SEQ ID NO: 15 and SEQ ID NO: 12; SEQ ID NO: 15 and SEQ ID NO: 13; SEQ ID NO: 15 and SEQ ID NO: 14; SEQ ID NO: 16 and SEQ ID NO: 11; SEQ ID NO: 16 and SEQ ID NO: 12; SEQ ID NO: 16 and SEQ ID NO: 13; SEQ ID NO: 16 and SEQ ID NO: 14; SEQ ID NO: 17 and SEQ ID NO: 13; and SEQ ID NO: 17 and SEQ ID NO: 14;
   an F3 primer comprising a sequence of SEQ ID No: 8 in the case that the FIP and BIP primer set is selected from the group consisting of: SEQ ID NO: 2 and SEQ ID NO: 7; SEQ ID NO: 5 and SEQ ID NO: 7; and SEQ ID NO: 6 and SEQ ID NO: 7, or a sequence of SEQ ID No: 18 in the case that the FIP and BIP primer set is selected from the group consisting of: SEQ ID NO: 10 and SEQ ID NO: 13; SEQ ID NO: 10 and SEQ ID NO: 14; SEQ ID NO: 15 and SEQ ID NO: 11; SEQ ID NO: 15 and SEQ ID NO: 12; SEQ ID NO: 15 and SEQ ID NO: 13; SEQ ID NO: 15 and SEQ ID NO: 14; SEQ ID NO: 16 and SEQ ID NO: 11; SEQ ID NO: 16 and SEQ ID NO: 12; SEQ ID NO: 16 and SEQ ID NO: 13; SEQ ID NO: 16 and SEQ ID NO: 14; SEQ ID NO: 17 and SEQ ID NO: 13; and SEQ ID NO: 17 and SEQ ID NO: 14; and
   a B3 primer comprising a sequence of SEQ ID No: 9 in the case that the FIP and BIP primer set is selected from the group consisting of: SEQ ID NO: 2 and SEQ ID NO: 7; SEQ ID NO: 5 and SEQ ID NO: 7; and SEQ ID NO: 6 and SEQ ID NO: 7, or a sequence of SEQ ID No: 19 in the case that the FIP and BIP primer set is selected from the group consisting of: SEQ ID NO: 10 and SEQ ID NO: 13; SEQ ID NO: 10 and SEQ ID NO: 14; SEQ ID NO: 15 and SEQ ID NO: 11; SEQ ID NO: 15 and SEQ ID NO: 12; SEQ ID NO: 15 and SEQ ID NO: 13; SEQ ID NO: 15 and SEQ ID NO: 14; SEQ ID NO: 16 and SEQ ID NO: 11; SEQ ID NO: 16 and SEQ ID NO: 12; SEQ ID NO: 16 and SEQ ID NO: 13; SEQ ID NO: 16 and SEQ ID NO: 14; SEQ ID NO: 17 and SEQ ID NO: 13; and SEQ ID NO: 17 and SEQ ID NO: 14, 2. The nucleotide primer set according to claim 1, wherein the FIP and BIP primer set is selected from the group consisting of: SEQ ID NO: 5 and SEQ ID NO: 7; SEQ ID NO: 6 and SEQ ID NO:7; and SEQ ID NO: 15 and SEQ ID NO:13.

3. The nucleotide primer set according to claim 1, wherein the FIP and BIP primer set is SEQ ID NO: 15 and SEQ ID NO: 13.

4. A nucleotide primer set for LAMP amplification, used for detecting a genotype of a single-nucleotide polymorphism G857A of the NAT2 gene, wherein the nucleotide primer set comprises:
   an FIP and BIP primer set selected from the group consisting of: SEQ ID NO: 20 and SEQ ID NO: 21; SEQ ID NO: 20 and SEQ ID NO: 22; SEQ ID NO: 20 and SEQ ID NO: 23; and SEQ ID NO: 20 and SEQ ID NO: 25;
   an F3 primer comprising a sequence of SEQ ID No: 27; and
   a B3 primer comprising a sequence of SEQ ID No: 28.

5. A nucleotide primer set for LAMP amplification, used for detecting a genotype of a single-nucleotide polymorphism T341C of the NAT2 gene, wherein the nucleotide primer set comprises:
   an FIP and BIP primer set selected from the group consisting of SEQ ID NO: 33 and SEQ ID NO: 30; SEQ ID NO: 33 and SEQ ID NO: 31; SEQ ID NO: 33 and SEQ ID NO: 32; SEQ ID NO: 34 and SEQ ID NO: 30; SEQ ID NO: 34 and SEQ ID NO: 31; SEQ ID NO: 34 and SEQ ID NO: 32; SEQ ID NO: 35 and SEQ ID NO: 32; SEQ ID NO: 36 and SEQ ID NO: 32; SEQ ID NO: 37 and SEQ ID NO: 32; and SEQ ID NO: 38 and SEQ ID NO: 32;

an F3 primer comprising a sequence of SEQ ID No: 39 in the case that the FIP and BIP primer set is selected from the group consisting of SEQ ID NO: 33 and SEQ ID NO: 30; SEQ ID NO: 33 and SEQ ID NO: 31; SEQ ID NO: 33 and SEQ ID NO: 32; SEQ ID NO: 34 and SEQ ID NO: 30; SEQ ID NO: 34 and SEQ ID NO: 31; and SEQ ID NO: 38 and SEQ ID NO: 32, or a sequence of SEQ ID No: 41 in the case that the FIP and BIP primer set is selected from the group consisting of: SEQ ID NO: 34 and SEQ ID NO: 32; SEQ ID NO: 35 and SEQ ID NO: 32; SEQ ID NO: 36 and SEQ ID NO: 32; and SEQ ID NO: 37 and SEQ ID NO: 32; and a B3 primer comprising a sequence of SEQ ID No: 40.

6. The nucleotide primer set according to claim 5, wherein the FIP and BIP primer set is selected from the group consisting of: SEQ ID NO: 33 and SEQ ID NO: 32; SEQ ID NO: 34 and SEQ ID NO: 32; SEQ ID NO: 37 and SEQ ID NO: 32; and SEQ ID NO: 38 and SEQ ID NO: 32.

7. The nucleotide primer set according to claim 5, wherein the FIP and BIP primer set is selected from the group consisting of: SEQ ID NO: 34 and SEQ ID NO: 32; and SEQ ID NO: 38 and SEQ ID NO: 32.

8. A nucleotide primer set for LAMP amplification, used for detecting genotypes of single-nucleotide polymorphisms G590A and G857A of the NAT2 gene, wherein the nucleotide primer set comprises:

an FIP and BIP primer set selected from SEQ ID NO: 42 and SEQ ID NO: 43; SEQ ID NO: 42 and SEQ ID NO: 44; SEQ ID NO: 45 and SEQ ID NO: 43; SEQ ID NO: 45 and SEQ ID NO: 46; SEQ ID NO: 47 and SEQ ID NO: 43; SEQ ID NO: 48 and SEQ ID NO: 43; SEQ ID NO: 48 and SEQ ID NO: 46; and SEQ ID NO: 48 and SEQ ID NO: 44;

an F3 primer comprising a sequence of SEQ ID No: 49; and a B3 primer comprising a sequence of SEQ ID No: 50.

9. The nucleotide primer set according to claim 8, wherein the FIP and BIP primer set is selected from the group consisting of: SEQ ID NO: 42 and SEQ ID NO: 43; SEQ ID NO: 48 and SEQ ID NO: 43; SEQ ID NO: 48 and SEQ ID NO: 46; and SEQ ID NO: 48 and SEQ ID NO: 44.

10. The nucleotide primer set according to claim 8, wherein the FIP and BIP primer set is SEQ ID NO: 48 and SEQ ID NO: 43.

11. A kit used for detecting a genotype of the single-nucleotide polymorphism G590A of the NAT2 gene, comprising the nucleotide primer set according to claim 1;
a wild-type nucleotide probe; and
a variant nucleotide probe;
wherein:
the wild-type nucleotide probe has a sequence of SEQ ID No: 53 or 54, or a sequence complementary thereto, and
the variant nucleotide probe has a sequence of SEQ ID NO: 59 or a sequence complementary thereto.

12. The kit according to claim 11, wherein the probes are immobilized on a support.

13. A kit used for detecting a genotype of the single-nucleotide polymorphism G857A of the NAT2 gene, comprising the nucleotide primer set according to claim 4;
a wild-type nucleotide probe; and
a variant nucleotide probe;
wherein:
the wild-type nucleotide probe has a sequence of SEQ ID No: 62, 63, or 64, or a sequence complementary thereto, and
the variant nucleotide probe has a sequence of SEQ ID No: 67, 68 or 69, or a sequence complementary thereto.

14. The kit according to claim 13, wherein the probes are immobilized on a support.

15. A kit used for detecting a genotype of the single-nucleotide polymorphism T341C of the NAT2 gene, comprising the nucleotide primer set according to claim 5;
a wild-type nucleotide probe; and
a variant nucleotide probe;
wherein:
the wild-type nucleotide probe has a sequence of SEQ ID No: 72 or 73, or a sequence complementary thereto, and
the variant nucleotide probe has a sequence of SEQ ID No: 76, 77 or 78, or a sequence complementary thereto.

16. The kit according to claim 15, wherein the probes are immobilized on a support.

17. A kit used for detecting a genotype of single-nucleotide polymorphisms G590A and G857A of the NAT2 gene, comprising the nucleotide primer set according to claim 8;
a wild-type nucleotide probe for G590A;
a variant nucleotide probe for G590A;
a wild-type nucleotide probe for G857A; and
a variant nucleotide probe for G857A;
wherein:
the wild-type nucleotide probe for G590A has a sequence of SEQ ID No: 54 or a sequence complementary thereto;
the variant nucleotide probe for G590A has a sequence of SEQ ID No: 59 or a sequence complementary thereto;
the wild-type nucleotide probe for G857A has a sequence of SEQ ID No: 62 or a sequence complementary thereto; and
the variant nucleotide probe for G857A has a sequence of SEQ ID No: 67 or a sequence complementary thereto.

18. The kit according to claim 17, wherein the probes are immobilized on a support.

* * * * *

SEQUENCE LISTING

<160> NUMBER OF SEQ ID NOS: 82

<210> SEQ ID NO 1
<211> LENGTH: 55
<212> TYPE: DNA
<213> ORGANISM: Artificial
<220> FEATURE:
<223> OTHER INFORMATION: G590A Primer FIP-1

<400> SEQUENCE: 1
cgtctgcagg tatgtattca tagactcaaa aaatatactt atttacgctt gaacc    55

<210> SEQ ID NO 2
<211> LENGTH: 54
<212> TYPE: DNA
<213> ORGANISM: Artificial
<220> FEATURE:
<223> OTHER INFORMATION: G591A Primer FIP-2

<400> SEQUENCE: 2
cgtctgcagg tatgtattca tagactcaac accaaaaaat atacttattt acgc    54

<210> SEQ ID NO 3
<211> LENGTH: 55
<212> TYPE: DNA
<213> ORGANISM: Artificial
<220> FEATURE:
<223> OTHER INFORMATION: G592A Primer FIP-3

<400> SEQUENCE: 3
cgtctgcagg tatgtattca tagactcaac aaagaagaaa caccaaaaaa tatac    55

<210> SEQ ID NO 4
<211> LENGTH: 53
<212> TYPE: DNA
<213> ORGANISM: Artificial
<220> FEATURE:
<223> OTHER INFORMATION: G593A Primer FIP-4

<400> SEQUENCE: 4
cgtctgcagg tatgtattca tagactcaac tcctgccaaa gaagaaacac caa    53

<210> SEQ ID NO 5
<211> LENGTH: 54
<212> TYPE: DNA
<213> ORGANISM: Artificial
<220> FEATURE:
<223> OTHER INFORMATION: G594A Primer FIP-5

<400> SEQUENCE: 5
gcaggtatgt attcatagac tcaaaatctc accaaaaaat atacttattt acgc    54

<210> SEQ ID NO 6
<211> LENGTH: 49
<212> TYPE: DNA
<213> ORGANISM: Artificial
<220> FEATURE:
<223> OTHER INFORMATION: G595A Primer FIP-6

<400> SEQUENCE: 6
ggagacgtct gcaggtatgt attccaccaa aaaatatact tatttacgc    49

```
<210> SEQ ID NO 7
<211> LENGTH: 50
<212> TYPE: DNA
<213> ORGANISM: Artificial
<220> FEATURE:
<223> OTHER INFORMATION: G596A Primer BIP-1

<400> SEQUENCE: 7
ataaccacat cattttgttc cttgcatgaa ttttctatag gtgaggatga            50

<210> SEQ ID NO 8
<211> LENGTH: 27
<212> TYPE: DNA
<213> ORGANISM: Artificial
<220> FEATURE:
<223> OTHER INFORMATION: G597A Primer F3

<400> SEQUENCE: 8
caaacaaaga atttcttaat tctcatc                                    27

<210> SEQ ID NO 9
<211> LENGTH: 21
<212> TYPE: DNA
<213> ORGANISM: Artificial
<220> FEATURE:
<223> OTHER INFORMATION: G598A Primer B3

<400> SEQUENCE: 9
cgaccagatc tgtattgtct t                                          21

<210> SEQ ID NO 10
<211> LENGTH: 48
<212> TYPE: DNA
<213> ORGANISM: Artificial
<220> FEATURE:
<223> OTHER INFORMATION: G590A Primer FIP-1

<400> SEQUENCE: 10
gtttgtaata tactgctctc tcctggcttg acagaagaga gaggaatc             48

<210> SEQ ID NO 11
<211> LENGTH: 54
<212> TYPE: DNA
<213> ORGANISM: Artificial
<220> FEATURE:
<223> OTHER INFORMATION: G590A Primer BIP-1

<400> SEQUENCE: 11
gaaacaccaa aaatatact tatttacgcc tgcaggtatg tattcataga ctca       54

<210> SEQ ID NO 12
<211> LENGTH: 57
<212> TYPE: DNA
<213> ORGANISM: Artificial
<220> FEATURE:
<223> OTHER INFORMATION: G590A Primer BIP-2

<400> SEQUENCE: 12
gaaacaccaa aaatatact tatttacgcc aggtatgtat tcatagactc aaaatct    57

<210> SEQ ID NO 13
<211> LENGTH: 49
<212> TYPE: DNA
<213> ORGANISM: Artificial
<220> FEATURE:
<223> OTHER INFORMATION: G590A Primer BIP-3
```

```
<400> SEQUENCE: 13
caccaaaaaa tacttatt tacgcctgca ggtatgtatt catagactc                    49

<210> SEQ ID NO 14
<211> LENGTH: 52
<212> TYPE: DNA
<213> ORGANISM: Artificial
<220> FEATURE:
<223> OTHER INFORMATION: G590A Primer BIP-4

<400> SEQUENCE: 14
caccaaaaaa tacttatt tacgccaggt atgtattcat agactcaaaa tc                52

<210> SEQ ID NO 15
<211> LENGTH: 45
<212> TYPE: DNA
<213> ORGANISM: Artificial
<220> FEATURE:
<223> OTHER INFORMATION: G590A Primer FIP-2

<400> SEQUENCE: 15
gtttgtaata tactgctctc tcctgccttg cattttctgc ttgac                      45

<210> SEQ ID NO 16
<211> LENGTH: 49
<212> TYPE: DNA
<213> ORGANISM: Artificial
<220> FEATURE:
<223> OTHER INFORMATION: G590A Primer FIP-3

<400> SEQUENCE: 16
gaaattcttt gtttgtaata tactgcgctt gacagaagag agaggaatc                  49

<210> SEQ ID NO 17
<211> LENGTH: 46
<212> TYPE: DNA
<213> ORGANISM: Artificial
<220> FEATURE:
<223> OTHER INFORMATION: G590A Primer FIP-4

<400> SEQUENCE: 17
gaaattcttt gtttgtaata tactgcccctt gcattttctg cttgac                    46

<210> SEQ ID NO 18
<211> LENGTH: 18
<212> TYPE: DNA
<213> ORGANISM: Artificial
<220> FEATURE:
<223> OTHER INFORMATION: G590A Primer F3

<400> SEQUENCE: 18
ctgggaagga tcagcctc                                                    18

<210> SEQ ID NO 19
<211> LENGTH: 20
<212> TYPE: DNA
<213> ORGANISM: Artificial
<220> FEATURE:
<223> OTHER INFORMATION: G590A Primer B3

<400> SEQUENCE: 19
aaatgaagat gttggagacg                                                  20
```

-continued

```
<210> SEQ ID NO 20
<211> LENGTH: 46
<212> TYPE: DNA
<213> ORGANISM: Artificial
<220> FEATURE:
<223> OTHER INFORMATION: G857A Primer FIP-1

<400> SEQUENCE: 20
agcacttctt caacctcttc ctctaaagac aatacagatc tggtcg          46

<210> SEQ ID NO 21
<211> LENGTH: 47
<212> TYPE: DNA
<213> ORGANISM: Artificial
<220> FEATURE:
<223> OTHER INFORMATION: G857A Primer BIP-1

<400> SEQUENCE: 21
ccttggggag aaatctcgtg cgttccttat tctaaatagt aagggat         47

<210> SEQ ID NO 22
<211> LENGTH: 47
<212> TYPE: DNA
<213> ORGANISM: Artificial
<220> FEATURE:
<223> OTHER INFORMATION: G857A Primer BIP-2

<400> SEQUENCE: 22
gagaaatctc gtgcccaaac cgttccttat tctaaatagt aagggat         47

<210> SEQ ID NO 23
<211> LENGTH: 44
<212> TYPE: DNA
<213> ORGANISM: Artificial
<220> FEATURE:
<223> OTHER INFORMATION: G857A Primer BIP-3

<400> SEQUENCE: 23
gaaatctcgt gcccaaaccc aagggtttat tttgttcctt attc            44

<210> SEQ ID NO 24
<211> LENGTH: 44
<212> TYPE: DNA
<213> ORGANISM: Artificial
<220> FEATURE:
<223> OTHER INFORMATION: G857A Primer BIP-4

<400> SEQUENCE: 24
gagaaatctc gtgcccaaac gttccttatt ctaaatagta aggg            44

<210> SEQ ID NO 25
<211> LENGTH: 43
<212> TYPE: DNA
<213> ORGANISM: Artificial
<220> FEATURE:
<223> OTHER INFORMATION: G857A Primer BIP-5

<400> SEQUENCE: 25
ccttggggag aaatctcgtg agggtttatt ttgttcctta ttc             43

<210> SEQ ID NO 26
<211> LENGTH: 43
<212> TYPE: DNA
<213> ORGANISM: Artificial
<220> FEATURE:
<223> OTHER INFORMATION: G857A Primer BIP-6
```

<400> SEQUENCE: 26
ggggagaaat ctcgtgccca agggtttatt ttgttcctta ttc        43

<210> SEQ ID NO 27
<211> LENGTH: 17
<212> TYPE: DNA
<213> ORGANISM: Artificial
<220> FEATURE:
<223> OTHER INFORMATION: G857A Primer F3

<400> SEQUENCE: 27
gtgggcttca tcctcac        17

<210> SEQ ID NO 28
<211> LENGTH: 23
<212> TYPE: DNA
<213> ORGANISM: Artificial
<220> FEATURE:
<223> OTHER INFORMATION: G857A Primer B3

<400> SEQUENCE: 28
tgataattag tgagttgggt gat        23

<210> SEQ ID NO 29
<211> LENGTH: 39
<212> TYPE: DNA
<213> ORGANISM: Artificial
<220> FEATURE:
<223> OTHER INFORMATION: T341C Primer FIP-1

<400> SEQUENCE: 29
ctgtatttgt taactggagg ctctgaccac aatcggttc        39

<210> SEQ ID NO 30
<211> LENGTH: 39
<212> TYPE: DNA
<213> ORGANISM: Artificial
<220> FEATURE:
<223> OTHER INFORMATION: T341C Primer BIP-1

<400> SEQUENCE: 30
catggttcac cttctcctgc agacccagca tygacaatg        39

<210> SEQ ID NO 31
<211> LENGTH: 37
<212> TYPE: DNA
<213> ORGANISM: Artificial
<220> FEATURE:
<223> OTHER INFORMATION: T341C Primer BIP-2

<400> SEQUENCE: 31
catggttcac cttctcctgg agcttccaga cccagca        37

<210> SEQ ID NO 32
<211> LENGTH: 37
<212> TYPE: DNA
<213> ORGANISM: Artificial
<220> FEATURE:
<223> OTHER INFORMATION: T341C Primer BIP-3

<400> SEQUENCE: 32
catggttcac cttctcctga gcttccagac ccagcat        37

-continued

```
<210> SEQ ID NO 33
<211> LENGTH: 40
<212> TYPE: DNA
<213> ORGANISM: Artificial
<220> FEATURE:
<223> OTHER INFORMATION: T341C Primer FIP-2

<400> SEQUENCE: 33
tgtggtctga aaccgattg ggtgtctcca ggtcaatcaa                    40

<210> SEQ ID NO 34
<211> LENGTH: 41
<212> TYPE: DNA
<213> ORGANISM: Artificial
<220> FEATURE:
<223> OTHER INFORMATION: T341C Primer FIP-3

<400> SEQUENCE: 34
gaaaaccgat tgtggtcaga gggtgtctcc aggtcaatca a                 41

<210> SEQ ID NO 35
<211> LENGTH: 42
<212> TYPE: DNA
<213> ORGANISM: Artificial
<220> FEATURE:
<223> OTHER INFORMATION: T341C Primer FIP-4

<400> SEQUENCE: 35
ttgattgacc tggagacacg gcttagaggc tatttttgat ca                42

<210> SEQ ID NO 36
<211> LENGTH: 41
<212> TYPE: DNA
<213> ORGANISM: Artificial
<220> FEATURE:
<223> OTHER INFORMATION: T341C Primer FIP-5

<400> SEQUENCE: 36
ttgattgacc tggagacagg cttagaggct attttgatc a                  41

<210> SEQ ID NO 37
<211> LENGTH: 44
<212> TYPE: DNA
<213> ORGANISM: Artificial
<220> FEATURE:
<223> OTHER INFORMATION: T341C Primer FIP-6

<400> SEQUENCE: 37
ttgattgacc tggagacacg gcttagaggc tatttttgat caca              44

<210> SEQ ID NO 38
<211> LENGTH: 43
<212> TYPE: DNA
<213> ORGANISM: Artificial
<220> FEATURE:
<223> OTHER INFORMATION: T341C Primer FIP-7

<400> SEQUENCE: 38
ttgattgacc tggagacacg cttagaggct attttgatc aca                43

<210> SEQ ID NO 39
<211> LENGTH: 24
<212> TYPE: DNA
<213> ORGANISM: Artificial
<220> FEATURE:
<223> OTHER INFORMATION: T341C Primer F3-1
```

```
<400> SEQUENCE: 39
gaggctattt ttgatcacat tgta                                          24

<210> SEQ ID NO 40
<211> LENGTH: 18
<212> TYPE: DNA
<213> ORGANISM: Artificial
<220> FEATURE:
<223> OTHER INFORMATION: T341C Primer B3-1

<400> SEQUENCE: 40
ggctgccaca tctgggag                                                 18

<210> SEQ ID NO 41
<211> LENGTH: 18
<212> TYPE: DNA
<213> ORGANISM: Artificial
<220> FEATURE:
<223> OTHER INFORMATION: T341C Primer F3-2

<400> SEQUENCE: 41
tgtgggcaag ccatggag                                                 18

<210> SEQ ID NO 42
<211> LENGTH: 43
<212> TYPE: DNA
<213> ORGANISM: Artificial
<220> FEATURE:
<223> OTHER INFORMATION: G590A Primer FIP-1

<400> SEQUENCE: 42
ggagacgtct gcaggtatgt attcacttat ttacgcttga acc                     43

<210> SEQ ID NO 43
<211> LENGTH: 47
<212> TYPE: DNA
<213> ORGANISM: Artificial
<220> FEATURE:
<223> OTHER INFORMATION: G590A Primer BIP-1

<400> SEQUENCE: 43
gatttccttg gggagaaatc tcgtgacaca agggtttatt ttgttcc                 47

<210> SEQ ID NO 44
<211> LENGTH: 43
<212> TYPE: DNA
<213> ORGANISM: Artificial
<220> FEATURE:
<223> OTHER INFORMATION: G590A Primer BIP-3

<400> SEQUENCE: 44
ggggagaaat ctcgtgccca agggtttatt ttgttcctta ttc                     43

<210> SEQ ID NO 45
<211> LENGTH: 48
<212> TYPE: DNA
<213> ORGANISM: Artificial
<220> FEATURE:
<223> OTHER INFORMATION: G590A Primer FIP-2

<400> SEQUENCE: 45
gagacgtctg caggtatgta ttcatccaaa aaatatactt atttacgc                48
```

```
<210> SEQ ID NO 46
<211> LENGTH: 47
<212> TYPE: DNA
<213> ORGANISM: Artificial
<220> FEATURE:
<223> OTHER INFORMATION: G590A Primer BIP-2

<400> SEQUENCE: 46
cttggggaga aatctcgtgc cccatacaca agggtttatt ttgttcc        47

<210> SEQ ID NO 47
<211> LENGTH: 48
<212> TYPE: DNA
<213> ORGANISM: Artificial
<220> FEATURE:
<223> OTHER INFORMATION: G590A Primer FIP-3

<400> SEQUENCE: 47
cgtctgcagg tatgtattca tagacccaaa aaatatactt atttacgc        48

<210> SEQ ID NO 48
<211> LENGTH: 49
<212> TYPE: DNA
<213> ORGANISM: Artificial
<220> FEATURE:
<223> OTHER INFORMATION: G590A Primer FIP-4

<400> SEQUENCE: 48
ctgcaggtat gtattcatag actccaccaa aaaatatact tatttacgc       49

<210> SEQ ID NO 49
<211> LENGTH: 21
<212> TYPE: DNA
<213> ORGANISM: Artificial
<220> FEATURE:
<223> OTHER INFORMATION: G590A Primer F3

<400> SEQUENCE: 49
tctcatctcc tgccaaagaa g                                      21

<210> SEQ ID NO 50
<211> LENGTH: 24
<212> TYPE: DNA
<213> ORGANISM: Artificial
<220> FEATURE:
<223> OTHER INFORMATION: G590A Primer B3

<400> SEQUENCE: 50
agttgataat tagtgagttg ggtg                                   24

<210> SEQ ID NO 51
<211> LENGTH: 14
<212> TYPE: DNA
<213> ORGANISM: Artificial
<220> FEATURE:
<223> OTHER INFORMATION: Negative Controle Probe

<400> SEQUENCE: 51
gtgctgcagg tgcg                                              14

<210> SEQ ID NO 52
<211> LENGTH: 17
<212> TYPE: DNA
<213> ORGANISM: Artificial
<220> FEATURE:
<223> OTHER INFORMATION: G590A Wild Type Probe
```

```
<400> SEQUENCE: 52
gaacctcgaa caattga                                                    17

<210> SEQ ID NO 53
<211> LENGTH: 21
<212> TYPE: DNA
<213> ORGANISM: Artificial
<220> FEATURE:
<223> OTHER INFORMATION: G590A Wild Type Probe

<400> SEQUENCE: 53
ttgaacctcg aacaattgaa g                                               21

<210> SEQ ID NO 54
<211> LENGTH: 26
<212> TYPE: DNA
<213> ORGANISM: Artificial
<220> FEATURE:
<223> OTHER INFORMATION: G590A Wild Type Probe

<400> SEQUENCE: 54
ttgaacctcg aacaattgaa gatttt                                          26

<210> SEQ ID NO 55
<211> LENGTH: 29
<212> TYPE: DNA
<213> ORGANISM: Artificial
<220> FEATURE:
<223> OTHER INFORMATION: G590A Wild Type Probe

<400> SEQUENCE: 55
ttgaacctcg aacaattgaa gattttgag                                       29

<210> SEQ ID NO 56
<211> LENGTH: 19
<212> TYPE: DNA
<213> ORGANISM: Artificial
<220> FEATURE:
<223> OTHER INFORMATION: G590A Mutation Type Probe

<400> SEQUENCE: 56
gaacctcaaa caattgaag                                                  19

<210> SEQ ID NO 57
<211> LENGTH: 21
<212> TYPE: DNA
<213> ORGANISM: Artificial
<220> FEATURE:
<223> OTHER INFORMATION: G590A Mutation Type Probe

<400> SEQUENCE: 57
gaacctcaaa caattgaaga t                                               21

<210> SEQ ID NO 58
<211> LENGTH: 23
<212> TYPE: DNA
<213> ORGANISM: Artificial
<220> FEATURE:
<223> OTHER INFORMATION: G590A Mutation Type Probe

<400> SEQUENCE: 58
ttgaacctca aacaattgaa gat                                             23
```

```
<210> SEQ ID NO 59
<211> LENGTH: 27
<212> TYPE: DNA
<213> ORGANISM: Artificial
<220> FEATURE:
<223> OTHER INFORMATION: G590A Mutation Type Probe

<400> SEQUENCE: 59
ttgaacctca aacaattgaa gattttg                                27

<210> SEQ ID NO 60
<211> LENGTH: 30
<212> TYPE: DNA
<213> ORGANISM: Artificial
<220> FEATURE:
<223> OTHER INFORMATION: G590A Mutation Type Probe

<400> SEQUENCE: 60
ttgaacctca aacaattgaa gattttgagt                             30

<210> SEQ ID NO 61
<211> LENGTH: 20
<212> TYPE: DNA
<213> ORGANISM: Artificial
<220> FEATURE:
<223> OTHER INFORMATION: G857A Wild Type Probe

<400> SEQUENCE: 61
tggtgatgga tcccttacta                                        20

<210> SEQ ID NO 62
<211> LENGTH: 23
<212> TYPE: DNA
<213> ORGANISM: Artificial
<220> FEATURE:
<223> OTHER INFORMATION: G857A Wild Type Probe

<400> SEQUENCE: 62
cctggtgatg gatcccttac tat                                    23

<210> SEQ ID NO 63
<211> LENGTH: 24
<212> TYPE: DNA
<213> ORGANISM: Artificial
<220> FEATURE:
<223> OTHER INFORMATION: G857A Wild Type Probe

<400> SEQUENCE: 63
cctggtgatg gatcccttac tatt                                   24

<210> SEQ ID NO 64
<211> LENGTH: 25
<212> TYPE: DNA
<213> ORGANISM: Artificial
<220> FEATURE:
<223> OTHER INFORMATION: G857A Wild Type Probe

<400> SEQUENCE: 64
acctggtgat ggatccctta ctatt                                  25

<210> SEQ ID NO 65
<211> LENGTH: 30
<212> TYPE: DNA
<213> ORGANISM: Artificial
<220> FEATURE:
<223> OTHER INFORMATION: G857A Wild Type Probe
```

<400> SEQUENCE: 65
aacctggtga tggatccctt actatttaga                30

<210> SEQ ID NO 66
<211> LENGTH: 22
<212> TYPE: DNA
<213> ORGANISM: Artificial
<220> FEATURE:
<223> OTHER INFORMATION: G857A Mutation Type Probe

<400> SEQUENCE: 66
ctggtgatga atcccttact at                22

<210> SEQ ID NO 67
<211> LENGTH: 26
<212> TYPE: DNA
<213> ORGANISM: Artificial
<220> FEATURE:
<223> OTHER INFORMATION: G857A Mutation Type Probe

<400> SEQUENCE: 67
acctggtgat gaatcccttta ctattt                26

<210> SEQ ID NO 68
<211> LENGTH: 28
<212> TYPE: DNA
<213> ORGANISM: Artificial
<220> FEATURE:
<223> OTHER INFORMATION: G857A Mutation Type Probe

<400> SEQUENCE: 68
aacctggtga tgaatccctt actattta                28

<210> SEQ ID NO 69
<211> LENGTH: 29
<212> TYPE: DNA
<213> ORGANISM: Artificial
<220> FEATURE:
<223> OTHER INFORMATION: G857A Mutation Type Probe

<400> SEQUENCE: 69
aacctggtga tgaatccctt actatttag                29

<210> SEQ ID NO 70
<211> LENGTH: 31
<212> TYPE: DNA
<213> ORGANISM: Artificial
<220> FEATURE:
<223> OTHER INFORMATION: G857A Mutation Type Probe

<400> SEQUENCE: 70
aacctggtga tgaatccctt actatttaga a                31

<210> SEQ ID NO 71
<211> LENGTH: 16
<212> TYPE: DNA
<213> ORGANISM: Artificial
<220> FEATURE:
<223> OTHER INFORMATION: T341C Wild Type Probe

<400> SEQUENCE: 71
ggtgaccatt gacggc                16

```
<210> SEQ ID NO 72
<211> LENGTH: 18
<212> TYPE: DNA
<213> ORGANISM: Artificial
<220> FEATURE:
<223> OTHER INFORMATION: T341C Wild Type Probe

<400> SEQUENCE: 72
aggtgaccat tgacggca                                                 18

<210> SEQ ID NO 73
<211> LENGTH: 19
<212> TYPE: DNA
<213> ORGANISM: Artificial
<220> FEATURE:
<223> OTHER INFORMATION: T341C Wild Type Probe

<400> SEQUENCE: 73
caggtgacca ttgacggca                                                19

<210> SEQ ID NO 74
<211> LENGTH: 20
<212> TYPE: DNA
<213> ORGANISM: Artificial
<220> FEATURE:
<223> OTHER INFORMATION: T341C Wild Type Probe

<400> SEQUENCE: 74
caggtgacca ttgacggcag                                               20

<210> SEQ ID NO 75
<211> LENGTH: 16
<212> TYPE: DNA
<213> ORGANISM: Artificial
<220> FEATURE:
<223> OTHER INFORMATION: T341C Mutation Type Probe

<400> SEQUENCE: 75
aggtgaccac tgacgg                                                   16

<210> SEQ ID NO 76
<211> LENGTH: 17
<212> TYPE: DNA
<213> ORGANISM: Artificial
<220> FEATURE:
<223> OTHER INFORMATION: T341C Mutation Type Probe

<400> SEQUENCE: 76
aggtgaccac tgacggc                                                  17

<210> SEQ ID NO 77
<211> LENGTH: 18
<212> TYPE: DNA
<213> ORGANISM: Artificial
<220> FEATURE:
<223> OTHER INFORMATION: T341C Mutation Type Probe

<400> SEQUENCE: 77
aggtgaccac tgacggca                                                 18

<210> SEQ ID NO 78
<211> LENGTH: 19
<212> TYPE: DNA
<213> ORGANISM: Artificial
<220> FEATURE:
<223> OTHER INFORMATION: T341C Mutation Type Probe
```

<400> SEQUENCE: 78
caggtgacca ctgacggca                                          19

<210> SEQ ID NO 79
<211> LENGTH: 20
<212> TYPE: DNA
<213> ORGANISM: Artificial
<220> FEATURE:
<223> OTHER INFORMATION: T341C Mutation Type Probe

<400> SEQUENCE: 79
caggtgacca ctgacggcag                                         20

<210> SEQ ID NO 80
<211> LENGTH: 16
<212> TYPE: DNA
<213> ORGANISM: Artificial
<220> FEATURE:
<223> OTHER INFORMATION: G590A Primer LB

<400> SEQUENCE: 80
gtgcccaaac ctggtg                                             16

<210> SEQ ID NO 81
<211> LENGTH: 898
<212> TYPE: DNA
<213> ORGANISM: Homo sapiens
<220> FEATURE:
<223> OTHER INFORMATION: NAT1

<400> SEQUENCE: 81
tcttcaacac cagatccgag ctgttcccct tgagaacctt aacatccatt gtggggatgc    60
catggactta ggcttagagg ccattttga tcaagttgtg agaagaaatc ggggtggatg   120
gtgtctccag gtcaatcatc ttctgtactg ggctctgacc actattggtt ttgagaccac   180
gatgttggga gggtatgttt acagcactcc agccaaaaaa tacagcactg gcatgattca   240
ccttctcctg caggtgacca ttgatggcag gaactacatt gtcgatgctg ggtttggacg   300
ctcataccag atgtggcagc ctctggagtt aatttctggg aaggatcagc ctcaggtgcc   360
ttgtgtcttc cgtttgacgg aagagaatgg attctggtat ctagaccaaa tcagaaggga   420
acagtacatt ccaaatgaag aatttcttca ttctgatctc tagaagaca gcaaataccg   480
aaaaatctac tcctttactc ttaagcctcg aacaattgaa gattttgagt ctatgaatac   540
atacctgcag acatctccat catctgtgtt tactagtaaa tcattttgtt ccttgcagac   600
cccagatggg gttcactgtt tggtgggctt caccctcacc cataggagat tcaattataa   660
ggacaataca gatctaatag agttcaagac tctgagtgag gaagaaatag aaaaagtgct   720
gaaaatatat tttaatattt ccttgcagag aaagcttgtg cccaaacatg gtgatagatt   780
ttttactatt tagaataagg agtaaaacaa tcttgtctat ttgtcatcca gctcaccagt   840
tatcaactga cgacctatca tgtatcttct gtaccttac cttatttgaa agaaaatc    898

<210> SEQ ID NO 82
<211> LENGTH: 900
<212> TYPE: DNA
<213> ORGANISM: Homo sapiens
<220> FEATURE:
<223> OTHER INFORMATION: NAT2

-continued

```
<400> SEQUENCE: 82
tcttgagcac cagatccggg ctgttccctt tgagaacctt aacatgcatt gtgggcaagc       60
catggagttg ggcttagagg ctattttga tcacattgta agaagaaacc ggggtgggtg      120
gtgtctccag gtcaatcaac ttctgtactg ggctctgacc acaatcggtt ttcagaccac     180
aatgttagga gggtattttt acatccctcc agttaacaaa tacagcactg gcatggttca     240
ccttctcctg caggtgacca ttgacggcag gaattacatt gtcgatgctg ggtctggaag     300
ctcctcccag atgtggcagc ctctagaatt aatttctggg aaggatcagc ctcaggtgcc     360
ttgcattttc tgcttgacag aagagagagg aatctggtac ctggaccaaa tcaggagaga     420
gcagtatatt acaaacaaag aatttcttaa ttctcatctc ctgccaaaga agaaacacca     480
aaaaatatac ttatttacgc ttgaacctcg aacaattgaa gattttgagt ctatgaatac     540
atacctgcag acgtctccaa catcttcatt tataaccaca tcattttgtt ccttgcagac     600
cccagaaggg gtttactgtt tggtgggctt catcctcacc tatagaaaat tcaattataa     660
agacaataca gatctggtcg agtttaaaac tctcactgag gaagaggttg aagaagtgct     720
gaaaaatata tttaagattt ccttggggag aaatctcgtg cccaaacctg gtgatggatc     780
ccttactatt tagaataagg aacaaaataa acccttgtgt atgtatcacc caactcacta     840
attatcaact tatgtgctat cagatatcct ctctaccctc acgttatttt gaagaaaatc     900
```